(12) United States Patent
DeFrees

(10) Patent No.: US 7,691,603 B2
(45) Date of Patent: *Apr. 6, 2010

(54) INTRACELLULAR FORMATION OF PEPTIDE CONJUGATES

(75) Inventor: Shawn DeFrees, North Wales, PA (US)

(73) Assignee: Novo Nordisk A/S, Bagsvaerd (DK)

( * ) Notice: Subject to any disclaimer, the term of this patent is extended or adjusted under 35 U.S.C. 154(b) by 598 days.

This patent is subject to a terminal disclaimer.

(21) Appl. No.: 10/549,528

(22) PCT Filed: Apr. 9, 2004

(86) PCT No.: PCT/US2004/011061

§ 371 (c)(1),
(2), (4) Date: Sep. 19, 2005

(87) PCT Pub. No.: WO2004/091499

PCT Pub. Date: Oct. 28, 2004

(65) Prior Publication Data

US 2006/0177892 A1    Aug. 10, 2006

Related U.S. Application Data

(60) Provisional application No. 60/462,144, filed on Apr. 9, 2003.

(51) Int. Cl.
- C12P 21/06     (2006.01)
- C12P 21/08     (2006.01)
- C12N 9/24      (2006.01)
- A61K 38/00     (2006.01)
- A61K 38/16     (2006.01)

(52) U.S. Cl. ............. 435/68.1; 435/200; 435/325; 530/303; 530/351; 530/345; 530/388.23; 514/2; 514/8

(58) Field of Classification Search .......... None
See application file for complete search history.

(56) References Cited

U.S. PATENT DOCUMENTS

| | | |
|---|---|---|
| 4,055,635 A | 10/1977 | Green et al. |
| 4,088,538 A | 5/1978 | Schneider |
| 4,179,337 A | 12/1979 | Davis et al. |
| 4,385,260 A | 5/1983 | Watts et al. |
| 4,412,989 A | 11/1983 | Iwashita et al. |
| 4,414,147 A | 11/1983 | Klibanov |
| 4,496,689 A | 1/1985 | Mitra |
| 4,565,653 A | 1/1986 | Ives et al. |
| 4,806,595 A | 2/1989 | Noishiki et al. |
| 4,925,796 A | 5/1990 | Bergh et al. |
| 5,153,265 A | 10/1992 | Shadle et al. |
| 5,154,924 A | 10/1992 | Friden |
| 5,169,933 A | 12/1992 | Anderson et al. |
| 5,182,107 A | 1/1993 | Friden |
| 5,346,696 A | 9/1994 | Kim et al. |
| 5,352,670 A | 10/1994 | Venot |
| 5,369,017 A | 11/1994 | Wong et al. |
| 5,374,541 A | 12/1994 | Wong |
| 5,405,753 A | 4/1995 | Brossmer |
| 5,432,059 A | 7/1995 | Bean |
| 5,492,841 A | 2/1996 | Craig |
| 5,527,527 A | 6/1996 | Friden |
| 5,545,553 A | 8/1996 | Gotschlich |
| 5,614,184 A | 3/1997 | Sytkowski et al. |
| 5,621,039 A | 4/1997 | Hallahan et al. |
| 5,672,683 A | 9/1997 | Friden et al. |
| 5,716,812 A | 2/1998 | Withers et al. |
| 5,728,554 A | 3/1998 | Bayer et al. |
| 5,833,988 A | 11/1998 | Friden |
| 5,834,251 A | 11/1998 | Maras et al. |
| 5,849,535 A | 12/1998 | Cunningham et al. |
| 5,876,980 A | 3/1999 | DeFrees et al. |
| 5,922,577 A | 7/1999 | DeFrees et al. |
| 5,932,462 A | 8/1999 | Harris et al. |
| 5,945,314 A | 8/1999 | Prieto et al. |
| 5,969,040 A | 10/1999 | Hallahan et al. |
| 5,977,307 A | 11/1999 | Friden |
| 6,015,555 A | 1/2000 | Friden |
| 6,030,815 A | 2/2000 | DeFrees et al. |

(Continued)

FOREIGN PATENT DOCUMENTS

EP    0474313 A    3/1992

(Continued)

OTHER PUBLICATIONS

Gross, Hans Jurgen, Fluorescent CMP-sialic acids as a toll to study the specificity of the CMP-sialic acid carrier and the glycoconjugate sialylation in permeabilized cells, Eur. J. Biochem, 203, 269-275 (1992).*

(Continued)

*Primary Examiner*—Anish Gupta
*Assistant Examiner*—Julie Ha
(74) *Attorney, Agent, or Firm*—Leydig, Voit & Mayer, Ltd.

(57) ABSTRACT

The invention includes methods and compositions for forming peptide conjugates intracellularly having a covalent linkage between a modifying group and a glycosylated or non-glycosylated peptide. The modifying group is conjugated to the peptide via a glycosyl linking group interposed between and covalently linked to both the peptide and the modifying group.

17 Claims, 3 Drawing Sheets

U.S. PATENT DOCUMENTS

| | | | |
|---|---|---|---|
| 6,037,452 | A | 3/2000 | Minamino et al. |
| 6,057,292 | A | 5/2000 | Cunningham et al. |
| 6,075,134 | A | 6/2000 | Bertozzi et al. |
| 6,087,325 | A | 7/2000 | Meers et al. |
| 6,096,512 | A | 8/2000 | Elhammer et al. |
| 6,166,183 | A | 12/2000 | Ishikawa et al. |
| 6,183,738 | B1 | 2/2001 | Clark |
| 6,261,805 | B1 | 7/2001 | Wood |
| 6,362,254 | B2 | 3/2002 | Harris et al. |
| 6,440,703 | B1 | 8/2002 | DeFrees |
| 6,458,937 | B1 | 10/2002 | Bertozzi et al. |
| 6,555,346 | B1 | 4/2003 | Kretzdorn et al. |
| 6,692,931 | B1 | 2/2004 | Reutter et al. |
| 7,202,208 | B2 | 4/2007 | Papadimitriou |
| 7,265,085 | B2 * | 9/2007 | DeFrees et al. .......... 514/8 |
| 2002/0137134 | A1 | 9/2002 | Gerngross et al. |
| 2002/0150981 | A1 | 10/2002 | Canfield |
| 2002/0168323 | A1 | 11/2002 | Gonda et al. |
| 2003/0027257 | A1 | 2/2003 | Iatrou et al. |
| 2004/0136955 | A1 | 7/2004 | Barker |
| 2004/0137557 | A1 | 7/2004 | DeFrees et al. |

FOREIGN PATENT DOCUMENTS

| | | |
|---|---|---|
| EP | 0585109 A | 3/1994 |
| EP | 0605963 A2 | 7/1994 |
| WO | WO 87/00056 | 1/1987 |
| WO | WO 87/05330 A1 | 9/1987 |
| WO | WO 89/10134 A1 | 11/1989 |
| WO | WO 90/07572 | 7/1990 |
| WO | WO 92/18135 | 10/1992 |
| WO | WO 94/05332 | 3/1994 |
| WO | WO 94/15625 A1 | 7/1994 |
| WO | WO 95/02421 A1 | 1/1995 |
| WO | WO 96/40731 | 6/1996 |
| WO | WO 96/32491 | 10/1996 |
| WO | WO 97/05330 | 2/1997 |
| WO | WO 98/05363 | 2/1998 |
| WO | WO 98/31826 | 7/1998 |
| WO | WO 98/58964 | 12/1998 |
| WO | WO 99/00150 A2 | 1/1999 |
| WO | WO 99/22764 A1 | 5/1999 |
| WO | WO 00/23114 | 4/2000 |
| WO | WO 00/65087 | 11/2000 |
| WO | WO 01/49830 A2 | 7/2001 |
| WO | WO 01/58935 A2 | 8/2001 |
| WO | WO 01/60411 A1 | 8/2001 |
| WO | WO 02/02597 A2 | 1/2002 |
| WO | WO 02/13843 A2 | 2/2002 |
| WO | WO 02/13873 A1 | 2/2002 |
| WO | WO 02/074806 A2 | 9/2002 |
| WO | WO 02/002764 A2 | 10/2002 |
| WO | WO 03/017949 A2 | 3/2003 |
| WO | WO 03/031464 A2 | 4/2003 |
| WO | WO 2004/099231 A2 | 11/2004 |

OTHER PUBLICATIONS

Oetke et al, "Versitile Biosynthetic Engineering of Sialic Acid in Living Cells Using Synthetic Sialic Acid Analogues," The Journal of Biological Chemistry (2002), pp. 668-6695, from Applicant's IDS.*
Abeijon et al., 1986, J. Biol. Chem. 261(24):11374-11377.
Abuchowski et al., 1977, J. Biol. Chem. 252:3582-3586.
Abuchowski et al., 1984, Cancer Biochem. Biophys. 7:175-186.
Abuchowski et al., 1977, J. Biol. Chem. 252:3578-3581.
Ailor et al., 2000, Glycobiology 10:837-847.
Allegre et al., 2006, J. Membrane Science 269:109-117.
Altmann et al., 1999, Glycoconjugate J. 16:109-123.
Aplin et al., 1981, CRC Crit Rev. Biochem. 259-306.
Beauchamp et al., 1983, Anal Biochem.131:25-33.
Berger et al., 1988, Blood 71:1641-1647.
Berg-Fassman et al. 1993, J. Biol. Chem. 268:14861-14866.
Bhadra et al., 2002, Pharmazie 57:5-29.
Bhatia et al., 1989, Anal. Biochem. 178:408-413.
Bickel et al., 2001, Adv. Drug Deliv. Rev. 46:247-279.
Bjoern, et al., 1992, J. Biol. Chem., 266(17):11051-11057.
Boccu et al., 1983, Z. Naturforsch 38C:94-99.
Boime et al., 1995, Endocrinology 135:2635-2640.
Boissel et al., 1993, J. Biol. Chem. 268:15983-15993.
Bouizar et al., 1986, Eur. J. Biochem. 155:141-147.
Boyd et al., 1995, Mol. Immunol. 32:1311-1318.
Browning et al., 1989, J. Immunol. 143:1859-1867.
Bückmann et al., 1981, Makromol. Chem. 182:1379-1384.
Burns et al., 2002, Blood 99:4400-4405.
Busterbosch et al., 1996, Eur. J. Biochem. 237:344-349.
Butnev et al., 1998, Biology of Reproduction 58:458-469.
Byun et al., 1992, ASAIO Journal M649-M653.
Casares et al., 2001, Nature Biotech 19:142-147.
Chaffee et al., 1992, J. Clin. Invest 89:1643-1651.
Charter et al., 2000, Glycobiology 10:1049-1056.
Chern et al., 1991, Eur. J. Biochem. 202:225-229.
Chiba et al., 1995, Biochem J. 308:405-409.
Chrisey et al., 1996, Nucleic Acids Res. 24:3031-3039.
Clark, et al., 1996, J. Biol. Chem,271(36)21969-21977.
Cointe, et al., 2000, Glycobiology, 10(5):511-519.
Conradt et al., 1987, J. Biol. Chem. 262:14600-14605.
Cope et al., 1991, Molecular Microbiology 5(5):1113-1124.
Copeland, Robert A., 2000, Enzymes, Second Edition, 146-150.
Crout et al., 1998, Curr. Opin. Chem. Biol. 2:98-111.
DeFrees, 2006, Glycobiology 16:833-843.
Delgado et al., 1992, Critical Reviews in Therapeutic 9:249-304.
Delgaldo et al., 1990, Biotechnol. Appl. Biochem. 12:119-128.
Detty et al., 1982, J. Org. Chem. 47:5416-5418.
Douglas, et al., 1991, J. Am. Chem. Soc., 113:5095-5097.
Dunn et al., 1991, Eds. Polymeric Drugs and Drug Delivery Systems, ACS Symposium Series vol. 469, American Chemical Society, Washington D.C.
Durieux, et al., 2001, Tetrahedron Letters, 42:2297-2299.
Dwek et al., 1995, J Anat. 187:279-292.
Eavarone et al., 2000, J. Biomed Mater. Res. 51:10-14.
Fan et al., 1997, J. Biol. Chem. 272(43):27068-27064.
Fibi et al., 1995, Cells Blood 85:1229-1236.
Fischer et al., 1998, Thrombosis Research 89:147-150.
Flynn et al., 2000, Curr. Opin. Oncol. 12:574-581.
Garnett et al., 2002, Advanced Drug Delivery Reviews 53:171-216.
Gatot, et al., 1998, J. Biol. Chem., 273(21):12870-12880.
Gillis et al., 1988, Behring Inst. Mitt. August 83:1-7.
Ginns, Dr. Edward, PEG Glucocerebrosidase, Internet page from www.gauch.org.uk/peg2.prg, printed Jun. 21, 2002.
Gotschlich, Emil C., 1994, J. Exp. Med., Coden: Jemeav; ISSN: 0022-1007, 180(6):2181-90.
Grabenhorst, et al., 1993, Euro. J. Biochem., 215:189-197.
Grodberg et al., 1993, Eur. J. Biochem. 218:597-601.
Gross, H.J., 1992, Eur. J. Biochem. 203(1-2):269-275.
Hall et al., 2001, Methods in Molecular Biology 166:139-154.
Haneda et al., Carbohydr. Res. 292:61-70.
Hang et al., 2001, J. Am. Chem. Soc. 123:1242-1243.
Harris, 1985, Macronol. Chem. Phys. C25: 325-373.
Harris et al., 2003, Nature Reviews Drug Discovery, 2:214-221.
Hayes et al., 1993, J. Biol. Chem. 268(22):16170-16178.
Hellstrom et al., 2001, Methods in Molecular Biology 166:3-16.
Hermanson et al., 1992, Immobilized Affinity Ligand Techniques, Academic Press.
Hermanson, 1996, Bioconjugate Techniques, Academic Press, San Diego.
Hermentin, et al., 1996, Glycobiology 6(2):217-230.
Hills et al., 2002, American Biotechnology Laboratory, 20(11):30.
Hollister et al., 2001, Glycobiology 11:1-19.
Hounsell et al., 1996, Glycoconj. J. 13:19-26.
Ichikawa et al., 1992, J. Am. Chem. Soc. 114:9283-9298.
Inoue et al., 1995, Biotechnology Annual Review 1:297-313.
Ito et al., 1993, Pure & Appl. Chem. 65(4):753-762.
Jackson et al., 1987, Anal. Biochem.165:114-127.
Jarvis et al., 1998, Curr. Opin Biotechnol. 9:528-533.
Joppich et al., 1979, Makromol Chem. 180:1381-1384.

Joshi et al., 1990, J. Biol. Chem. 265:14518-14525.
Jung et al., 1983, Biochem. Biophys. Acta, 761:152-162.
Kalsner et al., 1995, Glycoconj. J. 12:360-370.
Kasina et al., 1998 Bioconjugate Chem., 9:108-117.
Katre et al., 1987, Proc. Natl. Acad. Sci. U.S.A. 84:1487-1491.
Keppler et al., 2001, Glycobiology 11:11R-18R.
Kitamura et al., 1990, Biochem. Biophys. Res. Commun. 28:1387-1394.
Kitamura et al., 1991, Cancer Res. 51:4310-4315.
Kodama et al., 1993, Tetrahedron Lett. 34:6419-6422.
Koeller et al., 2000, Nature Biotechnology 18: 835-841.
Koeller et al., 2002, Nature, 409:232-240.
Koide et al., 1983, Biochem Biophys. Res. Commun. 111:659-667.
Kreitmann 2001, Current Pharmaceutical Biotechnology 2:313-325.
Kuhn, et al., 1995, J. Biol. Chem. 270(49):29493-29497.
Lai et al, 1986, J. Biol. Chem. 261:3116-3121.
Lee-Huang et al., 1984, Proc. Natl. Acad. Sci. U.S.A. 81:2708-2712.
Lee et al., 1989, Biochemistry 28:1856-1861.
Leung, S., 1995, J. Immunology, 154:5919-5926.
Li et al., 2002, Trends in Pharmacological Sciences 23:206-209.
Li et al., 2002, Medicinal Research Reviews 22:225-250.
Liu et al., 2002, 1996, Chem. Eur. J. 2:1359-1362.
Long et al., 2006, Experimental Hematology 34:697-704.
Lord et al., 2001, Clin. Cancer Res. 7:2085-2090.
Lougheed et al., 1999, J. Biol. Chem. 274:37717-37722.
Luckow et al., 1993, Curr. Opin. Biotechnol 4:564-572.
Lund et al., 1995, FASEB J. 9:115-119.
Lund et al., 1996, J. Immunol. 157:4963-4969.
Mahal et al., 1997, Science 276:1125-1128.
Maranga et al., 2003, Biotechnology and Bioengineering 84(2):245-253.
Maras et al., 2000, Molecular cloning and enzymatic characterization of a Trichoderma reesei , 2-α-D-mannosidase, 77:255-263.
Miller et al., 1993, Curr. Opin. Genet. Dev. 3:97-101.
Min et al., 1996, Endocr. J. 43;585-593.
Mistry et al., 1996, Lancet 348:1555-1559.
Morimoto et al., 1996, Glycoconjugate J. 13:1013-1020.
Nilsson et al., 1984, Methods Enzymol. 104:56-69.
O'Connell et al., 1992, J. Biol. Chem. 267:25010-25018.
Oetke et al., 2002, J. Biol. Chem. 277:6688-6695.
Olson et al., 1999, J. Biol. Chem. 274:29889-29896.
Palacpac et al., 1999, PNAS USA 96:4692-4697.
Park et al., 1986, J. Biol. Chem. 261:205-210.
Paulson et al., 1997, J. Biol. Chem. 252:8624-8628.
Plummer et al., 1995, J. Biol. Chem. 270(22):13192-13196.
PNGase-F Amidase Sequence from *F. meningosepticum* (Registry Nos. 128688-70-0).
PNGase-F Amidase Sequence from *F. meningosepticum* (Registry Nos. 128688-71-1).
Pyatak et al., 1980, Res. Commun. Chem. Pathol Pharmacol 29:113-127.
Rabouille et al., 1999, J. Cell. Biol. 112:3319-3330.
Reff et al., 2002, Cancer Control 9:152-166.
Rosenthal, et al., 1994, Methods Enzymol. 235:253-285.
Sadler et al., 1982, Methods in Enzymology 83:458-514.
Saneyoshi et al., 2001, Biology of Reproduction 65:1686-1690.
Saxon et al., 2000, Science 287:2007-2010.
Schwientek et al., 1994, Gene 145:299-303.
Scouten 1987, Methods in Enzymology 135:30-65.
Shah et al., 1996, J. Pharm. Sci. 85:1306-1311.
Shapiro et al., 2005, B. Biochemistry 105:518-525.
Singh et al., 1996, Chem. Commun. 1996:993-994.
Sinha et al., 1980, Infection and Immunity 29(3):914-925.
Song et al., 2002, J. Pharmacol. Exp. Ther. 301:605-610.
Srinivasachar et al., 1989, Biochemistry 28:2501-2509.
Stephens et al., 1983, European J. of Biochem., 135(3):519-27.
Stephens et al., 1983, European J. of Biochem., 133(3):481-9.
Stephens et al., 1983, European J. of Biochem., 133(1):155-62.
Takane et al., 2000, J. Pharmacology and Experimental Therapeutics 294:746-752.
Takeda et al., 1995, Trends Biochem. Sci. 20:367-371.
Takeuchi, et al., 1990, The Journal of Biological Chemistry, 265(21): 12127-12130.
Tanner et al., 1987, Biochim. Biophys. Acta., 906:81-91.
Taylor et al., 1991, Protein Immobilization Fundamentals and Applications, Manual.
Thotakura et al., 1987, Meth Enzymol 138: 350-359.
Tsuboi et al., 2000 Archives of Biochemistry and Biophysics 374:100-106.
Tuddenham, E., 2002, Nature 419:23-24.
Udenfriend et al., 1995, Ann. Rev. Biochem. 64:563-591.
Ulloa-Aguirre et al., 1999, Role of Glycosylation in Function of Follicle-Stimulating Hormone, Endocrine 11:205-215.
Uludag et al., 2002, Biotechnol. Prog. 18:604-611.
Urdal et al, 1984, J. Chromatog, 296:171-179.
Van Berkel et al., 1996, Biochem J. 319:117-122.
Veronese et al., 1985, Appl. Biochem. Biotech. 11:141-152.
Vocadlo et al., 2000, In Carbohydrate Chemistry and Biology, vol. 2.
Vyas et al., 2001, Crit. Rev. Ther. Drug Carrier Syst. 18:1-76.
Wang et al., 1996, Tetrahedron Lett. 37:1975-1978.
Wang, M., 1998, Protein Engineering 11(12):1277-1283.
Wellhoner et al., 1991, J. Biol. Chem. 226:4309-4314.
Witte K. et al., 1997, J. Am. Chem. Soc. 119:2114-2118.
Woghiren et al., 1993, Bioconjugate Chem. 4:314-318.
Wong et al., 1992, Enzyme Microb.Technol. 14:866-874.
Wong et al., 1996, Biotechnology and Bioengineering 49:659-666.
Woods et al., 1989, Eur. J. Cell. Biol. 50:132-143.
Wright et al., 1998, J. Immunol. 160:3393-3402.
Wu et al., 2002, J. Drug targeting 10:239-245.
Xing et al., 1998, Biochem. J. 336:667-673.
Yamamoto et al., 1998, Carbohydr. Res. 305:415-422.
Yarema et al., 1998, J. Biol. Chem. 47:31168-31179.
Yoshida et al., 1999, Glycobiology 9:53-58.
Yoshitake et al., 1985, Biochemistry 24:3736-3750.
Zalipsky 1995, Bioconjugate Chem. 6:150-165.
Zalipsky et al., 1992, Poly (ethylene glycol) Chemistry: Biotechnical and Biomedical Applications 347-370.
Zheng et al., 1999, Biotechnology and Bioengineering 65(5):600-604.
Zhou, et al., 1994, Mol. Microbiol. 14(4):609-618.

* cited by examiner

INTRACELLULAR FORMATION OF PEPTIDE CONJUGATES

BACKGROUND OF THE INVENTION

The administration of glycosylated and non-glycosylated peptides for engendering particular physiological response is well known in the medicinal arts. Among the best known peptides utilized for this purpose is insulin, which is used to treat diabetes. Enzymes have also been used for their therapeutic benefits. A principal factor, which has limited the use of therapeutic peptides is the immunogenic nature of most peptides. In a patient, an immunogenic response to an administered peptide can neutralize the peptide and/or lead to the development of an allergic response in the patient. Other deficiencies of therapeutic glycopeptides include suboptimal potency and rapid clearance rates. The problems inherent in peptide therapeutics are recognized in the art, and various methods of eliminating the problems have been investigated. To provide soluble peptide therapeutics, synthetic polymers have been attached to the peptide backbone.

Poly(ethylene glycol) ("PEG") is an exemplary polymer that has been conjugated peptides. The use of PEG to derivatize peptide therapeutics has been demonstrated to reduce the immunogenicity of the peptides. For example, U.S. Pat. No. 4,179,337 (Davis et al. concerns non-immunogenic polypeptides, such as enzymes and peptide hormones couplpled polyethylene glycol (PEG) or polypropylene glycol. Between 10 and 100 moles of polymer are used per mole polypeptide and at least 15% of the physiological activity is maintained. In addition, the clearance time in circulation is prolonged due to the increased size of the PEG-conjugate of the polypeptides in question.

WO 93/15189 (Veronese et al.) concerns a method to maintain the activity of polyethylene glycol-modified proteolytic enzymes by linking the proteolytic enzyme to macromolecularized inhibitor. The conjugates are intended for medical applications.

The principal mode of attachment of PEG, and its derivatives, to peptides is a specific bonding through a peptide amino acid residue. For example, U.S. Pat. No. 4,088,538 discloses an enzymatically active polymer-enzyme conjugate of an enzyme covalently bound to PEG. Similarly, U.S. Pat. No. 4,496,689 discloses a covalently attached complex of α-1 proteinase inhibitor with a polymer such as PEG or methoxypoly(ethyleneglycol) ("mPEG"). Abuchowski et al. (*J. Biol. Chem.* 252: 3578 (1977) discloses the covalent attachment of mPEG to an amine group of bovine serum albumin. U.S. Pat. No. 4,414,147 discloses a method of rendering interferon less hydrophobic by conjugating it to an anhydride of a dicarboxylic acid, such as poly(ethy succinic anhydride). PCT WO 87/00056 discloses conjugation of PEG and poly(oxyethylated) polyols to such proteins as interferon-β, interleukin-2 and immunotoxins. EP 154,316 discloses and claims chemically modified lymphokines, such as IL-2 containing PEG bonded directly to at least one primary amino group of the lymphokine. U.S. Pat. No. 4,055,635 discloses pharmaceutical compositions of a water-soluble complex of a proteolytic enzyme linked covalently to a polymeric substance such as a polysaccharide.

Another mode of attaching PEG to peptides is through the non-specific oxidation of glycosyl residues on a glycopeptide. The oxidized sugar is utilized as a locus for attaching a PEG moiety to the peptide. For example M'Timkulu (WO 94/05332) discloses the use of an amino-PEG to add PEG to a glycoprotein. The glycosyl moieties are randomly oxidized to the corresponding aldehydes, which are subsequently coupled to the amino-PEG.

In each of the methods described above, poly(ethyleneglycol) is added in a random, non-specific manner to reactive residues on a peptide backbone. For the production of therapeutic peptides, it is clearly desirable to utilize a derivatization strategy that results in the formation of a specifically labeled, readily characterizable, essentially homogeneous product. A promising route to preparing specifically labeled peptides is through the use of enzymes, such as glycosyltransferases to append a modified sugar moiety onto a peptide.

Enzyme-based syntheses have the advantages of regioselectivity and stereoselectivity. Moreover, enzymatic syntheses are performed using unprotected substrates. Two principal classes of enzymes are used in the synthesis of carbohydrates, glycosyltransferases (e.g., sialyltransferases, oligosaccharyltransferases, N-acetylglucosaminyltransferases), and glycosidases. The glycosidases are further classified as exoglycosidases (e.g., β-mannosidase, β-glucosidase), and endoglycosidases (e.g., Endo-A, Endo-M). Each of these classes of enzymes has been successfully used synthetically to prepare carbohydrates. For a general review, see, Crout et al., *Curr. Opin. Chem. Biol.* 2: 98-111 (1998).

Glycosyltransferases can be used to modify the oligosaccharide structures on glycopeptides. Glycosyltransferases are effective for producing specific products with good stereochemical and regiochemical control. Glycosyltransferases have been used to prepare oligosaccharides and to modify terminal N- and O-linked carbohydrate structures, particularly on glycopeptides produced in mammalian cells. For example, the terminal oligosaccharides of glycopeptides have been completely sialylated and/or fucosylated to provide more consistent sugar structures, which improves glycopeptide pharmacodynamics and a variety of other biological properties.

β-1,4-galactosyltransferase was used to synthesize lactosamine, an illustration of the utility of glycosyltransferases in the synthesis of carbohydrates (see, e.g., Wong et al., *J. Org. Chem.* 47: 5416-5418 (1982)). Numerous synthetic procedures have made use of α-sialyltransferases to transfer sialic acid from cytidine-5'-monophospho-N-acetylneuraminic acid to the 3-OH or 6-OH of galactose (see, e.g., Kevin et al., *Chem. Eur. J.* 2: 1359-1362 (1996)). Fucosyltransferases are used in synthetic pathways to transfer a fucose unit from guanosine-5'-diphosphofucose to a specific hydroxyl of a saccharide acceptor. For example, Ichikawa prepared sialyl Lewis-X by a method that involves the fucosylation of sialylated lactosamine with a cloned fucosyltransferase (Ichikawa et al., *J. Am. Chem. Soc.* 114: 9283-9298 (1992)). For a discussion of recent advances in glycoconjugate synthesis for therapeutic use see, Koeller et al., *Nature Biotechnology* 18: 835-841 (2000). See also, U.S. Pat. Nos. 5,876,980; 6,030,815; 5,728,554; 5,922,577; and WO/9831826.

Glycosidases can also be used to prepare saccharides. Glycosidases normally catalyze the hydrolysis of a glycosidic bond. Under appropriate conditions, however, they can be used to form this linkage. Most glycosidases used for carbohydrate synthesis are exoglycosidases; the glycosyl transfer occurs at the non-reducing terminus of the substrate. The glycosidase takes up a glycosyl donor in a glycosyl-enzyme intermediate that is either intercepted by water to give the hydrolysis product, or by an acceptor, to give a new glycoside or oligosaccharide. An exemplary pathway using an exoglycosidase is the synthesis of the core trisaccharide of all N-linked glycopeptides, including the notoriously difficult β-mannoside linkage, which was formed by the action of β-mannosidase (Singh et al., *Chem. Commun.* 993-994 (1996)).

In another exemplary application of the use of a glycosidase to form a glycosidic linkage, a mutant glycosidase has been prepared in which the normal nucleophilic amino acid within the active site is changed to a non-nucleophilic amino acid. The mutant enzymes do not hydrolyze glycosidic linkages, but can still form them. The mutant glycosidases are used to prepare oligosaccharides using an α-glycosyl fluoride donor and a glycoside acceptor molecule (Withers et al., U.S. Pat. No. 5,716,812). Although the mutant glycosidases are useful for forming free oligosaccharides, it has yet to be demonstrated that such enzymes are capable of appending glycosyl donors onto glycosylated or non-glycosylated peptides, nor have these enzymes been used with unactivated glycosyl donors.

Although their use is less common than that of the exoglycosidases, endoglycosidases are also utilized to prepare carbohydrates. Methods based on the use of endoglycosidases have the advantage that an oligosaccharide, rather than a monosaccharide, is transferred. Oligosaccharide fragments have been added to substrates using endo-β-N-acetylglucosamines such as endo-F, and endo-M (Wang et al., *Tetrahedron Lett.* 37: 1975-1978; and Haneda et al., *Carbohydr. Res.* 292: 61-70 (1996)).

In addition to their use in preparing carbohydrates, the enzymes discussed above are applied to the synthesis of glycopeptides as well. The synthesis of a homogenous glycoform of ribonuclease B has been published (Witte K. et al., *J. Am. Chem. Soc.* 119: 2114-2118 (1997)). The high mannose core of ribonuclease B was cleaved by treating the glycopeptide with endoglycosidase H. The cleavage occurred specifically between the two core GlcNAc residues. The tetrasaccharide sialyl Lewis X was then enzymatically rebuilt on the remaining GlcNAc anchor site on the now homogenous protein by the sequential use of β-1,4-galactosyltransferase, α-2,3-sialyltransferase and α-1,3-fucosyltransferase V. Each enzymatically catalyzed step proceeded in excellent yield.

Methods combining both chemical and enzymatic synthetic elements are also known. For example, Yamamoto and coworkers (*Carbohydr. Res.* 305: 415-422 (1998)) reported the chemoenzymatic synthesis of the glycopeptide, glycosylated Peptide T, using an endoglyosidase. The N-acetylglucosaminyl peptide was synthesized by purely chemical means. The peptide was subsequently enzymatically elaborated with the oligosaccharide of human transferrin glycopeptide. The saccharide portion was added to the peptide by treating it with an endo-β-N-acetylglucosaminidase. The resulting glycosylated peptide was highly stable and resistant to proteolysis when compared to the peptide T and N-acetylglucosaminyl peptide T.

The use of glycosyltransferases to modify peptide structure with reporter groups has been explored. For example, Brossmer et al. (U.S. Pat. No. 5,405,753) discloses the formation of a fluorescent-labeled cytidine monophosphate ("CMP") derivative of sialic acid and the use of the fluorescent glycoside in an assay for sialyl transferase activity and for the fluorescent-labeling of cell surfaces, glycoproteins and gangliosides. Gross et al. (*Analyt. Biochem.* 186: 127 (1990)) describe a similar assay. Bean et al. (U.S. Pat. No. 5,432,059) discloses an assay for glycosylation deficiency disorders utilizing reglycosylation of a deficiently glycosylated protein. The deficient protein is reglycosylated with a fluorescent-labeled CMP glycoside. Each of the fluorescent sialic acid derivatives is substituted with the fluorescent moiety at either the 9-position or at the amine that is normally acetylated in sialic acid. The methods using the fluorescent sialic acid derivatives are assays for the presence of glycosyltransferases or for non-glycosylated or improperly glycosylated glycoproteins. The assays are conducted on small amounts of enzyme or glycoprotein in a sample of biological origin. The enzymatic derivatization of a glycosylated or non-glycosylated peptide on a preparative or industrial scale using a modified sialic acid has not been disclosed or suggested.

Considerable effort has also been directed towards the modification of cell surfaces by altering glycosyl residues presented by those surfaces. For example, Fukuda and coworkers have developed a method for attaching glycosides of defined structure onto cell surfaces. The method exploits the relaxed substrate specificity of a fucosyltransferase that can transfer fucose and fucose analogs bearing diverse glycosyl substrates (Tsuboi et al., *J. Biol. Chem.* 271: 27213 (1996)).

Enzymatic methods have also been used to activate glycosyl residues on a glycopeptide towards subsequent chemical elaboration. The glycosyl residues are typically activated using galactose oxidase, which converts a terminal galactose residue to the corresponding aldehyde. The aldehyde is subsequently coupled to an amine-containing modifying group. For example, Casares et al. (*Nature Biotech.* 19: 142 (2001)) have attached doxorubicin to the oxidized galactose residues of a recombinant MHCII-peptide chimera.

Glycosyl residues have also been modified to bear reactive functional groups, such as ketone groups. For example, Mahal and co-workers (*Science* 276: 1125 (1997)) have prepared N-levulinoyl mannosamine ("ManLev"), which has a ketone functionality at the position normally occupied by the acetyl group in the natural substrate. Cells were treated with the ManLev, thereby incorporating a ketone group onto the cell surface. See, also Saxon et al., *Science* 287: 2007 (2000); Hang et al., *J. Am. Chem. Soc.* 123: 1242 (2001); Yarema et al., *J. Biol. Chem.* 273: 31168 (1998); and Charter et al., *Glycobiology* 10: 1049 (2000). The ketone group may then be subsequently modified, ex vivo, with a modifying group fashioned with a reactive aminooxy, hydrazide, or thiosemicarbazide moiety. See, Bertozzi et al., U.S. Pat. Nos. 6,075,134 and 6,458,937. The ex vivo reaction occurs on the cell surface and has been termed "Staudinger ligation."

However, the methods of cell surface modification have not been utilized to enzymatically incorporate a preformed modified glycosyl donor moiety into a peptide to produce a modified peptide with improved therapeutic or diagnostic properties. Therefore, despite the efforts directed toward the enzymatic elaboration of saccharide structures, there remains still a need for an industrially practical method for the modification of glycosylated and non-glycosylated peptides with modifying groups such as water-soluble polymers, therapeutic moieties, biomolecules and the like. Of particular interest are methods in which the modifying group provides enhanced therapeutic or diagnostic properties. The present invention fulfills these and other needs.

BRIEF SUMMARY OF THE INVENTION

The present invention provides methods for making a site specifically modified glycopeptide with enhanced therapeutic or diagnostic properties. The methods are based on the surprising discovery that a preformed modified sugar may be fed to a cell which subsequently internalizes the modified sugar and ultimately produces a site specifically modified peptide conjugate. Thus, this discovery provides a completely new modality in peptide conjugate synthesis.

Thus, in a first aspect, the present invention provides a method of forming a peptide conjugate having a covalent linkage between a modifying group and a glycosylated or non-glycosylated peptide, wherein the modifying group is conjugated to the peptide via a glycosyl linking group (e.g., intact glycosyl linking group) interposed between and covalently linked to both the peptide and the modifying group. The method includes contacting a cell with a first modified sugar having a sugar moiety and at least one modifying group. The modifying group is typically a water-soluble polymer, a therapeutic moiety, a detectable label, a biomolecule or a targeting moiety. The cell is incubated under conditions in which the first modified sugar is internalized. The first modified sugar is intracellularly contacted with a glycosylated or non-glycosylated peptide and a glycosyltransferase for which the modified nucleotide sugar is a substrate, thereby forming the peptide conjugate. The method also includes isolating the peptide conjugate.

In a second aspect, the present invention provides a method of forming a peptide conjugate having a covalent linkage between a modifying group and a glycosylated or non-glycosylated peptide. The modifying group is conjugated to the peptide via a glycosyl linking group (e.g., intact glycosyl linking group) interposed between and covalently linked to both the peptide and the modifying group. The method includes contacting a cell with a modified nucleotide sugar comprising a nucleotide sugar moiety and at least one modifying group. The modifying group is typically a water-soluble polymer, a therapeutic moiety, a detectable label, a biomolecule or a targeting moiety. The cell is incubated under conditions in which the modified nucleotide sugar is internalized. The modified nucleotide sugar is intracellularly contacted with a glycosylated or non-glycosylated peptide and a glycosyltransferase for which the modified nucleotide sugar is a substrate, thereby forming said peptide conjugate. The method also includes isolating the peptide conjugate.

In a third aspect, the present invention provides a method of forming a peptide conjugate having a covalent linkage between a modifying group and a glycosylated or non-glycosylated peptide, wherein the modifying group is conjugated to the peptide via a glycosyl linking group (e.g., intact glycosyl linking group) interposed between and covalently linked to both the peptide and the modifying group. The method includes contacting a cell with a first modified activated sugar having a sugar moiety and at least one modifying group. The modifying group is typically a water-soluble polymer, a therapeutic moiety, a detectable label, a biomolecule or a targeting moiety. The cell is incubated under conditions in which the first modified sugar is internalized. The first modified activated sugar is intracellularly contacted with a glycosylated or non-glycosylated peptide and a glycosyltransferase for which the first modified activated sugar is a substrate, thereby forming the peptide conjugate. The method also includes isolating the peptide conjugate.

In a fourth aspect, the invention provides a cell having a peptide conjugate. The peptide conjugate has a modifying group and a peptide. The modifying group is linked to the peptide via a glycosyl linking group (e.g., intact glycosyl linking group) interposed between and covalently linked to both the peptide and the modifying group. In addition, the modifying group is a water-soluble polymer, a therapeutic moiety, a detectable label, or a targeting moiety.

DETAILED DESCRIPTION OF THE INVENTION

Abbreviations

Figure 1:
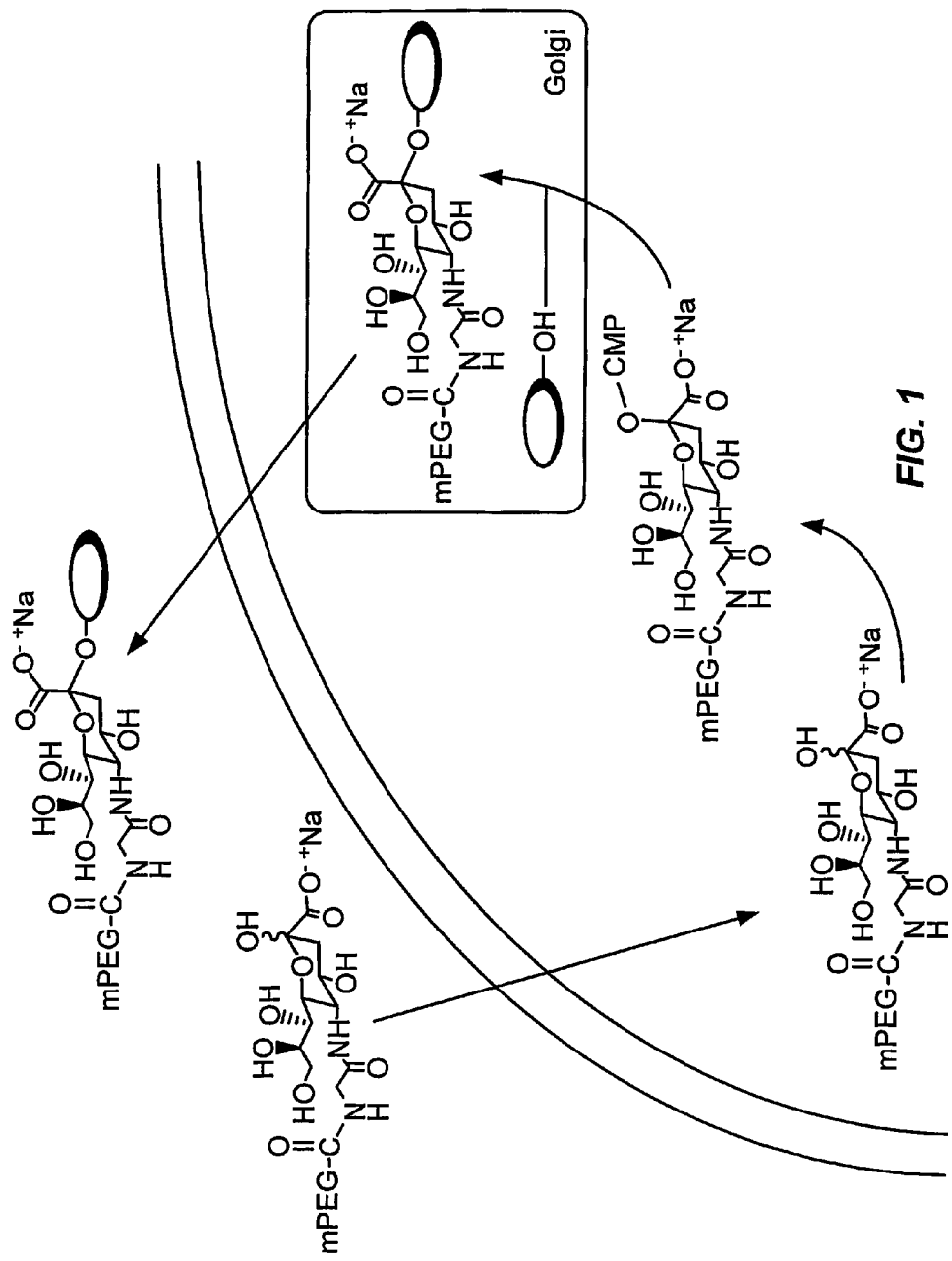
FIG. 1 is an illustration of the formation of a peptide conjugate using a sialic acid modified with polyethylene glycol

PEG, poly(ethyleneglycol); PPG, poly(propyleneglycol); Ara, arabinosyl; Fru, fructosyl; Fuc, fucosyl; Gal, galactosyl; GalNAc, N-acetylgalactosaminyl; Glc, glucosyl; GlcNAc, N-acetylglucosaminyl; Man, mannosyl; ManAc, mannosaminyl acetate; Xyl, xylosyl; WSP, water soluble polymer, and SA, sialic acid.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry and nucleic acid chemistry and hybridization are those well known and commonly employed in the art. Standard techniques are used for nucleic acid and peptide synthesis. The techniques and procedures are generally performed according to conventional methods in the art and various general references (see generally, Sambrook et al. MOLECULAR CLONING: A LABORATORY MANUAL, 2d ed. (1989) Cold Spring Harbor Laboratory Press, Cold Spring Harbor, N.Y., which is incorporated herein by reference), which are provided throughout this document. The nomenclature used herein and the laboratory procedures in analytical chemistry, and organic synthetic described below are those well known and commonly employed in the art. Standard techniques, or modifications thereof, are used for chemical syntheses and chemical analyses.

Oligosaccharides described herein may be described with the name or abbreviation for the non-reducing saccharide (i.e., Gal), followed by the configuration of the glycosidic bond (α or β), the ring bond (1 or 2), the ring position of the reducing saccharide involved in the bond (2, 3, 4, 6 or 8), and then the name or abbreviation of the reducing saccharide (i.e., GlcNAc). In some embodiments, each saccharide is a pyranose. For a review of standard glycobiology nomenclature see, *Essentials of Glycobiology* Varki et al. eds. CSHL Press (1999).

Oligosaccharides are typically considered to have a reducing end and a non-reducing end, whether or not the saccharide at the reducing end is in fact a reducing sugar. In accordance with accepted nomenclature, oligosaccharides are depicted herein with the non-reducing end on the left and the reducing end on the right.

As used herein, "nucleic acid" means DNA, RNA, single-stranded, double-stranded, or more highly aggregated hybridization motifs, and any chemical modifications thereof.

Modifications include, but are not limited to, those providing chemical groups that incorporate additional charge, polarizability, hydrogen bonding, electrostatic interaction, and functionality to the nucleic acid ligand bases or to the nucleic acid ligand as a whole. Such modifications include, but are not limited to, peptide nucleic acids (PNAs), phosphodiester group modifications (e.g., phosphorothioates, methylphosphonates), 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, methylations, unusual base-pairing combinations such as the isobases, isocytidine and isoguanidine and the like. Nucleic acids can also include non-natural bases, such as, for example, nitroindole. Modifications can also include 3' and 5' modifications such as capping with a fluorophore or another moiety.

The term "sialic acid" (SA) refers to any member of a family of nine-carbon carboxylated sugars. The most common member of the sialic acid family is N-acetyl-neuraminic acid (2-keto-5-acetamido-3,5-dideoxy-D-glycero-D-galactononulopyranos-1-onic acid (often abbreviated as Neu5Ac, NeuAc, or NANA). A second member of the family is N-glycolyl-neuraminic acid (Neu5Gc or NeuGc), in which the N-acetyl group of NeuAc is hydroxylated. A third sialic acid family member is 2-keto-3-deoxy-nonulosonic acid (KDN) (Nadano et al. (1986) *J. Biol. Chem.* 261: 11550-11557; Kanamori et al., *J. Biol. Chem.* 265: 21811-21819 (1990)). Also included are 9-substituted sialic acids such as a 9-O—$C_1$-$C_6$ acyl-Neu5Ac like 9-O-lactyl-Neu5Ac or 9-O-acetyl-Neu5Ac, 9-deoxy-9-fluoro-Neu5Ac and 9-azido-9-deoxy-Neu5Ac. For review of the sialic acid family, see, e.g., Varki, *Glycobiology* 2: 25-40 (1992); *Sialic Acids: Chemistry, Metabolism and Function*, R. Schauer, Ed. (Springer-Verlag, New York (1992)). The synthesis and use of sialic acid compounds in a sialylation procedure is disclosed in international application WO 92/16640, published Oct. 1, 1992.

"Peptide" refers to a polymer in which the monomers are amino acids and are joined together through amide bonds, alternatively referred to as a polypeptide or protein. Unnatural amino acids, for example, β-alanine, phenylglycine and homoarginine may also be included. Amino acids that are not gene-encoded may also be used in the present invention. Furthermore, amino acids that have been modified to include reactive groups, glycosylation sites, polymers, therapeutic moieties, biomolecules and the like may also be used in the invention. All of the amino acids used in the present invention may be either the D- or L-isomer The L-isomer is generally preferred. In addition, other peptidomimetics are also useful in the present invention. As used herein, "peptide" refers to both glycosylated and unglycosylated peptides. Also included are peptides that are incompletely glycosylated by a system that expresses the peptide. For a general review, see, Spatola, A. F., in CHEMISTRY AND BIOCHEMISTRY OF AMINO ACIDS, PEPTIDES AND PROTEINS, B. Weinstein, eds., Marcel Dekker, New York, p. 267 (1983).

The term "peptide conjugate," refers to species of the invention in which a peptide is conjugated with a modified sugar as set forth herein.

The term "amino acid," refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

As used herein, a "glycosyltransferase" refers to an enzyme capable of transferring a modified sugar to an amino acid and/or glycosyl residue on a peptide. Glycosyltransferase include those enzymes found in nature as well as recombinant enzymes (e.g. glysosyl trans-sialidase, or an amidase or endoglycanase having synthetic abilities, e.g., a mutant). Exemplary glycosytransferases are discussed below.

As used herein, the term "modified sugar," refers to a naturally- or non-naturally-occurring carbohydrate that is an enzymatic substrate in a process of the invention. The modified sugar is selected from a number of enzyme substrates including, but not limited to, modified nucleotide sugars, modified activated sugars, precursor modified sugars, and modified sugars that are neither activated nor nucleotides. The "modified sugar" is covalently functionalized with a "modifying group." Useful modifying groups include, for example, water-soluble polymers, therapeutic moieties, diagnostic moieties, biomolecules and the like. In some embodiments, the modifying group is not a naturally occurring, or an unmodified carbohydrate. The locus of functionalization with the modifying group is selected such that it does not prevent the "modified sugar" from being added enzymatically to a peptide. A modified sugar may contain any number of functional groups in addition to the modifying groups. For example, a modified sugar may contain one or more phosphate groups in addition to the modifying groups.

The term "modified activated sugar," as used herein, refers to modified sugars which have been synthetically altered to include an activated leaving group. As used herein, the term "activated leaving group" refers to those moieties that are easily displaced in enzyme-regulated nucleophilic substitution reactions. Many activated sugars are known in the art. See, for example, Vocadlo et al., In CARBOHYDRATE CHEMISTRY AND BIOLOGY, Vol. 2, Ernst et al. Ed., Wiley-VCH Verlag: Weinheim, Germany, 2000; Kodama et al., *Tetrahedron Lett.* 34: 6419 (1993); Lougheed, et al., *J. Biol. Chem.* 274: 37717 (1999)).

The term "modified nucleotide sugar" refers to a modified sugar covalently attached to a nucleoside via at least one phosphodiester linkage. Typically, the modified sugar is attached to a nucleoside via one or two phosphodiester linkages.

The term "precursor modified sugar" refers to a modified sugar that is capable of being exploited by a permissive biochemical pathway of the cell to effect conversion to an intermediate modified sugar. The permissive biochemical pathway typically involves phosphorylation or modification of the saccharide moiety. The intermediate modified sugar may be contacted with a nucleotidyl transferase and a nucleotide to form a modified nucleotide sugar and/or a glycosyltransferase for attachment to a peptide to form a peptide conjugate.

The term "homologous," as used herein, means a cellular component or molecule derived from the same cell, cell type or species.

The term "nucleotide" refers to a nucleoside having at least one phosphate group or phosphodiester linkage. Examples of nucleotides includes NMP-, NDP-, NTP- and NDP-sugar where N is a natural or non-natural nucleoside. A "nucleotidyl moiety" is a nucleotide attached to the remainder of a molecule through at least one phosphodiester linkage. For example, a nucleotidyl moiety may be attached to a sugar via a phosphodiester bond as shown in tables 3 and 4, below.

The term "water-soluble" refers to moieties that have some detectable degree of solubility in water. Methods to detect and/or quantify water solubility are well known in the art. Exemplary water-soluble polymers include peptides, saccharides, poly(ethers), poly(amines), poly(carboxylic acids) and the like. Peptides can have mixed sequences of be composed or a single amino acid, e.g. poly(lysine) or poly(glutamate). Similarly, saccharides can be of mixed sequence or composed of a single saccharide subunit, e.g., dextran, amylose, chitosan, and poly(sialic acid). An exemplary poly(ether) is poly (ethylene glycol). Poly(ethylene imine) is an exemplary polyamine, and poly(acrylic) acid is a representative poly (carboxylic acid).

"Poly(alkylene oxide)" refers to a genus of compounds having a polyether backbone. Poly(alkylene oxide) species of use in the present invention include, for example, straight- and branched-chain species. Moreover, exemplary poly(alkylene oxide) species can terminate in one or more reactive, activatable, or inert groups. For example, poly(ethylene glycol) is a poly(alkylene oxide) consisting of repeating ethylene oxide subunits, which may or may not include additional reactive, activatable or inert moieties at either terminus. Useful poly(alkylene oxide) species include those in which one terminus is "capped" by an inert group, e.g., monomethoxy-poly(alkylene oxide). When the molecule is a branched species, it may include multiple reactive, activatable or inert groups at the termini of the alkylene oxide chains and the reactive groups may be either the same or different. Derivatives of straight-chain poly(alkylene oxide) species that are heterobifunctional are also known in the art.

A "poly(ethylene glycol)" linker or modifying group refers to moieties having a poly(ethylene glycol) ("PEG") backbone or methoxy-PEG ("mPEG") backbone, including PEG and mPEG derivatives. A wide variety of PEG and mPEG derivatives are known in the art and are commercially available. For example, Nektar, Inc. Huntsville, Ala., provides PEG and mPEG compounds useful as linkers or modifying groups optionally having nucleophilic reactive groups, carboxyl reactive groups, eletrophilically activated groups (e.g. active esters, nitrophenyl carbonates, isocyanates, etc.), sulfhydryl selective groups (e.g. maleimide), and heterofunctional (having two reactive groups at both ends of the PEG or mPEG), biotin groups, vinyl reactive groups, silane groups, phospholipid groups, and the like.

The term, "glycosyl linking group," as used herein refers to a glycosyl residue to which an agent (e.g., water-soluble polymer, therapeutic moiety, biomolecule) is covalently attached. In the methods of the invention, the "glycosyl linking group" becomes covalently attached to a glycosylated or unglycosylated peptide, thereby linking the agent to an amino acid and/or glycosyl residue on the peptide. An exemplary "glycosyl linking group" is derived from a "modified nucleotide sugar" by the enzymatic attachment of the "modified sugar" portion of the "modified nucleotide sugar" to an amino acid and/or glycosyl residue of the peptide.

An "intact glycosyl linking group" refers to a glycosyl linking group in which the individual saccharide monomer that links the conjugate to the modifying group is not degraded (e.g., oxidized, e.g., by sodium metaperiodate). "Intact glycosyl linking groups" of the invention may be derived from a naturally occurring oligosaccharide by addition of glycosyl unit(s) or removal of one or more glycosyl unit from a parent saccharide structure. An exemplary "intact glycosyl linking group" includes at least one intact, e.g., non-degraded, saccharyl moiety that is covalently attached to an amino acid residue or glycosyl residue on a peptide. The remainder of the "linking group" can have substantially any structure. For example, the modifying group is optionally linked directly to the intact saccharyl moiety. Alternatively, the modifying group is linked to the intact saccharyl moiety via a linker arm. The linker arm can have substantially any structure determined to be useful in the selected embodiment. In an exemplary embodiment, the linker arm is one or more intact saccharyl moieties, i.e. "the intact glycosyl linking group" resembles an oligosaccharide. Another exemplary intact glycosyl linking group is one in which a saccharyl moiety attached, directly or indirectly, to the intact saccharyl moiety is degraded and derivatized (e.g., periodate oxidation followed by reductive amination). Still a further linker arm includes the modifying group attached to the intact saccharyl moiety, directly or indirectly, via a cross-linker, such as those described herein or analogues thereof.

"Degradation," as used herein refers to the removal of one or more carbon atoms or bonds from a saccharyl moiety.

As used herein, "therapeutic moiety" means any agent useful for therapy including, but not limited to, antibiotics, anti-inflammatory agents, anti-tumor drugs, cytotoxins, and radioactive agents. "Therapeutic moiety" includes prodrugs of bioactive agents, constructs in which more than one therapeutic moiety is bound to a carrier, e.g., multivalent agents. Therapeutic moiety also includes proteins, peptides and constructs that include proteins. Exemplary proteins include, but are not limited to, Erythropoietin (EPO), Granulocyte Colony Stimulating Factor (GCSF), Granulocyte Macrophage Colony Stimulating Factor (GMCSF), Interferon (e.g., Interferon-$\alpha$, -$\beta$, -$\gamma$), Interleukin (e.g., Interleukin II), serum proteins (e.g., Factors VII, VIIa, VIII, IX, and X), Human Chorionic Gonadotropin (HCG), Follicle Stimulating Hormone (FSH) and Lutenizing Hormone (LH) and antibody fusion proteins (e.g. Tumor Necrosis Factor Receptor (TNFR)/Fc domain fusion protein antibodies (FAbs).

As used herein, "anti-tumor drug" means any agent useful to combat cancer including, but not limited to, cytotoxins and agents such as antimetabolites, alkylating agents, anthracyclines, antibiotics, antimitotic agents, procarbazine, hydroxyurea, asparaginase, corticosteroids, interferons and radioactive agents. Also encompassed within the scope of the term "anti-tumor drug," are conjugates of peptides with anti-tumor activity, e.g. TNF-$\alpha$. Conjugates include, but are not limited to those formed between a therapeutic protein and a glycoprotein of the invention. A representative conjugate is that formed between PSGL-1 and TNF-$\alpha$.

The term "isolated" refers to a material that is substantially or essentially free from components, which are used to produce the material. For peptide conjugates of the invention, the term "isolated" refers to material that is substantially or essentially free from components, which normally accompany the material in the mixture used to prepare the peptide conjugate. "Isolated" and "pure" are used interchangeably. Typically, isolated peptide conjugates of the invention have a level of purity preferably expressed as a range. The lower end of the range of purity for the peptide conjugates is about 60%, about 70% or about 80% and the upper end of the range of purity is about 70%, about 80%, about 90% or more than about 90%.

When the peptide conjugates are more than about 90% pure, their purities are also preferably expressed as a range. The lower end of the range of purity is about 90%, about 92%, about 94%, about 96% or about 98%. The upper end of the range of purity is about 92%, about 94%, about 96%, about 98% or about 100% purity.

Purity is determined by any art-recognized method of analysis (e.g., band intensity on a silver stained gel, polyacrylamide gel electrophoresis, HPLC, or a similar means).

"Essentially each member of the population," as used herein, describes a characteristic of a population of peptide conjugates of the invention in which a selected percentage of the modified sugars added to a peptide are added to multiple, identical acceptor sites on the peptide. "Essentially each member of the population" speaks to the "homogeneity" of the sites on the peptide conjugated to a modified sugar and refers to conjugates of the invention, which are at least about 80%, preferably at least about 90% and more preferably at least about 95% homogenous.

"Homogeneity," refers to the structural consistency across a population of acceptor moieties to which the modified sugars are conjugated. Thus, in a peptide conjugate of the invention in which each modified sugar moiety is conjugated to an acceptor site having the same structure as the acceptor site to which every other modified sugar is conjugated, the peptide conjugate is said to be about 100% homogeneous. Homogeneity is typically expressed as a range. The lower end of the range of homogeneity for the peptide conjugates is about 60%, about 70% or about 80% and the upper end of the range of purity is about 70%, about 80%, about 90% or more than about 90%.

When the peptide conjugates are more than or equal to about 90% homogeneous, their homogeneity is also preferably expressed as a range. The lower end of the range of homogeneity is about 90%, about 92%, about 94%, about 96% or about 98%. The upper end of the range of purity is about 92%, about 94%, about 96%, about 98% or about 100% homogeneity. The purity of the peptide conjugates is typically determined by one or more methods known to those of skill in the art, e.g., liquid chromatography-mass spectrometry (LC-MS), matrix assisted laser desorption mass time of flight spectrometry (MALDITOF), capillary electrophoresis, and the like.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. Alkyl groups which are limited to hydrocarbon groups are termed "homoalkyl".

The term "alkylene" by itself or as part of another substituent means a divalent radical derived from an alkyl, as exemplified, but not limited, by —$CH_2CH_2CH_2CH_2$—. Likewise, the term "heteroalkylene" means a divalent radical derived from an heteroalkyl. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, P, Si and S, and wherein the nitrogen and sulfur atoms may optionally be oxidized and the nitrogen heteroatom may optionally be quaternized. The heteroatom(s) O, N, P and S and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, O—$CH_3$, —O—$CH_2$—$CH_3$, and —CN. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene," by themselves or as part of another substituent, means a divalent radical derived from a cycloalkyl or heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. The terms "arylene" and "heteroarylene," by themselves or as part of another substituent, means a divalent radical derived from a aryl or heteroaryl, respectively.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

The term "oxo" as used herein means an oxygen that is double bonded to a carbon atom.

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalcyl radicals (including those groups often referred to as alkylene, alkenyl, heteroalkylene, heteroalkenyl, alkynyl, cycloalkyl, heterocycloallkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2 m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: halogen, —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R'" and R"" are preferably independently selected from hydrogen, alkyl, heteroalkyl, aryl and heteroaryl. When a compound of the invention includes more than one R group, for example, each of the R groups is independently selected as are each R', R", R'" and R"" groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-($CH_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R'")$_d$—, where s and d are independently integers of from 0 to 3, and X' is —O—, —NR'—, —S—, —S(O)—, —S(O)$_2$—, or —S(O)$_2$NR'—. The substituents R, R', R" and R'" are preferably independently selected from hydrogen or substituted or unsubstituted ($C_1$-$C_6$)alkyl.

As used herein, the term "heteroatom" is meant to include oxygen (O), nitrogen (N), sulfur (S), phosphorus (P), and silicon (Si).

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention.

Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H, iodine-125 ($^{125}$I) or carbon-14 ($^{14}$C). All isotopic variations of the compounds of the present invention, whether radioactive or not, are encompassed within the scope of the present invention.

The terms "large-scale" and "industrial-scale" are used interchangeably and refer to a reaction cycle that produces at least about 250 mg of peptide conjugate. In an exemplary embodiment, the reaction cycle produces at least about 500 mg of peptide conjugate. In another exemplary embodiment, the reaction cycle produces at least about 1 gram of peptide conjugate.

Introduction

The invention provides methods of preparing conjugates of glycosylated and unglycosylated peptides. The conjugates are formed between peptides and diverse modifying group species such as water-soluble polymers, therapeutic moieties, toxins, peptides, diagnostic moieties, targeting moieties and the like. The conjugates of the invention are substantially formed intracellularly, generally using intracellular enzymatic components. Typically, a modified sugar is contacted and incubated with a cell under conditions in which the cell internalizes the modified sugar. The internalized modified sugar is then contacted by the cellular machinery.

Using the site specificity of intracellular enzyme components, such as glycosyltransferases, peptides bearing a desired group at one or more specific locations are generated. Thus, according to the present invention, a modified sugar is attached directly to a selected locus on the peptide chain or, alternatively, the modified sugar is appended onto a carbohydrate moiety of a glycopeptide. Peptides in which modified sugars are bound to both a glycopeptide carbohydrate and directly to an amino acid residue of the peptide backbone are also within the scope of the present invention. The modified sugar, when interposed between the peptide and the modifying group on the sugar becomes what is referred to herein as a "glycosyl linking group" (e.g., an intact glycosyl linking group).

The methods of the present invention include assembly of peptides and glycopeptides that have a substantially homogeneous derivatization pattern; the enzymes used in the invention are generally selective for a particular amino acid residue or combination of amino acid residues of the peptide.

The methods also include large-scale production of modified peptides and glycopeptides. Thus, the methods of the invention provide a practical means for large-scale preparation of glycopeptides having preselected uniform derivatization patterns. The methods are particularly well suited for modification of therapeutic peptides, including but not limited to, glycopeptides that are incompletely glycosylated during production in cell culture cells (e.g., mammalian cells, insect cells, plant cells, fungal cells, yeast cells, or prokaryotic cells) or transgenic plants or animals.

The methods of the invention also provide conjugates of glycosylated and unglycosylated peptides with increased therapeutic half-life due to, for example, reduced clearance rate, reduced rate of uptake by the immune or reticuloendothelial system (RES), or increased size. Moreover, the methods of the invention provide a means for masking antigenic determinants on peptides, thus reducing or eliminating a host immune response against the peptide. Selective attachment of targeting agents can also be used to target a peptide to a particular tissue or cell surface receptor that is specific for the particular targeting agent. Moreover, there is provided a class of peptides that are specifically modified with a therapeutic moiety.

1. Intracellular Methods of Forming a Peptide Conjugate

In a first aspect, the present invention provides methods of forming a peptide conjugate within a cell where the peptide conjugate includes a covalent linkage between a modifying group and a glycosylated or non-glycosylated peptide. The link between the peptide and the modifying group includes a glycosyl linking group (e.g., an intact glycosyl linking group) interposed between the peptide and the modifying group. Modifying groups are attached to one or more saccharide units, resulting in a "modified sugar" that is recognized by an appropriate intracellular enzyme.

The methods include the step of contacting a cell with a modified sugar having a sugar moiety and at least one modifying group. The modifying group is typically selected from a water-soluble polymer, a therapeutic moiety, a detectable label, a biomolecule and a targeting moiety.

The cell is incubated under conditions in which the cell internalizes the modified sugar. After incubation, the modified sugar is intracellularly contacted with a glycosylated or non-glycosylated peptide and a glycosyltransferase for which the modified sugar is a substrate resulting in the formation of a peptide conjugate.

Finally, the peptide conjugate may be isolated from the cell.

In some embodiments, the modified sugar is intracellularly contacted with intracellular enzymes other than a glycosyltransferase before attachment to a glycosylated or non-glycosylated peptide. For example, the modified sugar may be intracellularly contacted with a nucleotide and a nucleotidyl transferase resulting in the formation of a modified nucleotide sugar. The modified nucleotide sugar is then intracellularly contacted with a glycosylated or non-glycosylated peptide and a glycosyltransferase for which the modified nucleotide sugar is a substrate resulting in the formation of a peptide conjugate.

Alternatively, the modified sugar that is contacted with the cell is a modified nucleotide sugar having a sugar moiety and at least one modifying group. The modifying group is independently selected from a water-soluble polymer, a therapeutic moiety, a detectable label, a biomolecule and a targeting moiety. The cell is incubated under conditions in which the cell internalizes the modified nucleotide sugar. After incubation, the modified nucleotide sugar is intracellularly contacted with a glycosylated or non-glycosylated peptide and a glycosyltransferase for which the modified nucleotide sugar is a substrate to form the peptide conjugate. Finally, the peptide conjugate may be isolated.

In another embodiment, the modified sugar is a precursor modified sugar that is intracellularly converted to an intermediate modified sugar by cellular enzymes. In a related embodiment, the intermediate modified sugar is a phosphorylated modified sugar. The phosphorylated modified sugar is formed by intracellularly contacting the unphosphorylated modified sugar with a kinase for which the unphosphorylated modified sugar is a substrate. The phosphorylated modified nucleotide sugar is thereby formed.

In another embodiment, the modified sugar that is contacted with the cell is a modified activated sugar having a sugar moiety and at least one modifying group. The modifying group is independently selected from a water-soluble polymer, a therapeutic moiety, a detectable label, a biomolecule and a targeting moiety. The cell is incubated under conditions in which the cell internalizes the modified activated sugar. After incubation, the modified activated sugar is intracellularly contacted with a glycosylated or non-glycosylated peptide and a glycosyltransferase for which the modified activated sugar is a substrate to form the peptide conjugate. Finally, the peptide conjugate may be isolated.

Modified activated sugars are modified sugars which have been synthetically altered to include an activated leaving group. As used herein, the term "activated leaving group" refers to those moieties that are easily displaced in enzyme-regulated nucleophilic substitution reactions. Examples of activating leaving groups include fluoro, chloro, bromo, tosylate ester, mesylate ester, triflate ester and the like. Preferred activated leaving groups, for use in the present invention, are those that do not significantly sterically encumber the enzymatic transfer of the glycoside to the acceptor.

Accordingly, exemplary modified activated sugars include glycosyl fluorides and glycosyl mesylates. Among the glycosyl fluorides, α-galactosyl fluoride, α-mannosyl fluoride, α-glucosyl fluoride, α-fucosyl fluoride, α-xylosyl fluoride, α-sialyl fluoride, α-N-acetylglucosaminyl fluoride, α-N-acetylgalactosaminyl fluoride, β-galactosyl fluoride, β-mannosyl fluoride, β-glucosyl fluoride, β-fucosyl fluoride, β-xylosyl fluoride, β-sialyl fluoride, β-N-acetylglucosaminyl fluoride and β-N-acetylgalactosaminyl fluoride are particularly useful.

By way of illustration, glycosyl fluorides can be prepared from the free sugar by first acetylating the sugar and then treating it with HF/pyridine. This generates the thermodynamically most stable anomer of the protected (acetylated) glycosyl fluoride (i.e., the α-glycosyl fluoride). If the less stable anomer (i.e., the β-glycosyl fluoride) is desired, it can be prepared by converting the peracetylated sugar with HBr/HOAc or with HCl to generate the anomeric bromide or chloride. This intermediate is reacted with a fluoride salt such as silver fluoride to generate the glycosyl fluoride. Acetylated glycosyl fluorides may be deprotected by reaction with mild (catalytic) base in methanol (e.g. NaOMe/MeOH). In addition, many glycosyl fluorides are commercially available.

Other activated glycosyl derivatives can be prepared using conventional methods known to those of skill in the art. For example, glycosyl mesylates can be prepared by treatment of the fully benzylated hemiacetal form of the sugar with mesyl chloride, followed by catalytic hydrogenation to remove the benzyl groups.

The intracellular enzymes used in the present invention may be recombinant enzymes, which can be expressed at a variety of time points. For example, the recombinant enzyme may be expressed concurrently with the expression of the glycosylated or non-glycosylated peptide of the invention. Alternatively, the recombinant enzyme is a recombinant nucleotidyl transferase expressed concurrently with the expression of the glycosylated or non-glycosylated peptide. The recombinant enzyme may also be a recombinant glycosyltransferase expressed concurrently with the expression of the glycosylated or non-glycosylated peptide. In addition, the recombinant enzyme may be a recombinant kinase expressed concurrently with the expression of the glycosylated or non-glycosylated peptide.

A. Contacting a Modified Sugar with a Cell

In one embodiment, the methods of the present invention comprise contacting a cell with a modified sugar and incubating the cell under conditions in which the cell internalizes the modified sugar. Modified sugars internalized by the cell are then intracellularly contacted with enzymes to form the peptide conjugates. Methods of intracellularly contacting the internalized modified sugar with enzymes to form the peptide conjugates are described below. This section focuses on methods of cellular internalization of the modified sugar.

The modified sugar may be a modified nucleotide sugar, which is contacted with a cell and incubated under conditions in which the cell internalizes the modified nucleotide sugar. Modified nucleotide sugars internalized by the cell are then intracellularly contacted with enzymes to form the peptide conjugates.

The modified sugar may also be a modified activated sugar. The modified activated sugar may be contacted with a cell and incubated under conditions in which the cell internalizes the modified activated sugar. Modified activated sugar internalized by the cell are then intracellularly contacted with enzymes to form the peptide conjugates.

A wide variety of methodologies and conditions are useful for cellular internalization of the modified sugar. In one embodiment, the modified sugar is contacted with the cell and internalized by a cellular molecular uptake mechanism. In an exemplary embodiment, a modified sugar is a modified sialic acid that is added to a eukaryotic cell culture. Using a sialic acid molecular uptake mechanism, the eukaryotic cell actively internalizes the modified sialic acid. In another exemplary embodiment, a modified sialic acid is added to a prokaryotic cell, which actively internalizes the modified sialic acid. A variety of molecular uptake mechanisms for modified sugars are useful in the current invention, such as those described in Oetke et al., *J. Biol. Chem.*, 277:6688-6695 (2002) and Hills et al., *American Biotechnology Laboratory*, 20:30 (2002).

In another embodiment, the internalization of modified sugar is enhanced by a suitable method. Methods useful in enhancing internalization of modified sugars are described in U.S. patent application Ser. No. 10/287,994, which is commonly owned by the same assignee and herein incorporated by reference in its entirety for all purposes. In an exemplary embodiment, cellular internalization of the modified sugar is enhanced with the use of permeabilizing agents. Permeabilizing agents useful in the current invention include detergents, solvents, zwitterionic reagents, lipids and proteins. In another exemplary embodiment, cellular internalization of the modified sugar is enhanced using mechanical methods such as oxygen sparging, gas sparging, mixing, temperature variations, freeze-thaw, sonication, electroporation, microinjection and microwaves. In another exemplary embodiment, cellular internalization of the modified sugar is enhanced using liposomes to deliver the modified sugar to the cell.

The modifying group of the modified sugar can be in a masked, latent, inchoate or nascent form. Masking groups may be liberated in any convenient way. In an exemplary embodiment, ketal or enols may be converted to corresponding ketones by low pH facilitated hydrolysis. Alternatively, many specific enzymes are known to cleave specific protecting groups, thereby unmasking the modifying group of the modified sugar.

The modified sugar may be contacted with the cell at a variety of time points. For example, the modified sugar may be contacted with the cell before inducing the expression of the glycosylated or non-glycosylated peptide. Alternatively, the modified sugar is contacted with the cell after inducing the expression of the glycosylated or non-glycosylated peptide. The modified sugar may also be contacted with the cell while inducing the expression of the glycosylated or non-glycosylated peptide. In another exemplary embodiment, the modified sugar is added during the cellular growth phase.

A variety of cells are useful in the methods of the current invention. Cells are typically chosen that are capable of internalizing the modified sugar using one of the methods described above. Cells may be in culture, such as immortalized or primary cultures, or in situ, such as organism resident cells.

Cells may be screened for their ability to internalize a modified sugar. A variety of methods may be used to screen for cells capable of internalizing modified sugars. In an exemplary embodiment, internalization of the modified sugar is evaluated by lysing the cell, isolating the modified sugar and quantitating the modified sugar. Exemplary isolation methods include affinity chromatography, thin or thick layer chromatography, size exclusion chromatography, ion exchange chromatography, electrophoresis, dialysis or membrane filtration. Exemplary quantitation methods include light absorbance, fluorescence emission, phosphorescence emission, mass spectrometry, protein binding assays (e.g. ELISA), and the like.

Cells useful in the current invention include prokaryotic and eukaryotic cells, including mammalian, insect, bacterial, fungal, and yeast cells. See Section 8 below.

B. Intracellularly Contacting Modified Nucleotide Sugar with a Glycosyltransferase In another exemplary embodiment, the method of the present invention includes intracellularly contacting a modified nucleotide sugar with a glycosylated or non-glycosylated peptide and a glycosyltransferase, trans-sialidase, or an amidase or endoglycanase having synthetic abilities, e.g., a mutant.

Intracellular glycosyltransferases catalyze the transfer of the modified sugar moiety to a glycosylated or non-glycosylated peptide to form a peptide conjugate. The peptide conjugate comprises a modifying group conjugated to the peptide via a glycosyl linking group between and covalently linked to both the peptide and the modifying group.

The modified sugars are intracellularly conjugated to a glycosylated or non-glycosylated peptide using an appropriate intracellular glycosyltransferase to mediate the conjugation. A number of methods of using glycosyltransferases to synthesize desired oligosaccharide structures are known and are generally applicable to the intracellular methods of the instant invention. Exemplary methods are described, for instance, WO 96/32491, Ito et al., *Pure Appl. Chem.* 65: 753 (1993), and U.S. Pat. Nos. 5,352,670, 5,374,541, and 5,545, 553, which are herein incorporated by reference in their entirety for all purposes.

Exemplary attachment points for modified sugars onto the peptide include, but are not limited to: (a) consensus sites for N-linked glycosylation and O-linked glycosylation; (b) terminal glycosyl moieties that are acceptors for a glycosyltransferase; (c) arginine, asparagine and histidine; (d) free carboxyl groups; (e) free sulfhydryl groups such as those of cysteine; (f) free hydroxyl groups such as those of serine, threonine, or hydroxyproline; (g) aromatic residues such as those of phenylalanine, tyrosine, or tryptophan; or (h) the amide group of glutamine. Exemplary methods of use in the present invention are described in WO 87/05330 published Sep. 11, 1987, and in Aplin and Wriston, CRC CRIT. REV. BIOCHEM., pp. 259-306 (1981).

In an exemplary embodiment, a glycosyltransferase transfers a modified sugar to a glycan structure attached to the peptide. Thus, the peptide is conjugated to the modifying group via a glycosyl linking group at the end of, or within, the glycan structure of the peptide.

The modified sugar may be added to the growing glycan structure of the peptide by a glycosyltransferase. The resulting peptide contains modified sugar at an internal position of the glycan structure. In an exemplary embodiment, an intracellular galactosyltransferase may catalyze the transfer of Gal-PEG from UDP-Gal-PEG onto the glycan, followed by addition of a sialic acid using intracellular ST3Gal3 and CMP-SA, which serves to add a "capping" unmodified sialic acid onto the glycan. Alternatively, the sialic acid may be added in vitro.

In another exemplary embodiment, at least two different modified sugars are intracellularly added to the glycan (or amino acid residue) structures on the peptide. In this manner, two or more different glycoconjugates may be added to one or more glycan on a peptide. This process generates glycan structures having two or more functionally different modified sugars. In an exemplary embodiment, intracellularly contacting the peptide with GnT-I,II and UDP-GlcNAc-PEG serves to add a GlcNAc-PEG molecule to the glycan; contact with intracellularly galactosyltransferase and UDP-Gal then serves to add a Gal residue thereto; and, contact with intracellularly ST3Gal3 and CMP-SA modified with a therapeutic moiety serves to add a SA modified with a therapeutic moiety to the glycan. This series of intracellularly reactions results in a glycan chain having the functional characteristics of a PEGylated glycan as well as the therapeutic moiety targeting activity. alternatively, the steps of adding sugars to the peptide conjugate may be performed in vitro.

In the discussion that follows, the invention is exemplified by the conjugation of modified sialic acid moieties to a glycosylated peptide within a cell. The exemplary modified sialic acid is labeled with PEG. The focus of the following discussion on the use of PEG-modified sialic acid and glycosylated peptides is for clarity of illustration and is not intended to imply that the invention is limited to the conjugation of these two partners. One of skill understands that the discussion is generally applicable to the additions of modified glycosyl moieties other than sialic acid. Moreover, the discussion is equally applicable to the modification of a glycosyl unit with any applicable modifying moiety, including water-soluble polymers, water-insoluble polymers, therapeutic moieties, and biomolecules.

An intracellular enzymatic approach is used for the selective introduction of a modified sugar onto a peptide or glycopeptide. The method utilizes modified sugars combined with the appropriate intracellular glycosyltransferase. By selecting the glycosyltransferase that will make the desired carbohydrate linkage and utilizing the modified sugar as the donor substrate, the modifying group can be introduced directly onto the peptide backbone, onto existing sugar residues of a glycopeptide, or onto sugar residues that have been added to a peptide.

An acceptor for the glycosyltransferase is present on the peptide to be modified by the methods of the present invention either as a naturally occurring structure or one placed there recombinantly, enzymatically or chemically. Suitable acceptors, include, for example, galactosyl acceptors of sialyltransferases, such as Galβ1,4GlcNAc, Galβ1,4GalNAc, Galβ1,3GalNAc, lacto-N-tetraose, Galβ1,3GlcNAc, Galβ1,3Ara, Galβ1,6GlcNAc, Galβ1,4Glc (lactose), and other acceptors known to those of skill in the art (see, e.g., Paulson et al., *J. Biol. Chem.* 253: 5617-5624 (1978)).

In an exemplary embodiment, a peptide or glycopeptide is labeled with galactose residues, or an oligosaccharide residue that terminates in a galactose unit. Following the exposure of or addition of the galactose residues, an appropriate intracellular sialyl transferase adds a modified sialic acid. The approach is summarized in Scheme 1.

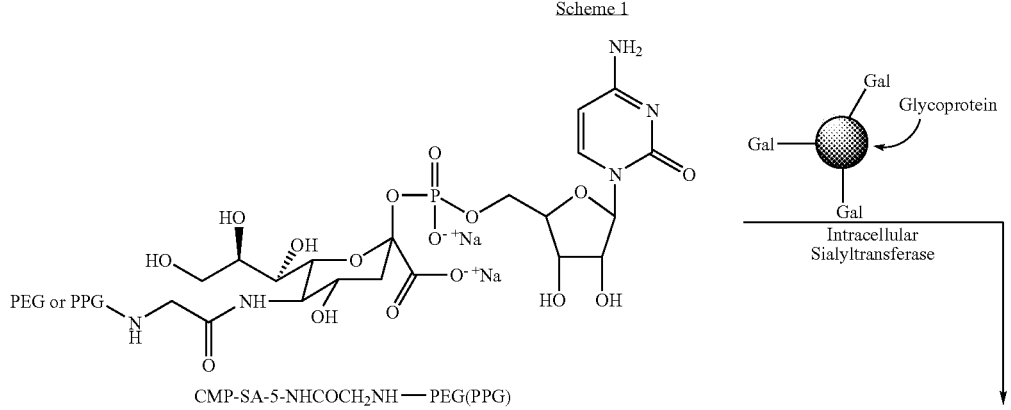

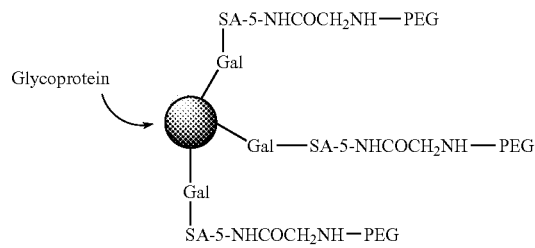

In another embodiment, the modified sugar is added directly to a free amino or hydroxyl group on the peptide backbone. Typically, the amino or hydroxyl group forms part of an amino acid side chain (e.g. serine, threonine, tyrosine and arginine). An exemplary embodiment is set forth in Scheme 2.

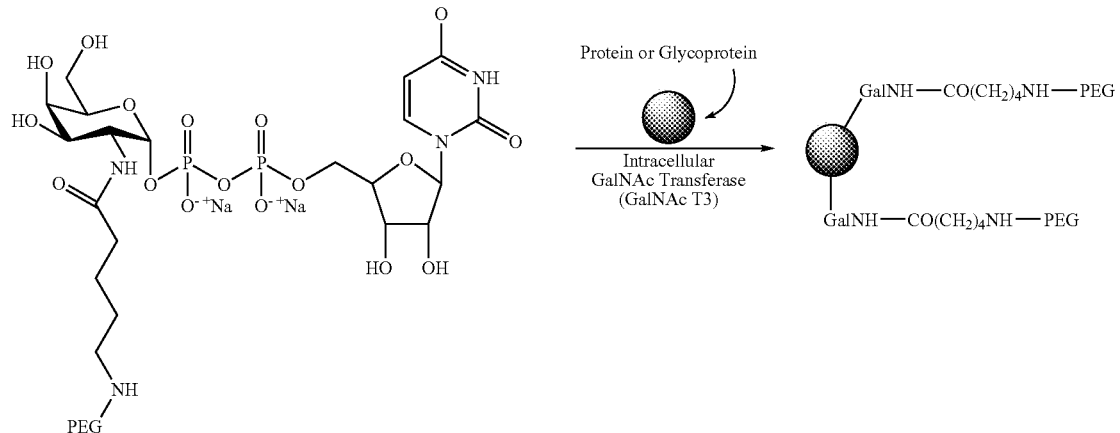

Scheme 2

In yet a further approach, summarized in Scheme 3, a masked reactive functionality is present on a modified sialic acid. The masked reactive group is preferably unaffected under cellular conditions. After the intracellular covalent attachment of the modified sialic acid to the peptide, the peptide conjugate is isolated from the cell and the mask is removed. The peptide may then be conjugated with any appropriate additional modifying group, such as water-soluble polymer, a water-insoluble polymer, a therapeutic moiety, a detectable label, and a biomolecule. The modifying group is conjugated to the peptide in a specific manner by its reaction with the unmasked reactive group on the modified sugar residue. This process is typically used where the modifying group is an antibody or toxin.

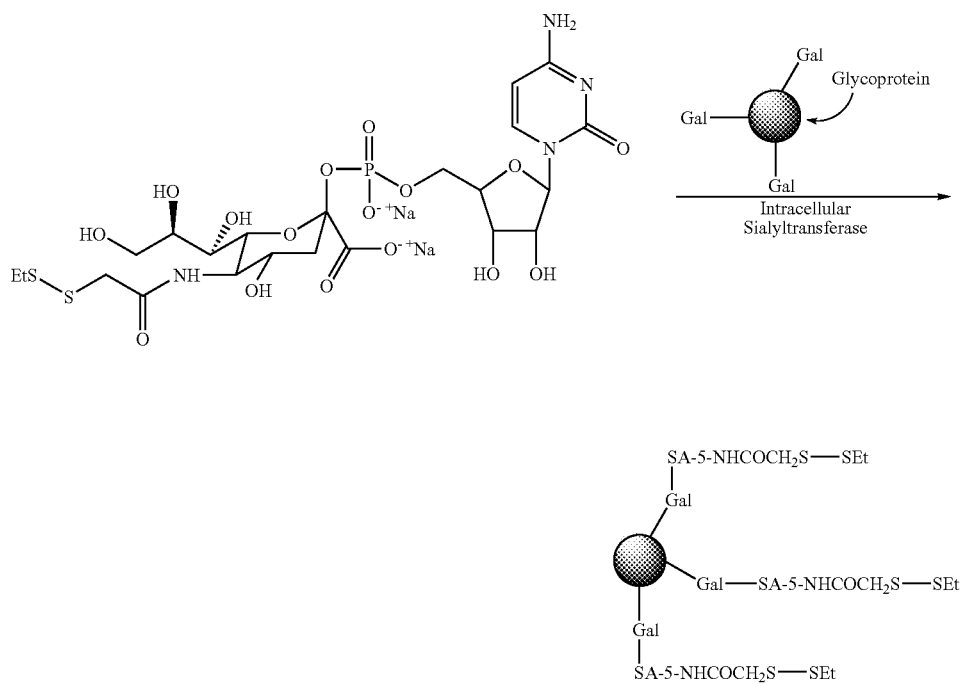

Scheme 3

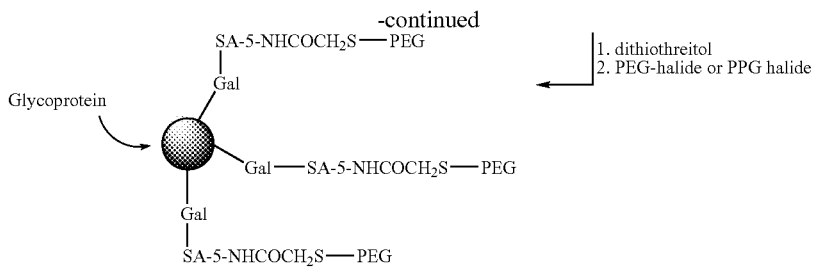

One of skill in the art will immediately recognize that any modified sugar can be used with its appropriate glycosyltransferase, depending on the terminal sugars of the oligosaccharide side chains of the glycopeptide.

Exemplary intracellular glycosyltransferases useful in practicing the present invention include, but are not limited to, GalNAc transferases (GalNAc T1-14), GlcNAc transferases, fucosyltransferases, glycosyltransferases, xylosyltransferases, mannosyltransferases and the like. See Section 9 below. Use of this approach allows the direct addition of modified sugars onto peptides that lack any carbohydrates or, alternatively, onto existing glycopeptides. In both cases, the addition of the modified sugar occurs at specific positions on the peptide backbone as defined by the substrate specificity of the glycosyltransferase and not in a random manner as occurs during modification of a protein's peptide backbone using chemical methods. An array of modifying groups can be introduced into proteins or glycopeptides that lack the glycosyltransferase substrate peptide sequence by engineering the appropriate amino acid sequence into the peptide chain. Glycosyltransferases of use in the methods of the current invention, along with their donor and acceptor substrates, are also discussed in detail in U.S. patent application Ser. No. 10/287, 994 and U.S. Patent Application Publication No. 20040063911, which are commonly owned by the same assignee and herein incorporated by reference in its entirety for all purposes.

In each of the exemplary embodiments set forth above, one or more additional enzymatic modification steps can be utilized, either in vitro or intracellularly, following the conjugation of the modified sugar to the peptide. In an exemplary embodiment, an enzyme (e.g., fucosyltransferase) is used to append a glycosyl unit (e.g., fucose) onto the terminal modified sugar attached to the peptide. In another example, an enzymatic reaction is utilized to "cap" sites to which the modified sugar failed to conjugate. One of skill will appreciate that there is an array of enzymatic procedures that are useful in the methods of the invention at a stage after the modified sugar is conjugated to the peptide both in vitro and intracellularly. Further elaboration of the modified sugar-peptide conjugate is within the scope of the invention.

A variety of glycosylated and non-glycosylated peptides are useful in conjunction with the current invention. Exemplary peptides are discussed below in Section 6.

C. Formation of Modified Nucleotide Sugars

In another embodiment, the methods of the present invention comprise contacting a modified sugar with a nucleotide and a nucleotidyl transferase to form a modified nucleotide sugar. Nucleotidyl transferases catalyze the reaction between modified sugars and nucleotides to form modified nucleotide sugars. The formation of a modified nucleotide sugar may be performed in vitro or intracellularly.

In an exemplary embodiment, the modified sugar is contacted in vitro with a nucleotidyl transferase and a nucleotide to form a modified nucleotide sugar. The modified nucleotide sugar is then contacted with a cell and incubated under conditions in which the cell internalizes the modified nucleotide sugar. The internalized modified nucleotide sugar is then intracellularly contacted with a glycosyltransferase and a glycosylated or non-glycosylated peptide to form a peptide conjugate.

In another exemplary embodiment, the modified sugar is contacted intracellularly with a nucleotidyl transferase and a nucleotide to from a modified nucleotide sugar. The modified nucleotide sugar is then intracellularly contacted with a glycosyltransferase and a glycosylated or non-glycosylated peptide to form a peptide conjugate.

Modified sugars useful in the methods of the present invention may include a phosphate, or a phospho-mono-, di- or tri-ester moiety. In an exemplary embodiment, a modified sugar containing a phosphate moiety is intracellularly contacted with a nucleotide and a nucleotidyl transferase to form a modified nucleotide sugar.

A variety of methods are used to form modified sugars comprising a phosphate group (hereinafter referred to as "phosphorylated modified sugars"). In one embodiment, the phosphorylated modified sugars are formed in vitro. In an exemplary embodiment, a kinase is selected for which the unphosphorylated modified sugar is a substrate. The kinase is contacted with the unphosphorylated modified sugar and a nucleotide under conditions in which the unphosphorylated modified sugar is phosphorylated.

In an exemplary embodiment, unphosphorylated modified galactose is contacted with galactose kinase and ATP to form phosphorylated modified galactose. The phosphorylated modified galactose is then contacted with a cell and incubated under conditions in which the cell internalizes the modified sugar. The phosphorylated modified galactose (a modified sugar) is then intracellularly contacted with UDP-Galactose uridyltransferase (a nucleotidyl transferase) and UDP-glucose (a nucleotide) to form modified-UDP-galactose (a modified nucleotide sugar). The resulting modified-UDP-galactose is then intracellularly contacted with a glycosylated or non-glycosylated peptide and the appropriate galactosyltransferase to form a peptide conjugate.

In another embodiment, the phosphorylated modified sugars are formed intracellularly. In an exemplary embodiment, the unphosphorylated modified sugar is intracellularly contacted with the appropriate intracellular kinase and a first nucleotide to form the corresponding phosphorylated modified sugar. The phosphorylated modified sugar is then intracellularly contacted with the appropriate nucleotidyl transferase and nucleotide to form the modified nucleotide sugar. The resulting modified nucleotide sugar is then intracellularly contacted with a glycosylated or non-glycosylated peptide and the appropriate galactosyltransferase to form a peptide conjugate.

Any suitable combination of nucleotide and nucleotidyl transferases may be used in conjunction with the current methods of the invention. Typically, the choice of nucleotide and nucleotidyl transferase will depend upon the identity of the modified sugar. In an exemplary embodiment, the combination of nucleotide and nucleotidyl transferase is chosen in accordance with Table 1. However, one of skill will recognize that a variety of other combinations are useful in the methods of the current invention.

TABLE 1

| MODIFIED SUGAR | NUCLEOTIDYL TRANSFERASE | NUCLEOTIDE | MODIFIED NUCLEOTIDE SUGAR PRODUCT |
| --- | --- | --- | --- |
| Modified N-acylneuraminate | Acylneuraminate cytidylyltransferase | CTP | Modified CMP-N-acylneuraminate |
| Modified D-glucose 1-phosphate | Glucose-1-phosphate cytidylyltransferase | CTP | Modified CDP-glucose |
| Modified alpha-D-galactose 1-phosphate | Galactose-1-phosphate thymidylyltransferase | dTTP | Modified dTDP-galactose |
| Modified alpha-D-glucose 1-phosphate | Glucose-1-phosphate guanylyltransferase | GTP | Modified GDP-glucose |
| Modified L-fucose 1-phosphate | Fucose-1-phosphate guanylyltransferase | GTP | Modified GDP-L-fucose |
| Modified alpha-D-hexose 1-phosphate | Hexose-1-phosphate guanylyltransferase | GTP | Modified GDP-hexose |
| Modified hexose 1-phosphate | Nucleoside-triphosphate-hexose-1-phosphate nucleotidyltransferase | Nucleoside triphosphate | Modified NDP-hexose |
| Modified alpha-D-glucose 1-phosphate | Glucose-1-phosphate adenylyltransferase | ATP | Modified ADP-glucose |
| Modified alpha-D-glucose 1-phosphate | Glucose-1-phosphate thymidylyltransferase | dTTP | Modified dTDP-glucose |
| Modified N-acetyl-alpha-D-glucosamine 1-phosphate | UDP-N-acetylglucosamine pyrophosphorylase | UTP | Modified UDP-N-acetyl-D-glucosamine |
| Modified D-mannose 1-phosphate | Mannose-1-phosphate guanylyltransferase (GDP) | GDP | Modified GDP-mannose |
| Modified alpha-D-mannose 1-phosphate | Mannose-1-phosphate guanylyltransferase | GTP | Modified GDP-mannose |
| Modified alpha-D-glucose 1-phosphate | Glucose-1-phosphate uridylyltransferase | UTP | Modified UDP-glucose |
| Modified alpha-D-galactose 1-phosphate | Galactose-1-Phosphate Uridylyl Transferase | UTP or Alpha-D-glucose 1-phosphate | Modified UDP-galactose |
| Modified alpha-D-xylose 1-phosphate | Xylose-1-phosphate uridylyltransferase | UTP | Modified UDP-D-xylose |
| Modified alpha-D-galactose 1-phosphate | Hexose-1-phosphate uridylyltransferase | UDP-glucose | Modified UDP-galactose |
| Modified 1-phospho-alpha-D-glucuronate | Glucuronate-1-phosphate uridylytransferase | UTP | Modified UDP-D-glucuronate |
| Modified D-ribitol 5-phosphate | D-ribitol-5-phosphate cytidylyltransferase | CTP | Modified CDP-ribitol |
| Modified glycerol 3-phosphate | Glycerol-3-phosphate cytidylyltransferase | CTP | Modified CDP-glycerol |
| Modified 3-deoxy-D-manno-octulosonate | 3-deoxy-manno-octulosonate cytidylyltransferase | CTP | Modified CMP-3-deoxy-D-manno-octulosonate |
| Modified aldose 1-phosphate | Aldose-1-phosphate nucleotidyltransferase | NDP | Modified NDP-aldose |
| Modified aldose 1-phosphate | Aldose-1-phosphate adenylyltransferase | ADP | Modified ADP-aldose |
| Modified D-ribose 5-phosphate | Ribose-5-phosphate adenylyltransferase | ADP | Modified ADP-ribose |

Nucleotidyl transferases may be expressed in the cell and catalyze the nucleotidyl transfer intracellularly. In one embodiment, the nucleotidyl transferase is homologous to the cell. In another embodiment, the nucleotidyl transferase is heterologous to the cell. In an exemplary embodiment, the cell is transformed with the DNA encoding a functional nucleotidyl transferase using known methods (See Molecular Cloning: A Laboratory Manual (2001) Cold Spring Harbor Laboratory, New York).

In another embodiment, the modified sugar that is contacted and internalized undergoes intracellular modifications prior to intracellular contact with nucleotidyl transferase. The modified sugar is typically a precursor modified sugar selected to exploit a permissive biochemical pathway of the cell to effect conversion of the precursor modified sugar to an intermediate modified sugar. In an exemplary embodiment, the precursor modified sugar is contacted with the cell and incubated under conditions in which the cell internalizes the precursor modified sugar. Next, the precursor modified sugar is converted to an intermediate modified sugar by cellular enzymes. The intermediate modified sugar is then intracellularly contacted with a nucleotidyl transferase and a nucleotide to form the modified nucleotide sugar. The modified nucleotide sugar is then intracellularly contacted with a glycosyltransferase and a peptide to form the peptide conjugate.

In another exemplary embodiment, the precursor modified sugar is a modified-mannosamine (e.g. a mannosamine-PEG). The modified-mannosamine is contacted and incubated with a cell under conditions in which the cell internalizes the modified-mannosamine. Intracellular enzymes convert the modified-mannosamine to a modified-sialic acid, which is subsequently intracellularly contacted with CTP and CMP-SA-synthetase to form modified-nucleotide-CMP-SA. The modified-nucleotide-CMP-SA is then intracellularly contacted with the appropriate sialyl transferase and glycosylated or non-glycosylated peptide to form the peptide conjugate.

In another embodiment, a nucleotidyl transferase is used in conjunction with chemical methods in vitro to form the modified nucleotide sugar. In an exemplary embodiment, the methods illustrated in Schemes 5-12 are modified to include a step wherein a modified sugar is contacted with the appropriate nucleotidyl transferase and nucleotide to from a modified nucleotide sugar intermediate. Methods useful in forming modified nucleotide sugar intermediates in vitro are discussed in U.S. patent application Ser. No. 10/287,994, which is commonly owned by the same assignee and herein incorporated by reference in its entirety for all purposes. In an exemplary embodiment, a modified nucleotide sugar formed in vitro is contacted with the cell under conditions in which the cell internalizes the modified nucleotide sugar. The modified nucleotide sugar is then intracellularly contacted with a glycosyltransferase and a glycosylated or non-glycosylated peptide to from a peptide conjugate.

D. Isolation of the Peptide Conjugate

In another embodiment, the methods of the present invention include isolating the peptide conjugate from the cell. A variety of methods are useful in isolating the peptide conjugates of the current invention.

In an exemplary embodiment, the peptide conjugate is isolated from the cell by lysing the cell and purifying the peptide conjugate using standard techniques known in the art. Techniques useful in the current invention include ultrafiltration, size exclusion chromatography, ion exchange chromatography, membrane filtration, reverse osmosis (see, e.g., WO 98/15581), electrophoresis, dialysis, and the like.

The peptide conjugates may also be secreted from a cell or cell culture and collected from the extracellular spaces. Typically, the peptide conjugate contains a secretory signal sequence capable of facilitating secretion from the cell. In an exemplary embodiment, the secretory sequence is engineered into a recombinant peptide to from a secretable peptide. A modified sugar is then transferred to the secretable peptide using the methods of the invention to form a secretable peptide conjugate. The secreted peptide conjugate can be harvested and purified from the extracellular spaces by any conventional means.

In some embodiments, where the peptide conjugate is produced intracellularly or secreted, as a first step, the particulate debris, either host cells, lysed fragments, is removed, for example, by centrifugation or ultrafiltration; optionally, the peptide conjugate may be concentrated with a commercially available protein concentration filter, followed by separating the peptide variant from other impurities by one or more steps selected from immunoaffinity chromatography, ion-exchange column fractionation (e.g. on diethylaminoethyl (DEAE) or matrices containing carboxymethyl or sulfopropyl groups), chromatography on Blue-Sepharose, CM Blue-Sepharose, MONO-Q, MONO-S, lentil lectin-Sepharose, WGA-Sepharose, Con A-Sepharose, Ether Toyopearl, Butyl Toyopearl, Phenyl Toyopearl, or protein A Sepharose, SDS-PAGE chromatography, silica chromatography, chromatofocusing, reverse phase HPLC (RP-HPLC), gel filtration using, e.g., Sephadex molecular sieve or size-exclusion chromatography, chromatography on columns that selectively bind the peptide, and ethanol, pH or ammonium sulfate precipitation, membrane filtration and various techniques.

Peptide conjugates produced in culture are usually isolated by initial extraction from cells, enzymes, etc., followed by one or more concentration, salting-out, aqueous ion-exchange, or size-exclusion chromatography steps. Additionally, the peptide conjugate may be purified by affinity chromatography. Then, HPLC may be employed for final purification steps.

A protease inhibitor, e.g., phenylmethylsulfonylfluoride (PMSF) may be included in any of the foregoing steps to inhibit proteolysis and antibiotics may be included to prevent the growth of adventitious contaminants.

Within another embodiment, supernatants from systems which produce the peptide conjugate of the invention are first concentrated using a commercially available protein concentration filter, for example, an Amicon or Millipore Pellicon ultrafiltration unit. Following the concentration step, the concentrate may be applied to a suitable purification matrix. For example, a suitable affinity matrix may comprise a ligand for the peptide conjugate, a lectin or antibody molecule bound to a suitable support. Alternatively, an anion-exchange resin may be employed, for example, a matrix or substrate having pendant DEAE groups. Suitable matrices include acrylamide, agarose, dextran, cellulose, or other types commonly employed in protein purification. Alternatively, a cation-exchange step may be employed. Suitable cation exchangers include various insoluble matrices comprising sulfopropyl or carboxymethyl groups. Sulfopropyl groups are particularly preferred.

Then, one or more RP-HPLC steps employing hydrophobic RP-HPLC media, e.g., silica gel having pendant methyl or other aliphatic groups, may be employed to further purify the peptide conjugate. Some or all of the foregoing purification steps, in various combinations, can also be employed to provide a homogeneous modified glycoprotein.

The peptide conjugate of the invention resulting from a large-scale fermentation may be purified by methods analogous to those disclosed by Urdal et al., *J. Chromatog.* 296: 171 (1984). This reference describes two sequential, RP-HPLC steps for purification of recombinant human IL-2 on a preparative HPLC column. Alternatively, techniques such as affinity chromatography may be utilized to purify the modified glycoprotein.

The present invention provides for the industrial-scale production of peptide conjugates. In an exemplary embodiment, the industrial scale produces at least about 250 mg of finished, purified peptide conjugate. In another exemplary embodiment, the industrial scale produces at least about 500 mg of finished, purified peptide conjugate. In yet another exemplary embodiment, the industrial scale produces at least about 250 mg of finished, purified peptide conjugate. In some embodiments, industrial scale production of purified conjugate is obtained from a single batch of cells in which the conjugates are formed. Thus, the methods of isolating peptide conjugates discussed above are applicable to industrial-scale production.

2. Modified Sugars

The modified sugars of the present invention may be any naturally or non-naturally occurring carbohydrate that is an enzymatic substrate in a process of the present invention.

In an exemplary embodiment, the modified sugar has the formula

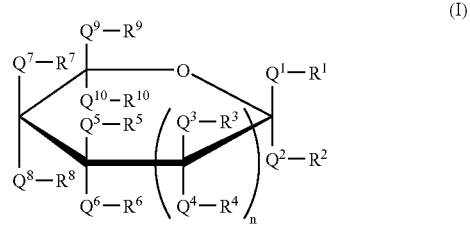

(I)

In Formula (I), the symbol n represents an integer from 0 to 1. Thus, the modified sugar of Formula (I) may be a five membered ring or a six membered ring. In a related embodiment, n is 1.

$Q^1$, $Q^2$, $Q^3$, $Q^4$, $Q^5$, $Q^6$, $Q^7$, $Q^8$, $Q^9$, and $Q^{10}$ are independently selected from a bond, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, —O—, —N($R^{14}$)—, —S—, —C(O)—, and —$CH_2$—. $R^{14}$ is selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, and a modifying group. Appropriate modifying groups are described below.

$R^1$, $R^2$, $R^3$, $R^4$, $R^5$, $R^6$, $R^7$, $R^8$, $R^9$, and $R^{10}$ are independently selected from —$PO_3$, hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, an activated leaving group, a nucleotidyl moiety, and a modifying group. At least one of $R^1$, $R^2$, $R^3$, $R^4$, $R^5$, $R^6$, $R^7$, $R^8$, $R^9$, and $R^{10}$ is a modifying group. Appropriate modifying groups are discussed below.

Where the modified sugar is a nucleotide modified sugar, at least one of $R^1$, $R^2$, $R^3$, $R^4$, $R^5$, $R^6$, $R^7$, $R^8$, $R^9$, and $R^{10}$ is a modifying group and/or a nucleotidyl moiety. Where the modified sugar is an activated modified sugar, at least one of $R^1$, $R^2$, $R^3$, $R^4$, $R^5$, $R^6$, $R^7$, $R^8$, $R^9$, and $R^{10}$ is a modifying group and/or an activated leaving group.

In an exemplary embodiment, $Q^1$, $Q^2$, $Q^3$, $Q^4$, $Q^5$, $Q^6$, $Q^7$, $Q^8$, $Q^9$, and $Q^{10}$ are independently selected from a bond, substituted or unsubstituted $C_1$-$C_{10}$) alkylene, substituted or unsubstituted 2 to 10 membered heteroalkylene, substituted or unsubstituted $C_5$-$C_7$ cycloalkylene, substituted or unsubstituted 5 to 7 membered heterocycloalkylene, substituted or unsubstituted arylene, substituted or unsubstituted heteroarylene, —O—, —NH—, —S—, and —$CH_2$—.

In another exemplary embodiment, $Q^1$-$R^1$, $Q^2$-$R^2$, $Q^3$-$R^3$, $Q^4$-$R^4$, $Q^5$-$R^5$, $Q^6$-$R^6$, $Q^7$-$R^7$, $Q^8$-$R^8$, $Q^9$-$R^9$, and $Q^{10}$-$R^{10}$ are independently selected from hydrogen, —$OPO_3H_2$, —OH, —$OCH_3$, —$CH_3$, —C(O)H, —C(O)—$R^{11}$, —$CH_2OH$, —$NHR^{11}$, —O—CH($CH_3$)COO$R^{12}$, —C(O)O$R^{13}$, —$CHR^{14}$—$CHR^{15}$—$CH_2R^{16}$, an activated leaving group, a nucleotidyl moiety and -L-M. At least one of $R^1$, $R^2$, $R^3$, $R^4$, $R^5$, $R^6$, $R^7$, $R^8$, $R^9$, and $R^{10}$ is -L-M. M is a modifying group as described below.

L is a linker independently selected from a bond, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, —O—, —NH—, —S—, and $CH_2$—. Exemplary linking arms are displayed below (e.g. Formulae IV and V).

$R^{11}$, $R^{12}$, $R^{13}$, $R^{14}$, $R^{15}$, and $R^{16}$ are independently selected from hydrogen, substituted or unsubstituted alkyl, substituted or unsubstituted heteroalkyl, and -$L^1$-$M^1$. $M^1$ is modifying group as described below.

$L^1$ is a linker independently selected from a bond, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, —O—, —NH—, —S—, and $CH_2$—. Exemplary linking arms are displayed below (e.g. Formulae IV and V).

In a related embodiment, at least one of $Q^1$-$R^1$, $Q^2$-$R^2$, $Q^3$-$R^3$, $Q^4$-$R^4$, $Q^5$-$R^5$, $Q^6$-$R^6$, $Q^7$-$R^7$, $Q^8$-$R^8$, $Q^9$-$R^9$, and $Q^{10}$-$R^{10}$ is —OH. In another related embodiment, at least one of $Q^1$-$R^1$, $Q^2$-$R^2$, $Q^3$-$R^3$, $Q^4$-$R^4$, $Q^5$-$R^5$, $Q^6$-$R^6$, $Q^7$-$R^7$, $Q^8$-$R^8$, $Q^9$-$R^9$, and $Q^{10}$-$R^{10}$ is hydrogen.

$R^{11}$ may be selected from hydrogen, acetyl, and —CH(O$R^{11A}$)—CH(O$R^{11B}$)—$CH_2OR^{11C}$. $R^{11A}$, $R^{11B}$, and $R^{11C}$ are independently selected from hydrogen, and -$L^2$-$M^2$. $L^2$ is a linker independently selected from a bond, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, —O—, —NH—, —S—, and $CH_2$—. $M^2$ is modifying group as described below.

$R^{12}$ and $R^{13}$ may independently be selected from hydrogen and -$L^1$-$M^1$.

In another exemplary embodiment, $L^1$ and $L^2$ are independently selected from a bond, substituted or unsubstituted ($C_1$-$C_{10}$) alkylene, substituted or unsubstituted 2 to 10 membered heteroalkylene, substituted or unsubstituted $C_5$-$C_7$ cycloalkylene, substituted or unsubstituted 5 to 7 membered heterocycloalkylene, substituted or unsubstituted arylene, substituted or unsubstituted heteroarylene, —O—, —NH—, —S—, and CH$_2$—. Exemplary linking arms are displayed below (e.g. Formulae IV and V).

In another exemplary embodiment, M, M$^1$, and M$^2$ are independently selected from a water insoluble polymer, a water-soluble polymer, therapeutic moiety, and a biomolecule.

The modified sugar may be a modified sialic acid. In an exemplary embodiment, the modified sialic acid has the formula

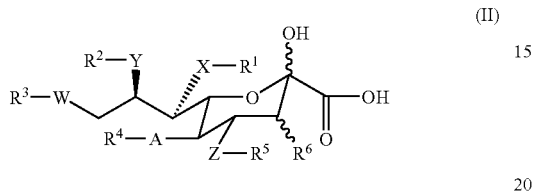

(II)

In Formula (II), the symbols W, X, Y, Z, and A represent linking moieties independently selected from a bond, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, —O—, —N(R$^7$)—, —S—, and CH$_2$—. R$^7$ is a member independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. In a related embodiment, W is —NH—C(O)—. In another related embodiment, A is —NH—C(O)—.

The symbols R$^1$, R$^2$, R$^3$, R$^4$, R$^5$ and R$^6$ are independently selected from —OH, —NH$_2$, —SH, —N(M$^1$)$_2$, hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, and a modifying group. M is a modifying group. At least one of R$^1$, R$^2$, R$^3$, R$^4$, R$^5$ and R$^6$ is a modifying group or —N(M$^1$)$_2$. M$^1$ is independently selected from a modifying group.

In an exemplary embodiment, R$^1$, R$^2$, R$^3$, R$^4$, R$^5$ and R$^6$ are independently selected from —OH, —NH$_2$, —SH, hydrogen, substituted or unsubstituted (C$_1$-C$_{10}$) alkyl, substituted or unsubstituted 2 to 10 membered heteroalkyl, substituted or unsubstituted (C$_5$-C$_7$) cycloalkyl, substituted or unsubstituted 5 to 7 membered heterocycloalkyl, substituted or unsubstituted aryl, substituted or unsubstituted heteroaryl, and a modifying group. In a related embodiment, R$^6$ represents hydrogen, —OH, or a polymer. In another related embodiment, R$^3$ is a water soluble polymer. In another related embodiment, R$^4$ is a water soluble polymer. In another related embodiment, R$^5$ is a water soluble polymer.

The modifying group may be selected from a water-insoluble polymer, a water-soluble polymer, therapeutic moiety, and a biomolecule.

In another exemplary embodiment, X, Y, and/or Z are bonds, and R$^1$, R$^2$ and/or R$^5$ are —OH.

One of skill in the art will immediately recognize that the substitutions similar to those shown in Formula (II) may be made in any appropriate sugar to form a modified sugar of the present invention.

Table 2 sets for the further exemplary modified sugars, where R represents a modifying group.

TABLE 2

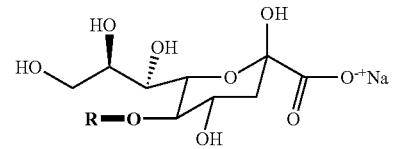

KDN-5-O—R

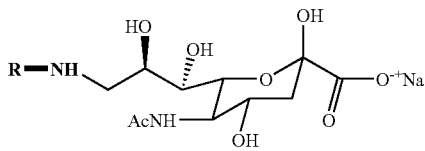

NeuAc-9-NH—R

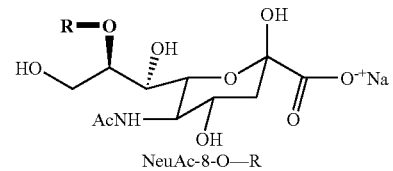

NeuAc-8-O—R

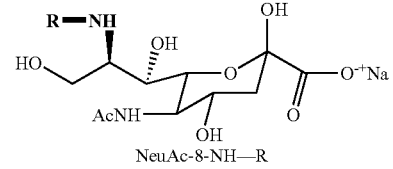

NeuAc-8-NH—R

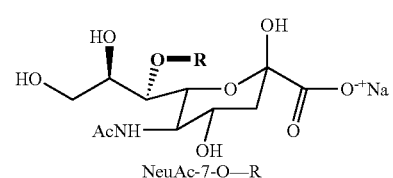

NeuAc-7-O—R

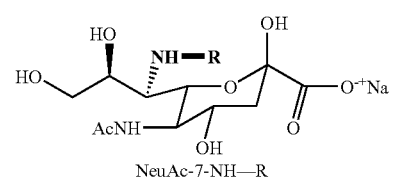

NeuAc-7-NH—R

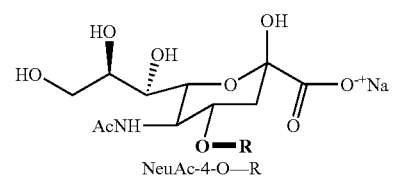

NeuAc-4-O—R

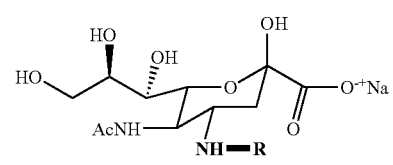

TABLE 2-continued

NeuAc-4-NH—R

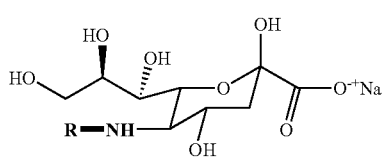

TABLE 2-continued

SA-5-NH—R

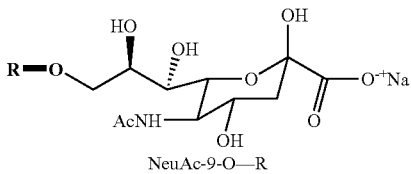

NeuAc-9-O—R

The modified sugar may also be a modified nucleotide sugar. Any modified nucleotide sugar can be used with its appropriate glycosyltransferase, depending on the amino acid or terminal sugar of the oligosaccharide side chains of the glycopeptide. Exemplary modified nucleotide sugars are presented in Table 3 and Table 4 below.

TABLE 3

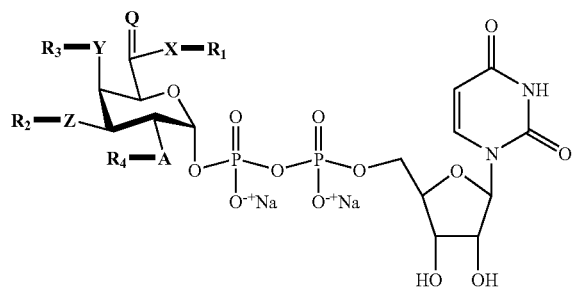

Modified UDP-galactose

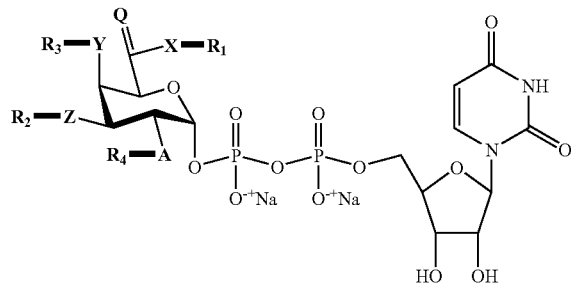

Modified UDP-galactosamine
(when A = NH, $R_4$ may be acetyl)

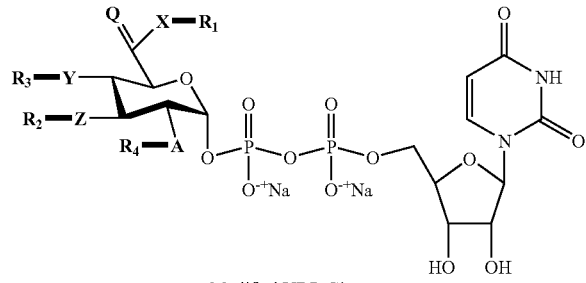

Modified UDP-Glucose

TABLE 3-continued

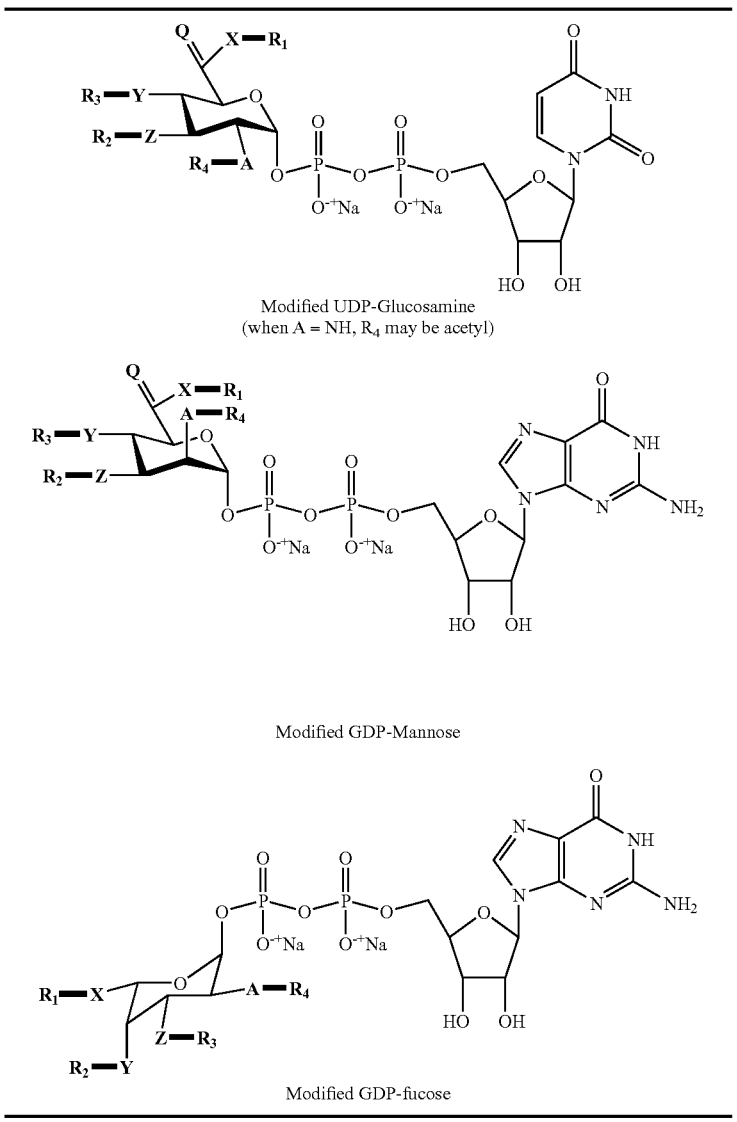

Modified UDP-Glucosamine
(when A = NH, R₄ may be acetyl)

Modified GDP-Mannose

Modified GDP-fucose

In Table 3, X, Y, Z, and A are as defined above in Formula (II). $R_1$, $R_2$, $R_3$ and $R_4$ are as defined above for $R^1$, $R^4$, $R^5$ and $R^6$, respectively, in Formula (II). Q is selected from $H_2$, =O, =S, =NH, and =N-L-M. L is a linker independently selected from a bond, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, —O—, —NH—, —S—, and —CH₂—. M is a modifying group as described below.

TABLE 4

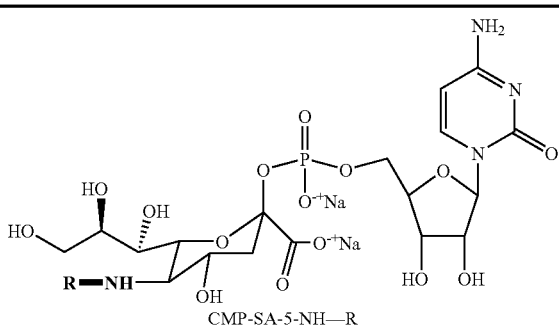

CMP-SA-5-NH—R

TABLE 4-continued
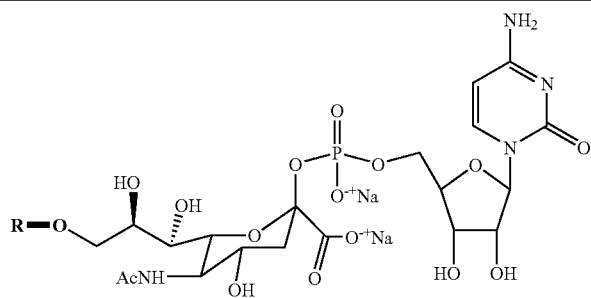
CMP-NeuAc-9-O—R
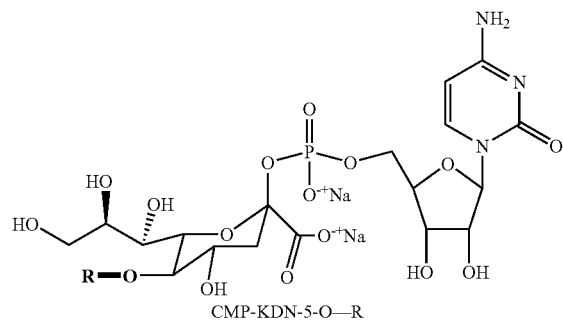
CMP-KDN-5-O—R
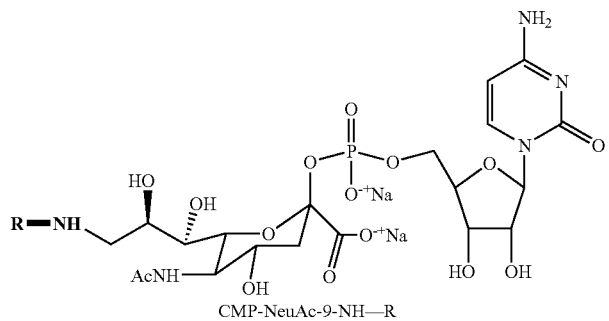
CMP-NeuAc-9-NH—R
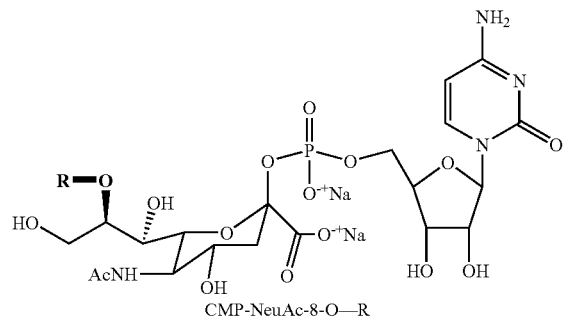
CMP-NeuAc-8-O—R
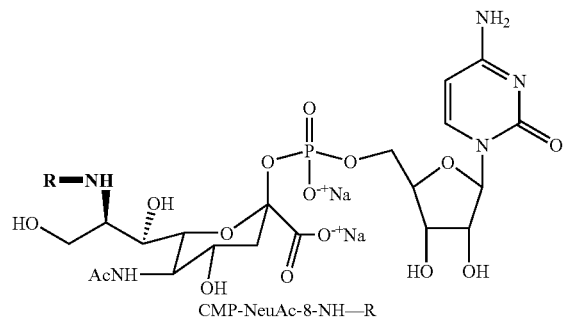
CMP-NeuAc-8-NH—R TABLE 4-continued
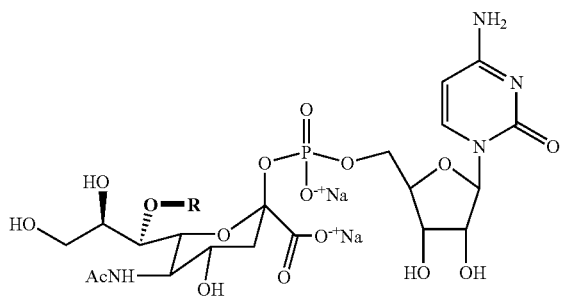
CMP-NeuAc-7-O—R
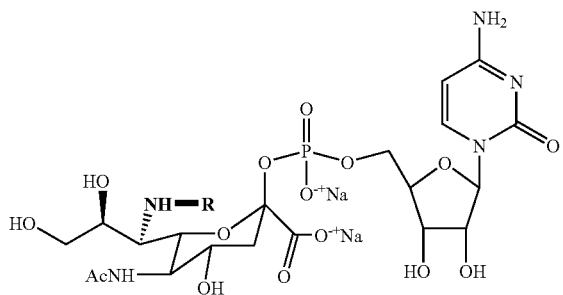
CMP-NeuAc-7-NH—R
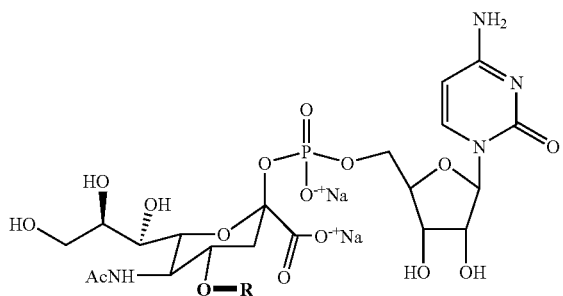
CMP-NeuAc-4-O—R
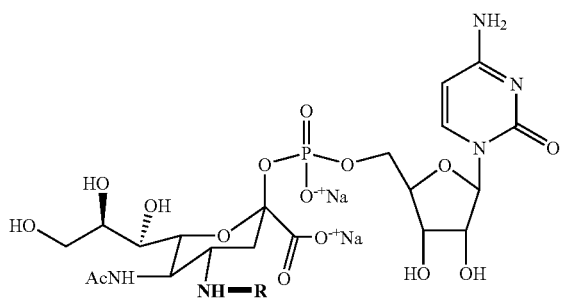
CMP-NeuAc-4-NH—R In Table 4, R is a modifying group.

The modified nucleotide sugars of use in practicing the present invention can be substituted in other positions as well as those set forth above in Tables 3 and 4 above. Exemplary substitutions of modified nucleotide sialic acids are set forth in Formula (III):

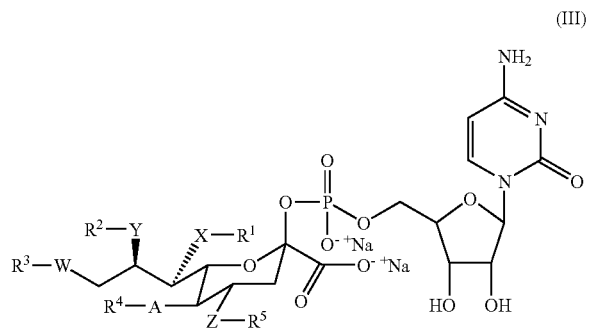

In Formula (III), X, Y, W, A, Z, $R^1$, $R^2$, $R^3$, $R^4$, and $R^5$ are linking groups as defined above in Formula (II).

3. Modifying Groups

A wide variety of modifying groups are useful in the methods of the present invention. The exemplary modifying groups discussed below are presented for clarity of illustration and should not be construed as limiting the scope of the modifying groups of use in practicing the invention.

i. Water-Soluble Polymers

The hydrophilicity of a selected peptide is enhanced by conjugation with polar molecules such as amine-, ester-, hydroxyl- and polyhydroxyl-containing molecules. Representative examples include, but are not limited to, polylysine, polyethyleneimine, poly(ethylene glycol) and poly(propyleneglycol). Preferred water-soluble polymers are essentially non-fluorescent, or emit such a minimal amount of fluorescence that they are inappropriate for use as a fluorescent marker in an assay. Polymers that are not naturally occurring sugars may be used. In addition, the use of an otherwise naturally occurring sugar that is modified by covalent attachment of another entity (e.g., poly(ethylene glycol), poly(propylene glycol), poly(aspartate), biomolecule, therapeutic moiety, diagnostic moiety, etc.) is also contemplated. In another exemplary embodiment, a therapeutic sugar moiety is conjugated to a linker arm and the sugar-linker arm is subsequently conjugated to a peptide via a method of the invention.

Methods and chemistry for activation of water-soluble polymers and saccharides as well as methods for conjugating saccharides and polymers to various species are described in the literature. Commonly used methods for activation of polymers include activation of functional groups with cyanogen bromide, periodate, glutaraldehyde, biepoxides, epichlorohydrin, divinylsulfone, carbodiimide, sulfonyl halides, trichlorotriazine, etc. (see, R. F. Taylor, (1991), PROTEIN IMMOBILISATION. FUDAMENTALS AND APPLICATIONS, Marcel Dekker, N.Y.; S. S. Wong, (1992), CHEMISTRY OF PROTEIN CONJUGATION AND CROSSLINKING, CRC Press, Boca Raton; G. T. Hermanson et al., (1993), IMMOBILIZED AFFINITY LIGAND TECHNIQUES, Academic Press, N.Y.; Dunn, R. L., et al., Eds. POLYMERIC DRUGS AND DRUG DELIVERY SYSTEMS, ACS Symposium Series Vol. 469, American Chemical Society, Washington, D.C. 1991).

Routes for preparing reactive PEG molecules and forming conjugates using the reactive molecules are known in the art. For example, U.S. Pat. No. 5,672,662 discloses a water soluble and isolatable conjugate of an active ester of a polymer acid selected from linear or branched poly(alkylene oxides), poly(oxyethylated polyols), poly(olefinic alcohols), and poly(acrylomorpholine), wherein the polymer has about 44 or more recurring units.

U.S. Pat. No. 6,376,604 sets forth a method for preparing a water-soluble 1-benzotriazolylcarbonate ester of a water-soluble and non-peptidic polymer by reacting a terminal hydroxyl of the polymer with di(1-benzotriazoyl)carbonate in an organic solvent. The active ester is used to form conjugates with a biologically active agent such as a protein or peptide.

WO 99/45964 describes a conjugate comprising a biologically active agent and an activated water soluble polymer comprising a polymer backbone having at least one terminus linked to the polymer backbone through a stable linkage, wherein at least one terminus comprises a branching moiety having proximal reactive groups linked to the branching moiety, in which the biologically active agent is linked to at least one of the proximal reactive groups. Other branched poly (ethylene glycols) are described in WO 96/21469, U.S. Pat. No. 5,932,462 describes a conjugate formed with a branched PEG molecule that includes a branched terminus that includes reactive functional groups. The free reactive groups are available to react with a biologically active species, such as a protein or peptide, forming conjugates between the poly (ethylene glycol) and the biologically active species. U.S. Pat. No. 5,446,090 describes a bifunctional PEG linker and its use in forming conjugates having a peptide at each of the PEG linker termini.

Conjugates that include degradable PEG linkages are described in WO 99/34833; and WO 99/14259, as well as in U.S. Pat. No. 6,348,558. Such degradable linkages are applicable in the present invention.

Although both reactive PEG derivatives and conjugates formed using the derivatives are known in the art, until the present invention, it was not recognized that a conjugate could be formed between PEG (or other polymer) and another species, such as a peptide or glycopeptide, through a intact glycosyl linking group.

Many water-soluble polymers are known to those of skill in the art and are useful in practicing the present invention. The term water-soluble polymer encompasses species such as saccharides (e.g., dextran, amylose, hyalouronic acid, poly (sialic acid), heparans, heparins, etc.); poly (amino acids); nucleic acids; synthetic polymers (e.g., poly(acrylic acid), poly(ethers), e.g., poly(ethylene glycol); peptides, proteins, and the like. The present invention may be practiced with any water-soluble polymer with the sole limitation that the polymer must include a point at which the remainder of the conjugate can be attached.

Methods for activation of polymers can also be found in WO 94/17039, U.S. Pat. No. 5,324,844, WO 94/18247, WO 94/04193, U.S. Pat. No. 5,219,564, U.S. Pat. No. 5,122,614, WO 90/13540, U.S. Pat. No. 5,281,698, and more WO 93/15189, and for conjugation between activated polymers and peptides, e.g. Coagulation Factor VIII (WO 94/15625), hemoglobin (WO 94/09027), oxygen carrying molecule (U.S. Pat. No. 4,412,989), ribonuclease and superoxide dismutase (Veronese at al., *App. Biochem. Biotech.* 11: 141-45 (1985)).

Preferred water-soluble polymers are those in which a substantial proportion of the polymer molecules in a sample of the polymer are of approximately the same molecular weight; such polymers are "homodisperse."

The present invention is further illustrated by reference to a poly(ethylene glycol) conjugate. Several reviews and monographs on the functionalization and conjugation of PEG are available. See, for example, Harris, *Macronol. Chem. Phys.* C25: 325-373 (1985); Scouten, *Methods in Enzymology* 135: 30-65 (1987); Wong et al., *Enzyme Microb. Technol.* 14: 866-874 (1992); Delgado et al., *Critical Reviews in Therapeutic Drug Carrier Systems* 9: 249-304 (1992); Zalipsky, *Bioconjugate Chem.* 6: 150-165 (1995); and Bhadra, et al., *Pharmazie,* 57:5-29 (2002).

Poly(ethylene glycol) molecules suitable for use in the invention include, but are not limited to, those described by the following Formula (IV):

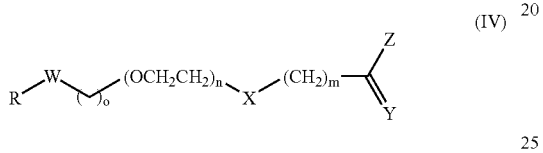

in which R is selected from H, alkyl, benzyl, aryl, acetal, OHC—, $H_2N-CH_2CH_2-$, $HS-CH_2CH_2-$, -sugar-nucleotide, protein, methyl, ethyl and

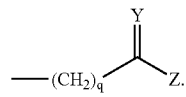

The symbols X, Y, W, U represent members that are independently selected from O, S, NH, and N—R'. The symbol R' represents alkyl, benzyl, aryl, alkyl aryl, pyridyl, substituted aryl, arylalkyl, acylaryl. The subscript n represents and integer from 1 to 2000. The subscripts m, q, o, and p are members independently selected from the integers from 0 to 20.

The symbol Z represents a member selected from HO, $NH_2$, halogen, S—R''', activated esters, -sugar-nucleotide, protein, imidazole, HOBT, tetrazole, halide,

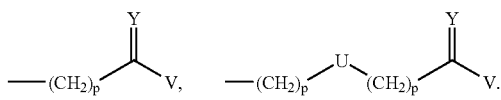

V is HO, $NH_2$, halogen, S—R''' (R''' is identical to R'), activated esters, activated amides, -sugar-nucleotide, and protein.

Exemplary activated PEG moieties of use in practicing the present invention

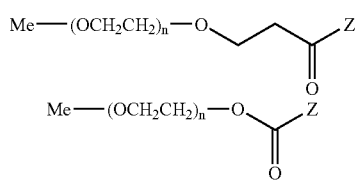

include:

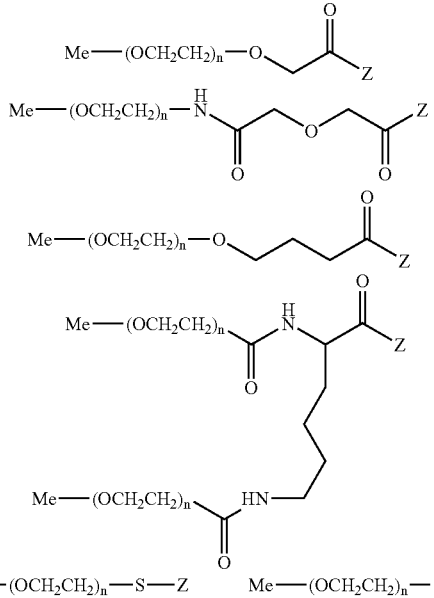

Although the above structures set forth linear portions of PEG, the poly(ethylene glycol) useful in forming the conjugate of the invention is either linear or branched. Branched poly(ethylene glycol) molecules suitable for use in the invention include, but are not limited to, those described by the following Formula (V):

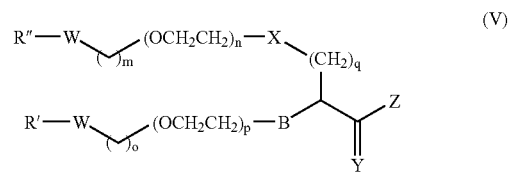

in which R', R'', and R''' are members independently selected from H, alkyl, benzyl, aryl, acetal, OHC—, $H_2N-CH_2CH_2-$, $HS-CH^2CH_2-$, $-(CH_2)_qCY-Z$, -sugar-nucleotide, protein, methyl, ethyl, heteroaryl, acylalkyl, acylaryl, and acylalkylaryl. X, Y, W, A, B are members independently selected from O, S, NH, N—R', $(CH_2)$, -sugar-nucleotide, and peptide. The subscripts n, p independently represent the integers from 1 to 2000. The symbols, m, q, o independently represent the integers from 0 to 20.

The symbol Z represents HO, $NH_2$, halogen, S—R''', activated esters,

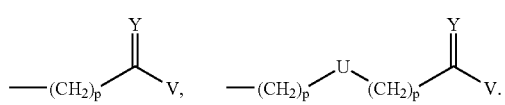

V is a member selected from —OH, $-NH_2$, halogen, —S—R''', activated esters, activated amides, -sugar-nucleotide, and peptide.

The in vivo half-life, area under the curve, and/or residence time of peptide conjugate of the invention can also be enhanced with water-soluble polymers such as polyethylene glycol (PEG) and polypropylene glycol (PPG). For example, chemical modification of proteins with PEG (PEGylation) increases their molecular size and decreases their surface- and functional group-accessibility, each of which are dependent on the size of the PEG attached to the protein. This results in an improvement of plasma half-lives and in proteolytic-stability, and a decrease in immunogenicity and hepatic uptake (Chaffee et al. *J. Clin. Invest.* 89: 1643-1651 (1992); Pyatak et al. *Res. Commun. Chem. Pathol Pharmacol.* 29: 113-127 (1980)). PEGylation of interleukin-2 has been reported to increase its antitumor potency in vivo (Katre et al. *Proc. Natl. Acad. Sci. USA.* 84: 1487-1491 (1987)) and PEGylation of a F(ab')2 derived from the monoclonal antibody A7 has improved its tumor localization (Kitamura et al. *Biochem. Biophys. Res. Commun.* 28: 1387-1394 (1990)).

In one preferred embodiment, the in vivo half-life of a peptide derivatized with a water-soluble polymer by a method of the invention is increased relevant to the in vivo half-life of the non-derivatized peptide. In another preferred embodiment, the area under the curve of a peptide derivatized with a water-soluble polymer using a method of the invention is increased relevant to the area under the curve of the non-derivatized peptide. In another preferred embodiment, the residence time of a peptide derivatized with a water-soluble polymer using a method of the invention is increased relevant to the residence time of the non-derivatized peptide. Techniques to determine the in vivo half-life, the area under the curve and the residence time are well known in the art. Descriptions of such techniques can be found in J. G. Wagner, 1993, Pharmacokinetics for the Pharmaceutical Scientist, Technomic Publishing Company, Inc. Lancaster Pa.

The increase in peptide in vivo half-life is best expressed as a range of percent increase in this quantity. The lower end of the range of percent increase is about 40%, about 60%, about 80%, about 100%, about 150% or about 200%. The upper end of the range is about 60%, about 80%, about 100%, about 150%, or more than about 250%.

In an exemplary embodiment, the present invention provides a PEGylated follicle stimulating hormone. In another exemplary embodiment, the invention provides a PEGylated transferrin. Other useful PEGylated peptides include granulocyte colony stimulating factor, interferon-alpha, interferon-beta, interferon-omega, alpha-galactosidase A, alpha-iduronidase, anti-thrombin III, human chorionic gonadotropin, Factor VIIa, Factor IX, erythropoietin, granulocyte macrophage colony stimulating factor, interferon-gamma, alpha-1-protease inhibitor, glucocerebrosidase, tissue plasminogen activator protein, interleukin-2, Factor VIII, chimeric tumor necrosis factor receptor, urokinase, chimeric anti-glycoprotein IIb/IIIa antibody, chimeric anti-HER2 antibody, chimeric anti-respiratory syncytial virus antibody, chimeric anti-CD20 antibody, DNAase, chimeric anti-tumor necrosis factor antibody, human insulin, hepatitis B sAg, human growth hormone, and portions thereof.

Other exemplary water-soluble polymers of use in the invention include, but are not limited to linear or branched poly(alkylene oxides), poly(oxyethylated polyols), poly(olefinic alcohols), and poly(acrylomorpholine), dextran, starch, poly(amino acids), etc.

ii. Water-Insoluble Polymers

The conjugates of the invention may also include one or more water-insoluble polymers. This embodiment of the invention is illustrated by the use of the conjugate as a vehicle with which to deliver a therapeutic peptide in a controlled manner. Polymeric drug delivery systems are known in the art. See, for example, Dunn et al., Eds. POLYMERIC DRUGS AND DRUG DELIVERY SYSTEMS, ACS Symposium Series Vol. 469, American Chemical Society, Washington, D.C. 1991. Those of skill in the art will appreciate that substantially any known drug delivery system is applicable to the conjugates of the present invention.

Representative water-insoluble polymers include, but are not limited to, polyphosphazines, poly(vinyl alcohols), polyamides, polycarbonates, polyalkylenes, polyacrylamides, polyalkylene glycols, polyalkylene oxides, polyalkylene terephthalates, polyvinyl ethers, polyvinyl esters, polyvinyl halides, polyvinylpyrrolidone, polyglycolides, polysiloxanes, polyurethanes, poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate) polyethylene, polypropylene, poly(ethylene glycol), poly(ethylene oxide), poly (ethylene terephthalate), poly(vinyl acetate), polyvinyl chloride, polystyrene, polyvinyl pyrrolidone, pluronics and polyvinylphenol and copolymers thereof Synthetically modified natural polymers of use in conjugates of the invention include, but are not limited to, alkyl celluloses, hydroxyalkyl celluloses, cellulose ethers, cellulose esters, and nitrocelluloses. Particularly preferred members of the broad classes of synthetically modified natural polymers include, but are not limited to, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, cellulose sulfate sodium salt, and polymers of acrylic and methacrylic esters and alginic acid.

These and the other polymers discussed herein can be readily obtained from commercial sources such as Sigma Chemical Co. (St. Louis, Mo.), Polysciences (Warrenton, Pa.), Aldrich (Milwaukee, Wis.), Fluka (Ronkonkoma, N.Y.), and BioRad (Richmond, Calif.), or else synthesized from monomers obtained from these suppliers using standard techniques.

Representative biodegradable polymers of use in the conjugates of the invention include, but are not limited to, polylactides, polyglycolides and copolymers thereof, poly(ethylene terephthalate), poly(butyric acid), poly(valeric acid), poly(lactide-co-caprolactone), poly(lactide-co-glycolide), polyanhydrides, polyorthoesters, blends and copolymers thereof. Of particular use are compositions that form gels, such as those including collagen, pluronics and the like.

The polymers of use in the invention include "hybrid" polymers that include water-insoluble materials having within at least a portion of their structure, a bioresorbable molecule. An example of such a polymer is one that includes a water-insoluble copolymer, which has a bioresorbable region, a hydrophilic region and a plurality of crosslinkable functional groups per polymer chain.

For purposes of the present invention, "water-insoluble materials" includes materials that are substantially insoluble in water or water-containing environments. Thus, although certain regions or segments of the copolymer may be hydrophilic or even water-soluble, the polymer molecule, as a whole, does not to any substantial measure dissolve in water.

For purposes of the present invention, the term "bioresorbable molecule" includes a region that is capable of being metabolized or broken down and resorbed and/or eliminated through normal excretory routes by the body. Such metabolites or break down products are preferably substantially non-toxic to the body.

The bioresorbable region may be either hydrophobic or hydrophilic, so long as the copolymer composition as a whole is not rendered water-soluble. Thus, the bioresorbable region is selected based on the preference that the polymer, as a whole, remains water-insoluble. Accordingly, the relative properties, i.e., the kinds of functional groups contained by, and the relative proportions of the bioresorbable region, and the hydrophilic region are selected to ensure that useful bioresorbable compositions remain water-insoluble.

Exemplary resorbable polymers include, for example, synthetically produced resorbable block copolymers of poly($\alpha$-hydroxy-carboxylic acid)/poly(oxyalkylene, (see, Cohn et al., U.S. Pat. No. 4,826,945). These copolymers are not crosslinked and are water-soluble so that the body can excrete the degraded block copolymer compositions. See, Younes et al., *J Biomed. Mater. Res.* 21: 1301-1316 (1987); and Cohn et al., *J Biomed. Mater. Res.* 22: 993-1009 (1988).

Presently preferred bioresorbable polymers include one or more components selected from poly(esters), poly(hydroxy acids), poly(lactones), poly(amides), poly(ester-amides), poly (amino acids), poly(anhydrides), poly(orthoesters), poly (carbonates), poly(phosphazines), poly(phosphoesters), poly (thioesters), polysaccharides and mixtures thereof. More preferably still, the bioresorbable polymer includes a poly (hydroxy) acid component. Of the poly(hydroxy) acids, polylactic acid, polyglycolic acid, polycaproic acid, polybutyric acid, polyvaleric acid and copolymers and mixtures thereof are preferred.

In addition to forming fragments that are absorbed in vivo ("bioresorbed"), preferred polymeric coatings for use in the methods of the invention can also form an excretable and/or metabolizable fragment.

Higher order copolymers can also be used in the present invention. For example, Casey et al., U.S. Pat. No. 4,438,253, which issued on Mar. 20, 1984, discloses tri-block copolymers produced from the transesterification of poly(glycolic acid) and an hydroxyl-ended poly(alkylene glycol). Such compositions are disclosed for use as resorbable monofilament sutures. The flexibility of such compositions is controlled by the incorporation of an aromatic orthocarbonate, such as tetra-p-tolyl orthocarbonate into the copolymer structure.

Other coatings based on lactic and/or glycolic acids can also be utilized. For example, Spinu, U.S. Pat. No. 5,202,413, which issued on Apr. 13, 1993, discloses biodegradable multi-block copolymers having sequentially ordered blocks of polylactide and/or polyglycolide produced by ring-opening polymerization of lactide and/or glycolide onto either an oligomeric diol or a diamine residue followed by chain extension with a di-functional compound, such as, a diisocyanate, diacylchloride or dichlorosilane.

Bioresorbable regions of coatings useful in the present invention can be designed to be hydrolytically and/or enzymatically cleavable. For purposes of the present invention, "hydrolytically cleavable" refers to the susceptibility of the copolymer, especially the bioresorbable region, to hydrolysis in water or a water-containing environment. Similarly, "enzymatically cleavable" as used herein refers to the susceptibility of the copolymer, especially the bioresorbable region, to cleavage by endogenous or exogenous enzymes.

When placed within the body, the hydrophilic region can be processed into excretable and/or metabolizable fragments. Thus, the hydrophilic region can include, for example, polyethers, polyalkylene oxides, polyols, poly(vinyl pyrrolidine), poly(vinyl alcohol), poly(alkyl oxazolines), polysaccharides, carbohydrates, peptides, proteins and copolymers and mixtures thereof. Furthermore, the hydrophilic region can also be, for example, a poly(alkylene) oxide. Such poly(alkylene) oxides can include, for example, poly(ethylene) oxide, poly (propylene) oxide and mixtures and copolymers thereof.

Polymers that are components of hydrogels are also useful in the present invention. Hydrogels are polymeric materials that are capable of absorbing relatively large quantities of water. Examples of hydrogel forming compounds include, but are not limited to, polyacrylic acids, sodium carboxymethylcellulose, polyvinyl alcohol, polyvinyl pyrrolidine, gelatin, carrageenan and other polysaccharides, hydroxyethylenemethacrylic acid (HEMA), as well as derivatives thereof, and the like. Hydrogels can be produced that are stable, biodegradable and bioresorbable. Moreover, hydrogel compositions can include subunits that exhibit one or more of these properties.

Bio-compatible hydrogel compositions whose integrity can be controlled through crosslinking are known and are presently preferred for use in the methods of the invention. For example, Hubbell et al., U.S. Pat. No. 5,410,016, which issued on Apr. 25, 1995 and U.S. Pat. No. 5,529,914, which issued on Jun. 25, 1996, disclose water-soluble systems, which are crosslinked block copolymers having a water-soluble central block segment sandwiched between two hydrolytically labile extensions. Such copolymers are further end-capped with photopolymerizable acrylate functionalities. When crosslinked, these systems become hydrogels. The water soluble central block of such copolymers can include poly(ethylene glycol); whereas, the hydrolytically labile extensions can be a poly($\alpha$-hydroxy acid), such as polyglycolic acid or polylactic acid. See, Sawhney et al., *Macromolecules* 26: 581-587 (1993).

In another preferred embodiment, the gel is a thermoreversible gel. Thermoreversible gels including components, such as pluronics, collagen, gelatin, hyalouronic acid, polysaccharides, polyurethane hydrogel, polyurethane-urea hydrogel and combinations thereof are presently preferred.

In yet another exemplary embodiment, the conjugate of the invention includes a component of a liposome. Liposomes can be prepared according to methods known to those skilled in the art, for example, as described in Eppstein et al., U.S. Pat. No. 4,522,811, which issued on Jun. 11, 1985. For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its pharmaceutically acceptable salt is then introduced into the container. The container is then swirled by hand to free lipid material from the sides of the container and to disperse lipid aggregates, thereby forming the liposomal suspension.

The above-recited microparticles and methods of preparing the microparticles are offered by way of example and they are not intended to define the scope of microparticles of use in the present invention. It will be apparent to those of skill in the art that an array of microparticles, fabricated by different methods, are of use in the present invention.

iii. Biomolecules

In another embodiment, the modified sugar bears a biomolecule. In an exemplary embodiment, the biomolecule is a functional protein, enzyme, antigen, antibody, peptide, nucleic acid (e.g., single nucleotides or nucleosides, oligonucleotides, polynucleotides and single- and higher-stranded nucleic acids), lectin, receptor or a combination thereof.

In another embodiment, the biomolecule is fluorescent. The use of an otherwise naturally occurring sugar that is modified by covalent attachment of another entity (e.g., PEG, biomolecule, therapeutic moiety, diagnostic moiety, etc.) is appropriate. In an exemplary embodiment, a sugar moiety, which is a biomolecule, is conjugated to a linker arm and the sugar-linker arm cassette is subsequently conjugated to a peptide via a method of the invention.

Biomolecules useful in practicing the present invention can be derived from any source. The biomolecules can be isolated from natural sources or they can be produced by synthetic methods. Peptides can be natural peptides or mutated peptides. Mutations can be effected by chemical mutagenesis, site-directed mutagenesis or other means of inducing mutations known to those of skill in the art. Peptides useful in practicing the instant invention include, for example, enzymes, antigens, antibodies and receptors. Antibodies can be either polyclonal or monoclonal; either intact or fragments. The peptides are optionally the products of a program of directed evolution.

Both naturally derived and synthetic peptides and nucleic acids are of use in conjunction with the present invention; these molecules can be attached to a sugar residue component or a crosslinking agent by any available reactive group. For example, peptides can be attached through a reactive amine, carboxyl, sulfhydryl, or hydroxyl group. The reactive group can reside at a peptide terminus or at a site internal to the peptide chain. Nucleic acids can be attached through a reactive group on a base (e.g., exocyclic amine) or an available hydroxyl group on a sugar moiety (e.g., 3'- or 5'-hydroxyl). The peptide and nucleic acid chains can be further derivatized at one or more sites to allow for the attachment of appropriate reactive groups onto the chain. See, Chrisey et al. *Nucleic Acids Res.* 24: 3031-3039 (1996).

In another exemplary embodiment, the biomolecule is selected to direct the peptide modified by the methods of the invention to a specific tissue, thereby enhancing the delivery of the peptide to that tissue relative to the amount of underivatized peptide that is delivered to the tissue. In a still further preferred embodiment, the amount of derivatized peptide delivered to a specific tissue within a selected time period is enhanced by derivatization by at least about 20%, more preferably, at least about 40%, and more preferably still, at least about 100%. Presently, preferred biomolecules for targeting applications include antibodies, hormones and ligands for cell-surface receptors.

In another exemplary embodiment, the modifying group is a nucleic acid. Nucleic acids are defined above.

In an exemplary embodiment, the modifying group is a protein. In an exemplary embodiment, the protein is an interferon. The interferons are antiviral glycoproteins that, in humans, are secreted by human primary fibroblasts after induction with virus or double-stranded RNA. Interferons are of interest as therapeutics, e.g., antivirals and treatment of multiple sclerosis. For references discussing interferon-β, see, e.g., Yu, et al., *J. Neuroimmunol.*, 64(1):91-100 (1996); Schmidt, J., *J. Neurosci. Res.*, 65(1):59-67 (2001); Wender, et al., *Folia Neuropathol.*, 39(2):91-93 (2001); Martin, et al., *Springer Semin. Immunopathol.*, 18(1):1-24 (1996); Takane, et al., *J. Pharmacol. Exp. Ther.*, 294(2):746-752 (2000); Sburlati, et al., *Biotechnol. Prog.*, 14:189-192 (1998); Dodd, et al., *Biochimica et Biophysica Acta*, 787:183-187 (1984); Edelbaum, et al., *J. Interferon Res.*, 12:449-453 (1992); Conradt, et al., *J. Biol. Chem.*, 262(30):14600-14605 (1987); Civas, et al, *Eur. J. Biochem.*, 173:311-316 (1988); Demolder, et al., *J. Biotechnol.*, 32:179-189 (1994); Sedmak, et al., *J. Interferon Res.*, 9(Suppl 1):S61-S65 (1989); Kagawa, et al., *J. Biol. Chem.*, 263(33):17508-17515 (1988); Hershenson, et al., U.S. Pat. No. 4,894,330; Jayaram, et al., *J. Interferon Res.*, 3(2):177-180 (1983); Menge, et al., *Develop. Biol. Standard.*, 66:391-401 (1987); Vonk, et al., *J. Interferon Res.*, 3(2):169-175 (1983); and Adolf, et al., *J. Interferon Res.*, 10:255-267 (1990). For references relevant to interferon-α, see, Asano, et al., *Eur. J. Cancer*, 27(Suppl 4):S21-S25 (1991); Nagy, et al., *Anticancer Research*, 8(3):467-470 (1988); Dron, et al., *J. Biol. Regul. Homeost. Agents*, 3(1):13-19 (1989); Habib, et al., *Am. Surg.*, 67(3):257-260 (March 2001); and Sugyiama, et al, *Eur. J. Biochem.*, 217:921-927 (1993).

In an exemplary interferon conjugate, interferon β is conjugated to a second peptide via a linker arm. The linker arm includes a intact glycosyl linking group through which it is attached to the second peptide via a method of the invention. The linker arm also optionally includes a second intact glycosyl linking group, through which it is attached to the interferon.

In another exemplary embodiment, the invention provides a conjugate of follicle stimulating hormone (FSH). FSH is a glycoprotein hormone. See, for example, Saneyoshi, et al., *Biol Reprod.*, 65:1686-1690 (2001); Hakola, et al., *J. Endocrinol.*, 158:441-448 (1998); Stanton, et al., *Mol. Cell. Endocrinol.*, 125:133-141 (1996); Walton, et al., *J. Clin. Endocrinol. Metab.*, 86(8):3675-3685 (August 2001); Ulloa-Aguirre, et al., *Endocrine*, 11(3):205-215 (December 1999); Castro-Fernández, et al., *J. Clin. Endocrinol. Matab.*, 85(12): 4603-4610 (2000); Prevost, Rebecca R., *Pharmacotherapy*, 18(5):1001-1010 (1998); Linskens, et al., *The FASEB Journal*, 13:639-645 (April 1999); Butnev, et al., *Biol. Reprod.*, 58:458-469 (1998); Muyan, et al., *Mol. Endo.*, 12(5):766-772 (1998); Min, et al., *Endo. J.*, 43(5):585-593 (1996); Boime, et al., *Recent Progress in Hormone Research*, 34:271-289 (1999); and Rafferty, et al., *J. Endo.*, 145:527-533 (1995). The FSH conjugate can be formed in a manner similar to that described for interferon.

In yet another exemplary embodiment, the conjugate includes erythropoietin (EPO). EPO is known to mediate response to hypoxia and to stimulate the production of red blood cells. For pertinent references, see, Cerami, et al., *Seminars in Oncology*, 28(2)(Suppl 8):66-70 (April 2001). An exemplary EPO conjugate is formed analogously to the conjugate of interferon.

In a further exemplary embodiment, the invention provides a conjugate of human granulocyte colony stimulating factor (G-CSF). G-CSF is a glycoprotein that stimulates proliferation, differentiation and activation of neutropoietic progenitor cells into functionally mature neutrophils. Injected G-CSF is known to be rapidly cleared from the body. See, for example, Nohynek, et al., *Cancer Chemother. Pharmacol.*, 39:259-266 (1997); Lord, et al., *Clinical Cancer Research*, 7(7):2085-2090 (July 2001); Rotondaro, et al., *Molecular Biotechnology*, 11(2):117-128 (1999); and Bönig, et al., *Bone Marrow Transplantation*, 28:259-264 (2001). An exemplary conjugate of G-CSF is prepared as discussed above for the conjugate of the interferons. One of skill in the art will appreciate that many other proteins may be conjugated to interferon using the methods and compositions of the invention, including but not limited to, the peptides discussed below and in U.S. application Ser. No. 10/287,994, which is commonly owned by the same assignee and herein incorporated by reference in its entirety for all purposes.

In still a further exemplary embodiment, there is provided a conjugate with biotin. Thus, for example, a selectively biotinylated peptide is elaborated by the attachment of an avidin or streptavidin moiety bearing one or more modifying groups.

In a further preferred embodiment, the biomolecule is selected to direct the peptide modified by the methods of the invention to a specific intracellular compartment, thereby enhancing the delivery of the peptide to that intracellular compartment relative to the amount of underivatized peptide that is delivered to the tissue. In a still further preferred embodiment, the amount of derivatized peptide delivered to a specific intracellular compartment within a selected time period is enhanced by derivatization by at least about 20%, more preferably, at least about 40%, and more preferably still, at least about 100%. In another particularly preferred embodiment, the biomolecule is linked to the peptide by a cleavable linker that can hydrolyze once internalized. Presently, preferred biomolecules for intracellular targeting applications include transferrin, lactotransferrin (lactoferrin), melanotransferrin (p97), ceruloplasmin, and divalent cation transporter. Contemplated linkages include, but are not limited to, protein-sugar-linker-sugar-protein, protein-sugar-linker-protein and multivalent forms thereof, and protein-sugar-linker-drug where the drug includes small molecules, peptides, lipids, among others.

Site-specific and target-oriented delivery of therapeutic agents is desirable for the purpose of treating a wide variety of human diseases, such as different types of malignancies and certain neurological disorders. Such procedures are accompanied by fewer side effects and a higher efficacy of drug. Various principles have been relied on in designing these delivery systems. For a review, see Garnett, *Advanced Drug Delivery Reviews* 53:171-216 (2001).

One important consideration in designing a drug delivery system to target tissues specifically. The discovery of tumor surface antigens has made it possible to develop therapeutic approaches where tumor cells displaying definable surface antigens are specifically targeted and killed. There are three main classes of therapeutic monoclonal antibodies (MAb) that have demonstrated effectiveness in human clinical trials in treating malignancies: (1) unconjugated MAb, which either directly induces growth inhibition and/or apoptosis, or indirectly activates host defense mechanisms to mediate antitumor cytotoxicity; (2) drug-conjugated MAb, which preferentially delivers a potent cytotoxic toxin to the tumor cells and therefore minimizes the systemic cytotoxicity commonly associated with conventional chemotherapy; and (3) radio-isotope-conjugated MAb, which delivers a sterilizing dose of radiation to the tumor. See review by Reff et al., *Cancer Control* 9:152-166 (2002).

In order to arm MAbs with the power to kill malignant cells, the MAbs can be connected to a toxin, which may be obtained from a plant, bacterial, or fungal source, to form chimeric proteins called immunotoxins. Frequently used plant toxins are divided into two classes: (1) holotoxins (or class II ribosome inactivating proteins), such as ricin, abrin, mistletoe lectin, and modeccin, and (2) hemitoxins (class I ribosome inactivating proteins), such as pokeweed antiviral protein (PAP), saporin, Bryodin 1, bouganin, and gelonin. Commonly used bacterial toxins include diphtheria toxin (DT) and Pseudomonas exotoxin (PE). Kreitman, *Current Pharmaceutical Biotechnology* 2:313-325 (2001).

Conventional immunotoxins contain an MAb chemically conjugated to a toxin that is mutated or chemically modified to minimized binding to normal cells. Examples include anti-B4-blocked ricin, targeting CD5; and RFB4-deglycosylated ricin A chain, targeting CD22. Recombinant immunotoxins developed more recently are chimeric proteins consisting of the variable region of an antibody directed against a tumor antigen fused to a protein toxin using recombinant DNA technology. The toxin is also frequently genetically modified to remove normal tissue binding sites but retain its cytotoxicity. A large number of differentiation antigens, overexpressed receptors, or cancer-specific antigens have been identified as targets for immunotoxins, e.g., CD19, CD22, CD20, IL-2 receptor (CD25), CD33, IL-4 receptor, EGF receptor and its mutants, ErB2, Lewis carbohydrate, mesothelin, transferrin receptor, GM-CSF receptor, Ras, Bcr-Abl, and c-Kit, for the treatment of a variety of malignancies including hematopoietic cancers, glioma, and breast, colon, ovarian, bladder, and gastrointestinal cancers. See e.g., Brinkmann et al., *Expert Opin. Biol. Ther.* 1:693-702 (2001); Perentesis and Sievers, *Hematology/Oncology Clinics of North America* 15:677-701 (2001).

MAbs conjugated with radioisotope are used as another means of treating human malignancies, particularly hematopoietic malignancies, with a high level of specificity and effectiveness. The most commonly used isotopes for therapy are the high-energy -emitters, such as $^{131}$I and $^{90}$Y. Recently, $^{213}$Bi-labeled anti-CD33 humanized MAb has also been tested in phase I human clinical trials. Reff et al., supra.

A number of MAbs have been used for therapeutic purposes. For example, the use of rituximab (Rituxan™), a recombinant chimeric anti-CD20 MAb, for treating certain hematopoietic malignancies was approved by the FDA in 1997. Other MAbs that have since been approved for therapeutic uses in treating human cancers include: alemtuzumab (Campath-1H™), a humanized rat antibody against CD52; and gemtuzumab ozogamicin (Mylotarg™), a calicheamicin-conjugated humanized mouse antCD33 MAb. The FDA is also currently examining the safety and efficacy of several other MAbs for the purpose of site-specific delivery of cytotoxic agents or radiation, e.g., radiolabeled Zevalin™ and Bexxar™. Reff et al., supra.

A second important consideration in designing a drug delivery system is the accessibility of a target tissue to a therapeutic agent. This is an issue of particular concern in the case of treating a disease of the central nervous system (CNS), where the blood-brain barrier prevents the diffusion of macromolecules. Several approaches have been developed to bypass the blood-brain barrier for effective delivery of therapeutic agents to the CNS.

The understanding of iron transport mechanism from plasma to brain provides a useful tool in bypassing the blood-brain barrier (BBB). Iron, transported in plasma by transferrin, is an essential component of virtually all types of cells. The brain needs iron for metabolic processes and receives iron through transferrin receptors located on brain capillary endothelial cells via receptor-mediated transcytosis and endocytosis. Moos and Morgan, *Cellular and Molecular Neurobiology* 20:77-95 (2000). Delivery systems based on transferrin-transferrin receptor interaction have been established for the efficient delivery of peptides, proteins, and liposomes into the brain. For example, peptides can be coupled with a Mab directed against the transferrin receptor to achieve greater uptake by the brain, Moos and Morgan, Supra. Similarly, when coupled with an MAb directed against the transferrin receptor, the transportation of basic fibroblast growth factor (bFGF) across the blood-brain barrier is enhanced. Song et al., *The Journal of Pharmacology and Experimental Therapeutics* 301:605-610 (2002); Wu et al., *Journal of Drug Targeting* 10:239-245 (2002). In addition, a liposomal delivery system for effective transport of the chemotherapy drug, doxorubicin, into C6 glioma has been reported, where transferrin was attached to the distal ends of liposomal PEG chains. Eavarone et al., *J. Biomed. Mater. Res.*

51:10-14 (2000). A number of US patents also relate to delivery methods bypassing the blood-brain barrier based on transferrin-transferrin receptor interaction. See e.g., U.S. Pat. Nos. 5,154,924; 5,182,107; 5,527,527; 5,833,988; 6,015,555.

There are other suitable conjugation partners for a pharmaceutical agent to bypass the blood-brain barrier. For example, U.S. Pat. Nos. 5,672,683, 5,977,307 and WO 95/02421 relate to a method of delivering a neuropharmaceutical agent across the blood-brain barrier, where the agent is administered in the form of a fusion protein with a ligand that is reactive with a brain capillary endothelial cell receptor; WO 99/00150 describes a drug delivery system in which the transportation of a drug across the blood-brain barrier is facilitated by conjugation with an MAb directed against human insulin receptor; WO 89/10134 describes a chimeric peptide, which includes a peptide capable of crossing the blood brain barrier at a relatively high rate and a hydrophilic neuropeptide incapable of transcytosis, as a means of introducing hydrophilic neuropeptides into the brain; WO 01/60411 A1 provides a pharmaceutical composition that can easily transport a pharmaceutically active ingredient into the brain. The active ingredient is bound to a hibernation-specific protein that is used as a conjugate, and administered with a thyroid hormone or a substance promoting thyroid hormone production. In addition, an alternative route of drug delivery for bypassing the blood-brain barrier has been explored. For instance, intranasal delivery of therapeutic agents without the need for conjugation has been shown to be a promising alternative delivery method (Frey, 2002, Drug Delivery Technology, 2(5):46-49).

In addition to facilitating the transportation of drugs across the blood-brain barrier, transferrin-transferrin receptor interaction is also useful for specific targeting of certain tumor cells, as many tumor cells overexpress transferrin receptor on their surface. This strategy has been used for delivering bioactive macromolecules into K562 cells via a transferrin conjugate (Wellhoner et al., *The Journal of Biological Chemistry* 266:4309-4314 (1991)), and for delivering insulin into enterocyte-like Caco-2 cells via a transferrin conjugate (Shah and Shen, *Journal of Pharmaceutical Sciences* 85:1306-1311 (1996)).

Furthermore, as more becomes known about the functions of various iron transport proteins, such as lactotransferrin receptor, melanotransferrin, ceruloplasmin, and Divalent Cation Transporter and their expression pattern, some of the proteins involved in iron transport mechanism (e.g., melanotransferrin), or their fragments, have been found to be similarly effective in assisting therapeutic agents transport across the blood-brain barrier or targeting specific tissues (WO 02/13843 A2, WO 02/13873 A2). For a review on the use of transferrin and related proteins involved in iron uptake as conjugates in drug delivery, see Li and Qian, *Medical Research Reviews* 22:225-250 (2002).

The concept of tissue-specific delivery of therapeutic agents goes beyond the interaction between transferrin and transferrin receptor or their related proteins. For example, a bone-specific delivery system has been described in which proteins are conjugated with a bone-seeking aminobisphosphate for improved delivery of proteins to mineralized tissue. Uludag and Yang, *Biotechnol. Prog.* 18:604-611 (2002). For a review on this topic, see Vyas et al., *Critical Reviews in Therapeutic Drug Carrier System* 18:1-76 (2001).

A variety of linkers may be used in the process of generating bioconjugates for the purpose of specific delivery of therapeutic agents. Suitable linkers include homo- and heterobifunctional cross-linking reagents, which may be cleavable by, e.g., acid-catalyzed dissociation, or non-cleavable (see, e.g., Srinivasachar and Neville, *Biochemistry* 28:2501-2509 (1989); Wellhoner et al., *The Journal of Biological Chemistry* 266:4309-4314 (1991)). Interaction between many known binding partners, such as biotin and avidin/streptavidin, can also be used as a means to join a therapeutic agent and a conjugate partner that ensures the specific and effective delivery of the therapeutic agent. Using the methods of the invention, proteins may be used to deliver molecules to intracellular compartments as conjugates. Proteins, peptides, hormones, cytokines, small molecules or the like that bind to specific cell surface receptors that are internalized after ligand binding may be used for intracellular targeting of conjugated therapeutic compounds. Typically, the receptor-ligand complex is internalized into intracellular vesicles that are delivered to specific cell compartments, including, but not limited to, the nucleus, mitochondria, golgi, ER, lysosome, and endosome, depending on the intracellular location targeted by the receptor. By conjugating the receptor ligand with the desired molecule, the drug will be carried with the receptor-ligand complex and be delivered to the intracellular compartments normally targeted by the receptor. The drug can therefore be delivered to a specific intracellular location in the cell where it is needed to treat a disease.

Many proteins may be used to target therapeutic agents to specific tissues and organs. Targeting proteins include, but are not limited to, growth factors (EPO, HGH, EGF, nerve growth factor, FGF, among others), cytokines (GM-CSF, G-CSF, the interferon family, interleukins, among others), hormones (FSH, LH, the steroid families, estrogen, corticosteroids, insulin, among others), serum proteins (albumin, lipoproteins, fetoprotein, human serum proteins, antibodies and fragments of antibodies, among others), and vitamins (folate, vitamin C, vitamin A, among others). Targeting agents are available that are specific for receptors on most cells types.

Contemplated linkage configurations include, but are not limited to, protein-sugar-linker-sugar-protein and multivalent forms thereof, protein-sugar-linker-protein and multivalent forms thereof, protein-sugar-linker-therapeutic agent, where the therapeutic agent includes, but are not limited to, small molecules, peptides and lipids.

In an exemplary embodiment, transferrin is conjugated via a linker to an enzyme desired to be targeted to a cell that presents transferrin receptors in a patient. The patient could, for example, require enzyme replacement therapy for that particular enzyme. In particularly preferred embodiments, the enzyme is one that is lacking in a patient with a lysosomal storage disease. Once in circulation, the transferrin-enzyme conjugate binds to transferrin receptors and is internalized in early endosomes (Xing et al., 1998, Biochem. J. 336:667; Li et al., 2002, Trends in Pharmcol. Sci. 23:206; Suhaila et al., 1998, J. Biol. Chem. 273:14355). Other contemplated targeting agents that are related to transferrin include, but are not limited to, lactotransferrin (lactoferrin), melanotransferrin (p97), ceruloplasmin, and divalent cation transporter.

In another exemplary embodiment, transferrin-dystrophin conjugates would enter endosomes by the transferrin pathway. Once there, the dystrophin is released due to a hydrolysable linker which can then be taken to the intracellular compartment where it is required. This embodiment may be used to treat a patient with muscular dystrophy by supplementing a genetically defective dystrophin gene and/or protein with the functional dystrophin peptide connected to the transferrin.

iv. Therapeutic Moieties

In another preferred embodiment, the modified sugar includes a therapeutic moiety. Those of skill in the art will appreciate that there is overlap between the category of therapeutic moieties and biomolecules; many biomolecules have therapeutic properties or potential.

The therapeutic moieties can be agents already accepted for clinical use or they can be drugs whose use is experimental, or whose activity or mechanism of action is under investigation. The therapeutic moieties can have a proven action in a given disease state or can be only hypothesized to show desirable action in a given disease state. In a preferred embodiment, the therapeutic moieties are compounds, which are being screened for their ability to interact with a tissue of choice. Therapeutic moieties, which are useful in practicing the instant invention include drugs from a broad range of drug classes having a variety of pharmacological activities. In some embodiments, it is preferred to use therapeutic moieties that are not sugars. An exception to this preference is the use of a sugar that is modified by covalent attachment of another entity, such as a PEG, biomolecule, therapeutic moiety, diagnostic moiety and the like. In another exemplary embodiment, a therapeutic sugar moiety is conjugated to a linker arm and the sugar-linker arm cassette is subsequently conjugated to a peptide via a method of the invention.

Methods of conjugating therapeutic and diagnostic agents to various other species are well known to those of skill in the art. See, for example Hermanson, BIOCONJUGATE TECHNIQUES, Academic Press, San Diego, 1996; and Dunn et al., Eds. POLYMERIC DRUGS AND DRUG DELIVERY SYSTEMS, ACS Symposium Series Vol. 469, American Chemical Society, Washington, D.C. 1991.

In an exemplary embodiment, the therapeutic moiety is attached to the modified sugar via a linkage that is cleaved under selected conditions. Exemplary conditions include, but are not limited to, a selected pH (e.g., stomach, intestine, endocytotic vacuole), the presence of an active enzyme (e.g., esterase, protease, reductase, oxidase), light, heat and the like. Many cleavable groups are known in the art. See, for example, Jung et al., Biochem. Biophys. Acta, 761: 152-162 (1983); Joshi et al., J. Biol. Chem., 265: 14518-14525 (1990); Zarling et al., J. Immunol., 124: 913-920 (1980); Bouizar et al., Eur. J. Biochem., 155: 141-147 (1986); Park et al., J. Biol. Chem., 261: 205-210 (1986); Browning et al., J. Immunol., 143: 1859-1867 (1989).

Classes of useful therapeutic moieties include, for example, non-steroidal anti-inflammatory drugs (NSAIDS). The NSAIDS can, for example, be selected from the following categories: (e.g., propionic acid derivatives, acetic acid derivatives, fenamic acid derivatives, biphenylcarboxylic acid derivatives and oxicams); steroidal anti-inflammatory drugs including hydrocortisone and the like; adjuvants; antihistaminic drugs (e.g., chlorpheniramine, triprolidine); antitussive drugs (e.g., dextromethorphan, codeine, caramiphen and carbetapentane); antipruritic drugs (e.g. methdilazine and trimeprazine); anticholinergic drugs (e.g., scopolamine, atropine, homatropine, levodopa); anti-emetic and antinauseant drugs (e.g., cyclizine, meclizine, chlorpromazine, buclizine); anorexic drugs (e.g., benzphetamine, phentermine, chlorphentermiine, fenfluramine); central stimulant drugs (e.g., amphetamine, methamphetamine, dextroamphetamine and methylphenidate); antiarrhythmic drugs (e.g., propanolol, procainamide, disopyramide, quinidine, encainide); adrenergic blocker drugs (e.g., metoprolol, acebutolol, betaxolol, labetalol and timolol); cardiotonic drugs (e.g., milrinone, amrinone and dobutamine); antihypertensive drugs (e.g., enalapril, clonidine, hydralazine, minoxidil, guanadrel, guanethidine); diuretic drugs (e.g., amiloride and hydrochlorothiazide); vasodilator drugs (e.g., diltiazem, amiodarone, isoxsuprine, nylidrin, tolazoline and verapamil); vasoconstrictor drugs (e.g., dihydroergotamine, ergotamine and methylsergide); antiulcer drugs (e.g., ranitidine and cimetidine); anesthetic drugs (e.g., lidocaine, bupivacaine, chloroprocaine, dibucaine); antidepressant drugs (e.g., imipramine, desipramine, amitryptiline, nortryptiline); tranquilizer and sedative drugs (e.g., chlordiazepoxide, benacytyzine, benzquinamide, flurazepam, hydroxyzine, loxapine and promazine); antipsychotic drugs (e.g., chlorprothixene, fluphenazine, haloperidol, molindone, thioridazine and trifluoperazine); antimicrobial drugs (antibacterial, antifungal, antiprotozoal and antiviral drugs).

Classes of useful therapeutic moieties include adjuvants. The adjuvants can, for example, be selected from keyhole lymphet hemocyanin conjugates, monophosphoryl lipid A, mycoplasma-derived lipopeptide MALP-2, cholera toxin B subunit, *Escherichia coli* heat-labile toxin, universal T helper epitope from tetanus toxoid, interleukin-12, CpG oligodeoxynucleotides, dimethyldioctadecylammonium bromide, cyclodextrin, squalene, aluminum salts, meningococcal outer membrane vesicle (OMV), montanide ISA, TiterMax™ (available from Sigma, St. Louis Mo.), nitrocellulose absorption, immune-stimulating complexes such as Quil A, Gerbu™ adjuvant (Gerbu Biotechnik, Kirchwald, Germany), threonyl muramyl dipeptide, thymosin alpha, bupivacaine, GM-CSF, Incomplete Freund's Adjuvant, MTP-PE/MF59 (Ciba/Geigy, Basel, Switzerland), polyphosphazene, saponin derived from the soapbark tree *Quillaja saponaria*, and Syntex adjuvant formulation (Biocine, Emeryville, Calif.), among others well known to those in the art.

Antimicrobial drugs which are preferred for incorporation into the present composition include, for example, pharmaceutically acceptable salts of β-lactam drugs, quinolone drugs, ciprofloxacin, norfloxacin, tetracycline, erythromycin, amikacin, triclosan, doxycycline, capreomycin, chlorhexidine, chlortetracycline, oxytetracycline, clindamycin, ethambutol, hexamidine isothionate, metronidazole, pentamidine, gentamycin, kanamycin, lineomycin, methacycline, methenamine, minocycline, neomycin, netilmycin, paromomycin, streptomycin, tobramycin, miconazole and amantadine.

Other drug moieties of use in practicing the present invention include antineoplastic drugs (e.g., antiandrogens (e.g., leuprolide or flutamide), cytocidal agents (e.g., adriamycin, doxorubicin, taxol, cyclophosphamide, busulfan, cisplatin, β-2-interferon) anti-estrogens (e.g., tamoxifen), antimetabolites (e.g., fluorouracil, methotrexate, mercaptopurine, thioguanine). Also included within this class are radioisotope-based agents for both diagnosis and therapy, and conjugated toxins, such as ricin, geldanamycin, mytansin, CC-1065, C-1027, the duocarmycins, calicheamycin and related structures and analogues thereof.

The therapeutic moiety can also be a hormone (e.g., medroxyprogesterone, estradiol, leuprolide, megestrol, octreotide or somatostatin); muscle relaxant drugs (e.g., cinnamedrine, cyclobenzaprine, flavoxate, orphenadrine, papaverine, mebeverine, idaverine, ritodrine, diphenoxylate, dantrolene and azumolen); antispasmodic drugs; bone-active drugs (e.g., diphosphonate and phosphonoalkylphosphinate drug compounds); endocrine modulating drugs (e.g., contraceptives (e.g., ethinodiol, ethinyl estradiol, norethindrone, mestranol, desogestrel, medroxyprogesterone), modulators of diabetes (e.g., glyburide or chlorpropamide), anabolics, such as testolactone or stanozolol, androgens (e.g., methyltestosterone, testosterone or fluoxymesterone), antidiuretics (e.g., desmopressin) and calcitonins).

Also of use in the present invention are estrogens (e.g., diethylstilbesterol), glucocorticoids (e.g., triamcinolone, betamethasone, etc.) and progesterones, such as norethindrone, ethynodiol, norethindrone, levonorgestrel; thyroid agents (e.g., liothyronine or levothyroxine) or anti-thyroid agents (e.g., methimazole); antihyperprolactinemic drugs (e.g., cabergoline); hormone suppressors (e.g., danazol or goserelin), oxytocics (e.g., methylergonovine or oxytocin) and prostaglandins, such as mioprostol, alprostadil or dinoprostone, can also be employed.

Other useful modifying groups include immunomodulating drugs (e.g., antihistamines, mast cell stabilizers, such as lodoxamide and/or cromolyn, steroids (e.g., triamcinolone, beclomethazone, cortisone, dexamethasone, prednisolone, methylprednisolone, beclomethasone, or clobetasol), histamine H2 antagonists (e.g., famotidine, cimetidine, ranitidine), immunosuppressants (e.g., azathioprine, cyclosporin), etc. Groups with anti-inflammatory activity, such as sulindac, etodolac, ketoprofen and ketorolac, are also of use. Other drugs of use in conjunction with the present invention will be apparent to those of skill in the art.

v. Detectable Labels

In an exemplary embodiment, the modifying group is a detectable label, such as a fluorophores or radioactive isotope. For example, the detectable label can be appended to a glycosyl moiety (e.g., sialic acid) by means of a linker arm in a manner that still allows the labeled glycosyl moiety serves as a substrate for an appropriate glycosyltransferase as discussed herein.

The embodiment of the invention in which a label is utilized is exemplified by the use of a fluorescent label. Fluorescent labels have the advantage of requiring few precautions in their handling, and being amenable to high-throughput visualization techniques (optical analysis including digitization of the image for analysis in an integrated system comprising a computer). Preferred labels are typically characterized by high sensitivity, high stability, low background, long lifetimes, low environmental sensitivity and high specificity in labeling.

Many fluorescent labels can be incorporated into the compositions of the invention. Many such labels are commercially available from, for example, the SIGMA chemical company (Saint Louis, Mo.), Molecular Probes (Eugene, Oreg.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), and Applied Biosystems (Foster City, Calif.), as well as many other commercial sources known to one of skill. Furthermore, those of skill in the art will recognize how to select an appropriate fluorophore for a particular application and, if it not readily available commercially, will be able to synthesize the necessary fluorophore de novo or synthetically modify commercially available fluorescent compounds to arrive at the desired fluorescent label.

4. Methods of Linking Peptides

In another embodiment, the invention provides a method for linking two or more peptides through a bifunctional linking group containing a first and second reactive group at each end. Each reactive functional group may be covalently bound to a sugar to form a first and second modified sugar at a first and second end of the bifunctional linking group. The bifunctional linking group containing a first and second modified sugar at its first and second end is hereinafter referred to as a "dual modified sugar linker."

In an exemplary embodiment, one end of the dual modified sugar linker is intracellularly contacted with a glycosyltransferase and a glycosylated or non-glycosylated peptide to form a single peptide conjugate linker (e.g., having a dual modified sugar linker bound to one peptide via an intact glycosyl linking group), which is subsequently isolated from the cell. After isolation, the single peptide conjugate linker is contacted with a glycosyltransferase and glycosylated or non-glycosylated peptide in vitro to form the corresponding dual peptide conjugate linker.

In an exemplary method of the invention, two peptides are linked together using a dual modified sugar linker that includes a modifying groups (e.g. a water-soluble polymer such as a PEG linker). The focus on a water soluble polymer, such a PEG linker, that includes two glycosyl groups is for purposes of clarity and should not be interpreted as limiting the identity of linker arms of use in this embodiment of the invention.

For example, a PEG moiety is functionalized at a first terminus with a first glycosyl unit and at a second terminus with a second glycosyl unit to form a first and second modified glycosyl unit at each end of the PEG moiety. The first and second modified glycosyl units are preferably substrates for two different nucleotidyl transferases, which attaches each modified glycosyl unit to the nucleotidyl moiety of a first and second nucleotide to form a first and second modified nucleotide glycosyl unit. Each modified nucleotide glycosyl unit is preferably recognized by two different glycosyltransferases, allowing orthogonal attachment of the first and second peptides to the first and second modified nucleotide glycosyl units, respectively. In practice, the (modified nucleotide glycosyl)$^1$-PEG-(modified nucleotide glycosyl)$^2$ linker is intracellularly contacted with the first peptide and a first glycosyltransferase for which the first modified nucleotide glycosyl unit is a substrate, thereby forming (peptide)$^1$-(modified glycosyl)$^1$-PEG-(modified nucleotide glycosyl)$^2$. The second peptide and a second glycosyltransferase for which the second modified nucleotide glycosyl unit is a substrate are added in vitro to the (peptide)$^1$-(modified glycosyl)$^1$-PEG-(modified nucleotide glycosyl)$^2$ conjugate, forming (peptide)$^1$-(modified glycosyl)$^1$-PEG-(modified glycosyl)$^2$-(peptide)$^2$. Those of skill in the art will appreciate that the method outlined above is also applicable to forming conjugates between more than two peptides by, for example, the use of a branched PEG, dendrimer, poly(amino acid), polysaccharide or the like. Linking groups useful in the methods of the current invention are further described in U.S. application Ser. No. 10/287,994, which is commonly owned by the same assignee and herein incorporated in its entirety for all purposes.

In an exemplary embodiment, human growth hormone is conjugated to transferrin using a dual modified sugar linker to form a dual peptide conjugate that includes an intact glycosyl linking group at each terminus of a water-soluble polymer such as a PEG moiety. The hGH conjugate has an in vivo half-life that is increased over that of hGH alone by virtue of the greater molecular sized of the conjugate. Moreover, the conjugation of hGH to transferrin serves to selectively target the conjugate to the brain. For example, one terminus of a PEG linker is functionalized with a CMP sialic acid and the other is functionalized with an UDP GalNAc. A hGH conjugate having a GalNAc intact glycosyl linker is formed intracellularly using the methods of the present invention. The hGH conjugate is combined in vitro with a silica acid-containing transferrin in the presence of a sialyltransferase, resulting in the attachment of the CMP sialic acid of hGH conjugate to the sialic acid arm on the transferrin to from the hGH-transferrin dual peptide conjugate.

One skilled in the art would immediately recognize that multiple peptides may be linked together using one or more dual modified sugar linkers. Alternatively, the dual modified sugar linker may have additional modifying groups capable of forming covalent bonds with peptides. Thus, the processes described above is not limited to forming a conjugate between two peptides with a single linker.

Another exemplary embodiment is set forth in Scheme 4. Scheme 4 shows a method of preparing a conjugate that targets a selected protein, e.g., human growth hormone, to bone and increases the circulatory half-life of the selected protein. The HSGP conjugate is formed intracellularly using an intracellular sialyltransferase. The HSGP-conjugate is then contacted in vitro with hGH and a galactosyltransferase to link the hGH with the HSGP to form the hGH-HSGP dual peptide conjugate.

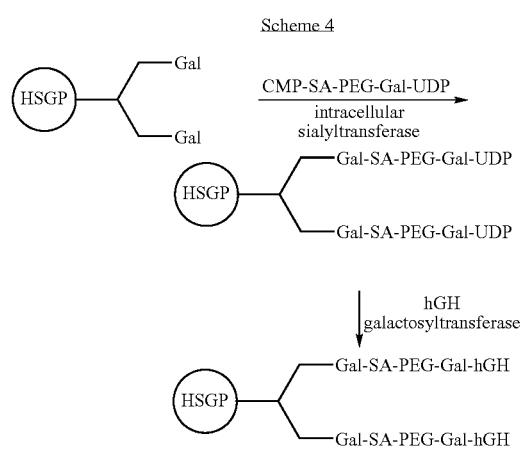

Scheme 4

In another exemplary embodiment, interleukin-2 (IL-2) is conjugated to transferrin using a dual modified sugar linker to form a dual peptide conjugate that includes a glycosyl linking group at each terminus of, for example, a PEG moiety. For example, one terminus of the PEG linker is functionalized with an intact sialic acid linker that is attached to transferrin and the other is functionalized with an intact GalNAc linker that is attached to IL-2.

In another exemplary embodiment, EPO is conjugated to transferrin. In another exemplary embodiment, EPO is conjugated to glial derived neurotropic growth factor (GDNF). In this embodiment, each conjugation is accomplished via a bifunctional linker that includes a intact glycosyl linking group at each terminus of the PEG moiety. Transferrin transfers the protein across the blood brain barrier.

The use of reactive derivatives of PEG (or other linkers) to attach one or more peptide moieties to the linker is within the scope of the present invention. The invention is not limited by the identity of the reactive PEG analogue. Many activated derivatives of poly(ethyleneglycol) are available commercially and in the literature. It is well within the abilities of one of skill to choose, and synthesize if necessary, an appropriate activated PEG derivative with which to prepare a substrate useful in the present invention. See, Abuchowski et al. *Cancer Biochem. Biophys.*, 7: 175-186 (1984); Abuchowski et al., *J. Biol. Chem.*, 252: 3582-3586 (1977); Jackson et al., *Anal. Biochem.*, 165: 114-127 (1987); Koide et al., *Biochem Biophys. Res. Commun.*, 111: 659-667 (1983)), tresylate (Nilsson et al., *Methods Enzymol.*, 104: 56-69 (1984); Delgado et al., *Biotechnol. Appl. Biochem.*, 12: 119-128 (1990)); N-hydroxysuccinimide derived active esters (Buckmann et al., *Makromol. Chem.*, 182: 1379-1384 (1981); Joppich et al., *Makromol. Chem.*, 180: 1381-1384 (1979); Abuchowski et al., *Cancer Biochem. Biophys.*, 7: 175-186 (1984); Katre et al. *Proc. Natl. Acad. Sci. U.S.A.*, 84: 1487-1491 (1987); Kitamura et al., *Cancer Res.*, 51: 4310-4315 (1991); Boccu et al., *Z. Naturforsch.*, 38C: 94-99 (1983), carbonates (Zalipsky et al., POLY(ETHYLENE GLYCOL) CHEMISTRY: BIOTECHNICAL AND BIOMEDICAL APPLICATIONS, Harris, Ed., Plenum Press, New York, 1992, pp. 347-370; Zalipsky et al., *Biotechnol. Appl. Biochem.*, 15: 100-114 (1992); Veronese et al., *Appl Biochem. Biotech.*, 11: 141-152 (1985)), imidazolyl formates (Beauchamp et al., *Anal. Biochem.*, 131: 25-33 (1983); Berger et al., *Blood*, 71: 1641-1647 (1988)), 4-dithiopyridines (Woghiren et al., *Bioconjugate Chem.*, 4: 314-318 (1993)), isocyanates (Byun et al., *ASAIO Journal*, M649-M-653 (1992)) and epoxides (U.S. Pat. No. 4,806,595, issued to Noishiki et al., (1989). Other linking groups include the urethane linkage between amino groups and activated PEG. See, Veronese, et al., *Appl. Biochem. Biotechnol.*, 11: 141-152 (1985).

5. Preparation of Modified Sugars

Sugar moieties and modifying groups are linked together through the use of reactive groups, which are typically transformed by a linking process into a new organic functional group or unreactive species. The sugar reactive functional group(s), is located at any position on the sugar moiety. Currently favored classes of reactions available with reactive sugar moieties are those which proceed under relatively mild conditions. These include nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, Smith and March, ADVANCED ORGANIC CHEMISTRY, 5th Ed., John Wiley & Sons, New York, 2001; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Useful reactive functional groups pendent from a sugar nucleus or modifying group include:

(a) carboxyl groups and various derivatives thereof including, but not limited to, N-hydroxysuccinimide esters, N-hydroxybenzotriazole esters, acid halides, acyl imidazoles, thioesters, p-nitrophenyl esters, alkyl, alkenyl, alkynyl and aromatic esters;

(b) hydroxyl groups, which can be converted to, e.g., esters, ethers, aldehydes, etc.

(c) haloalkyl groups, wherein the halide can be later displaced with a nucleophilic group such as, for example, an amine, a carboxylate anion, thiol anion, carbanion, or an alkoxide ion, thereby resulting in the covalent attachment of a new group at the functional group of the halogen atom;

(d) dienophile groups, which are capable of participating in Diels-Alder reactions such as, for example, maleimido groups;

(e) aldehyde or ketone groups, such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be, for example, converted to disulfides or reacted with alkyl and acyl halides;

(h) amine or sulfhydryl groups, which can be, for example, acylated, alkylated or oxidized;
(i) alkenes, which can undergo, for example, cycloadditions, acylation, Michael addition, etc; and
(j) epoxides, which can react with, for example, amines and hydroxyl compounds.

One of skill in the art will appreciate that the present methods are useful in conjunction with a wide variety of sugar derivatives, which may include moieties that interfere with the reactions necessary to assemble the reactive sugar nucleus or modifying group. Such moieties can be protected from participating in the reaction by the presence of a protecting group. For examples of useful protecting groups, see, for example, Greene et al., PROTECTIVE GROUPS IN ORGANIC SYNTHESIS, John Wiley & Sons, New York, 1991.

For example, numerous methods are available for modifying galactose, glucose, N-acetylgalactosamine and fucose to name a few sugar substrates, which are readily modified by art recognized methods. See, for example, Elhalabi et al., Curr. Med. Chem. 6: 93 (1999); and Schafer et al., J. Org. Chem. 65: 24 (2000).

Those of skill in the art will appreciate that a variety of sugar moieties can be derivatized with modifying groups or activated with activating groups in a manner analogous to that set forth using the exemplary sugars and modifying groups set forth below. The discussion focuses on specific modifying groups and sugars for clarity of illustration. Those of skill will appreciate that the methods set forth herein are broadly applicable to the preparation of modified sugars, therefore, the discussion should not be interpreted as limiting the scope of the invention.

In an exemplary embodiment, the peptide that is modified by a method of the invention is a peptide that is produced in mammalian cells (e.g., CHO cells) or in a transgenic animal and thus, contains N- and/or O-linked oligosaccharide chains, which are incompletely sialylated. The oligosaccharide chains of the glycopeptide lacking a sialic acid and containing a terminal galactose residue can be PEGylated, PPGylated or otherwise modified with a modified sialic acid.

In Scheme 5, the mannosamine glycoside 1, is treated with the active ester of a protected amino acid (e.g., glycine) derivative, converting the sugar amine residue into the corresponding protected amino acid amide adduct. The adduct is treated with an aldolase to form the sialic acid 2. Compound 2 is subjected to catalytic hydrogenation of to produce compound 3. The amine introduced via formation of the glycine adduct is utilized as a locus of PEG or PPG attachment by reacting compound 3 with an activated PEG or PPG derivative (e.g., PEG-C(O)NHS, PPG-C(O)NHS), producing 4 or 5, respectively.

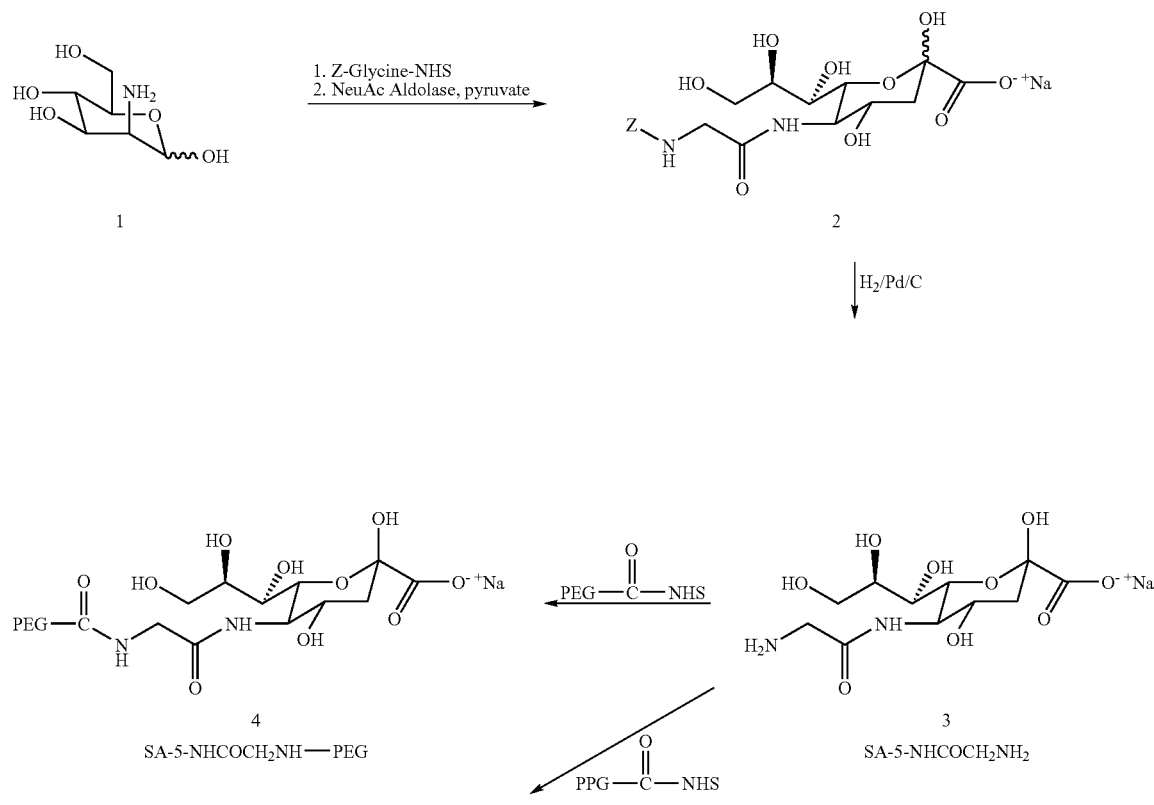

Scheme 5

Certain of the compounds prepared by the method of Scheme 5 are identified, for example, in Table 2. Other derivatives are prepared by art-recognized methods. See, for example, Keppler et al., *Glycobiology* 11: 11R (2001); and Charter et al., *Glycobiology* 10: 1049 (2000)). Other amine reactive PEG and PPG analogues are commercially available, or they can be prepared by methods readily accessible to those of skill in the art. The modified sugars of use in practicing the present invention can be substituted in any appropriate position.

Mannosamine may be acylated by the use of chloroacetic anhydride as set forth in Scheme 6.

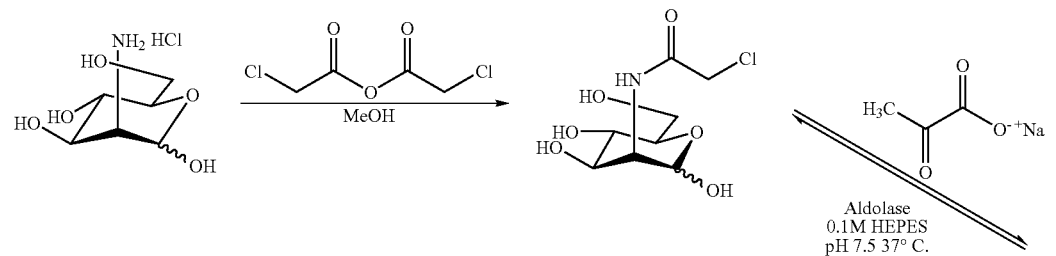

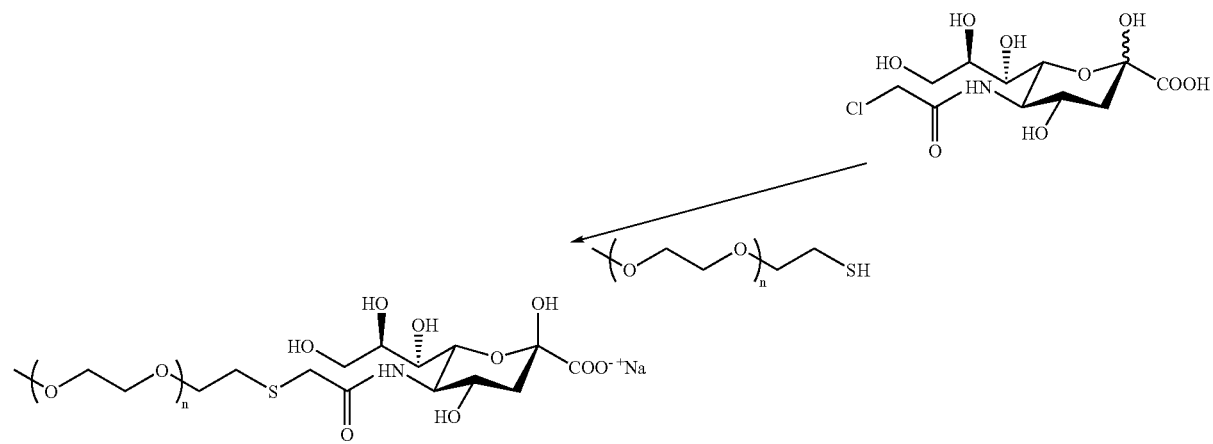

The resulting chloro-derivatized glycan is contacted with pyruvate in the presence of an aldolase, forming a chloro-derivatized sialic acid. The chloro group on the sialic acid moiety is then displaced with a nucleophilic PEG derivative, such as thio-PEG.

In another exemplary embodiment, as shown is Scheme 7, a mannosamine is acylated with a bis-HOPT dicarboxylate, producing the corresponding amido-alkyl-carboxylic acid, which is subsequently converted to a sialic acid derivative. The carboxylic acid is activated and reacted with a nucleophilic PEG derivative, such as amino-PEG.

Scheme 7

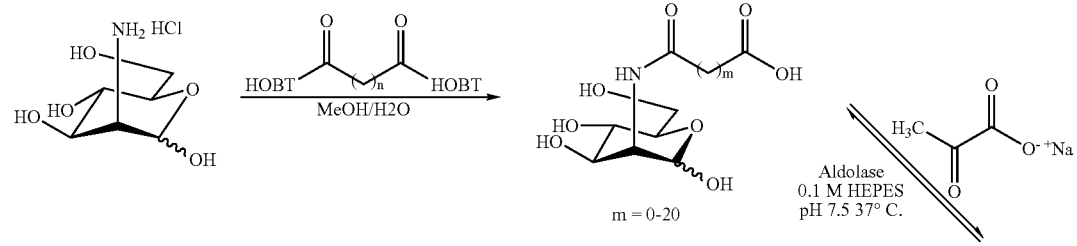

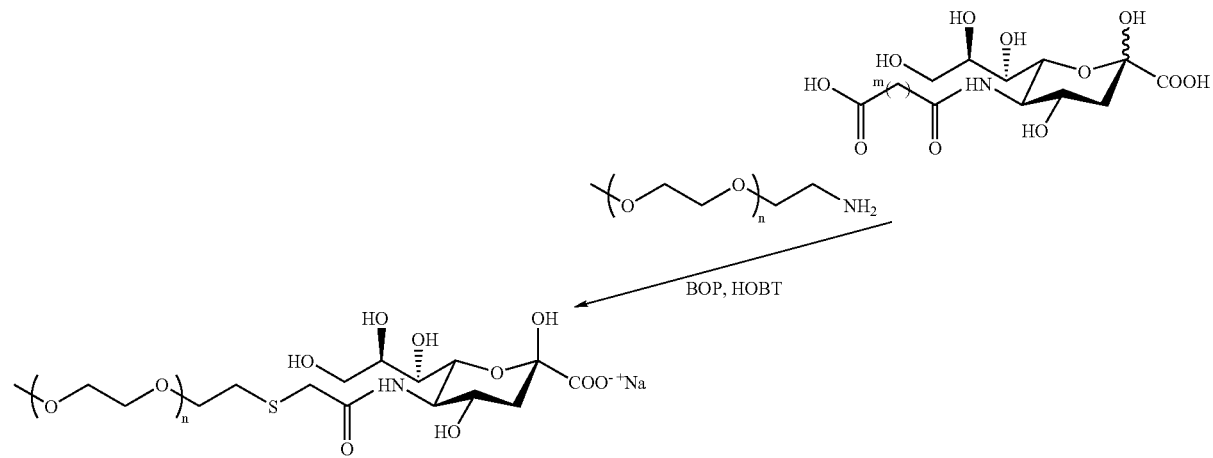

In another exemplary embodiment, set forth in Scheme 8, amine- and carboxyl-protected neuraminic acid is activated by converting the primary hydroxyl group to the corresponding p-toluenesulfonate ester, and the methyl ester is cleaved. The activating group is displaced by a nucleophilic PEG species, such as thio-PEG.

Scheme 10

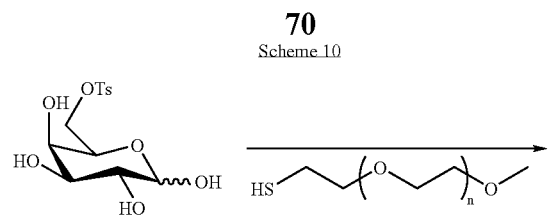

Scheme 8

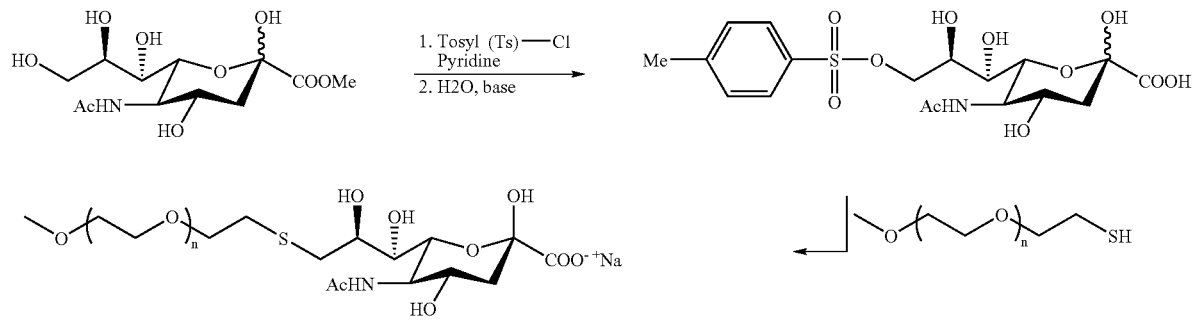

In yet a further exemplary embodiment, as set forth in Scheme 9, the primary hydroxyl moiety of an amine- and carboxyl-protected neuraminic acid derivative is alkylated using an electrophilic PEG, such as chloro-PEG. The methyl ester is subsequently cleaved to from the PEG-sugar.

-continued

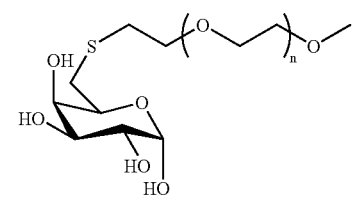

Scheme 11 sets forth an exemplary route for preparing a galactose-PEG derivative that is based upon a galactose-6-amine moiety.

Scheme 9

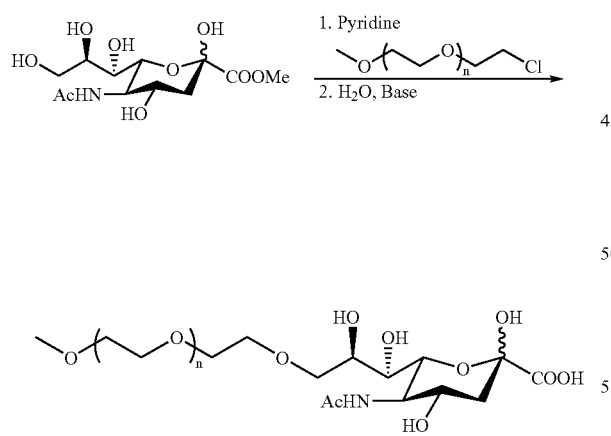

Scheme 11

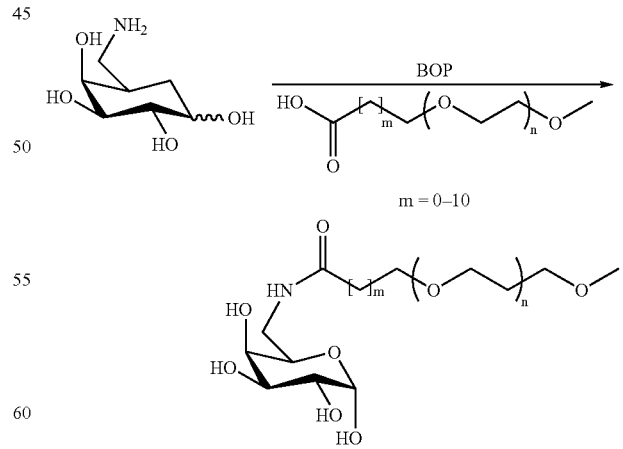

Glycans other than sialic acid can be derivatized with PEG using the methods set forth herein. The derivatized glycans, themselves, are also within the scope of the invention. Thus, Scheme 10 provides an exemplary synthetic route to a PEGylated galactose nucleotide sugar. The primary hydroxyl group of galactose is activated as the corresponding toluenesulfonate ester.

Scheme 12 provides another exemplary route to galactose derivatives. The starting point for Scheme 12 is galactose-2-amine, which is the locus for attaching a PEG derivative, such as methoxypoly(ethylene glycol) ("mPEG") carboxylic acid.

Scheme 12

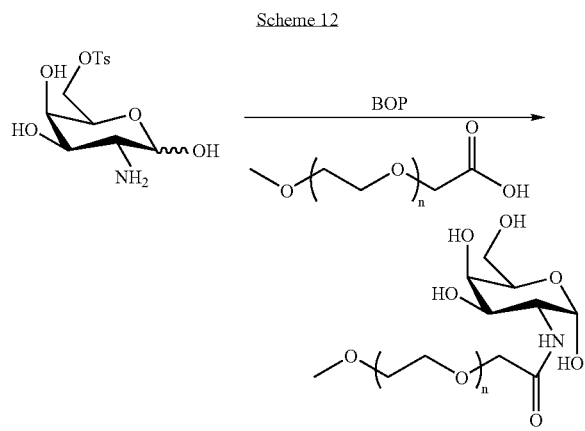

Exemplary modifying groups attached to the conjugates disclosed herein include, but are not limited to, PEG derivatives (e.g., acyl-PEG, acyl-alkyl-PEG, alkyl-acyl-PEG carbamoyl-PEG, aryl-PEG, alkyl-PEG), PPG derivatives (e.g., acyl-PPG, acyl-alkyl-PPG, alkyl-acyl-PPG carbamoyl-PPG, aryl-PPG), polyapartic acid, polyglutamate, polylysine, therapeutic moieties, diagnostic moieties, mannose-6-phosphate, heparin, heparan, SLe$^x$, mannose, mannose-6-phosphate, Sialyl Lewis X, FGF, VFGF, proteins (e.g., transferrin), chondroitin, keratan, dermatan, dextran, modified dextran, amylose, bisphosphate, poly-SA, hyaluronic acid, keritan, albumin, integrins, antennary oligosaccharides, peptides and the like. Methods of conjugating the various modifying groups to a saccharide moiety are readily accessible to those of skill in the art (POLY(ETHYLENE GLYCOL CHEMISTRY: BIOTECHNICAL AND BIOMEDICAL APPLICATIONS, J. Milton Harris, Ed., Plenum Pub. Corp., 1992; POLY (ETHYLENE GLYCOL) CHEMICAL AND BIOLOGICAL APPLICATIONS, J. Milton Harris, Ed., ACS Symposium Series No. 680, American Chemical Society, 1997; Hermanson, BIOCONJUGATE TECHNIQUES, Academic Press, San Diego, 1996; and Dunn et al., Eds. POLYMERIC DRUGS AND DRUG DELIVERY SYSTEMS, ACS Symposium Series Vol. 469, American Chemical Society, Washington, D.C. 1991).

The modified sugars produced by the above processes can be used without purification. However, it is usually preferred to recover the product. Standard, well-known techniques for recovery of glycosylated saccharides such as thin or thick layer chromatography, size exclusion chromatography, ion exchange chromatography, or membrane filtration can be used. It is preferred to use membrane filtration, more preferably utilizing a reverse osmotic membrane, or one or more column chromatographic techniques for the recovery as is discussed hereinafter and in the literature cited herein. For instance, membrane filtration wherein the membranes have molecular weight cutoff of about 3000 to about 10,000 can be used to remove proteins for reagents having a molecular weight of less than 10,000 Da. Membrane filtration or reverse osmosis can then be used to remove salts and/or purify the product saccharides (see, e.g., WO 98/15581). Nanofilter membranes are a class of reverse osmosis membranes that pass monovalent salts but retain polyvalent salts and uncharged solutes larger than about 100 to about 2,000 Daltons, depending upon the membrane used. Thus, in a typical application, saccharides prepared by the methods of the present invention will be retained in the membrane and contaminating salts will pass through.

A. Preparation of Modified Sugars with Crosslinking Reagents

In another embodiment, a crosslinking reagent is used to attach a modifying group to the sugar moiety. Typically, the crosslinking reagent is capable of forming a covalent bound with a reactive functional group on the sugar moiety and a modifying group to produce a modified sugar. In an exemplary embodiment, the cross linking reagent is a bifunctional compound. Useful bifunctional compounds include bifunctional poly(ethylene glycols), polyamides, polyethers, polyesters and the like. General approaches for linking carbohydrates to other molecules are known in the literature. See, for example, Lee et al., Biochemistry 28: 1856 (1989); Bhatia et al., Anal. Biochem. 178: 408 (1989); Janda et al., J. Am. Chem. Soc. 112: 8886 (1990) and Bednarski et al., WO 92/18135. In the discussion that follows is for clarity of illustration. Those of skill in the art will appreciate that the discussion is relevant to reactive groups on the modifying group as well.

An exemplary strategy involves incorporation of a protected sulfhydryl onto the sugar using the heterobifunctional crosslinker SPDP (n-succinimidyl-3-(2-pyridyldithio)propionate and then deprotecting the sulfhydryl for formation of a disulfide bond with another sulfhydryl on the modifying group.

If SPDP detrimentally affects the ability of the modified sugar to act as a glycosyltransferase substrate, one of an array of other crosslinkers such as 2-iminothiolane or N-succinimidyl S-acetylthioacetate (SATA) is used to form a disulfide bond. 2-iminothiolane reacts with primary amines, instantly incorporating an unprotected sulfhydryl onto the amine-containing molecule. SATA also reacts with primary amines, but incorporates a protected sulfhydryl, which is later deacetylated using hydroxylamine to produce a free sulfhydryl. In each case, the incorporated sulfhydryl is free to react with other sulfhydryls or protected sulfhydryl, like SPDP, forming the required disulfide bond.

In an exemplary embodiment, a bifunctional crosslinking reagent may be used to form a modified sugar containing a biomolecule modifying group such as a protein.

The above-described strategy is exemplary, and not limiting, of linkers of use in the invention. Other crosslinkers are available that can be used in different strategies for crosslinking the modifying group to the peptide. For example, TPCH (S-(2-thiopyridyl)-L-cysteine hydrazide and TPMPH ((S-(2-thiopyridyl) mercapto-propionohydrazide) react with carbohydrate moieties that have been previously oxidized by mild periodate treatment, thus forming a hydrazone bond between the hydrazide portion of the crosslinker and the periodate generated aldehydes. TPCH and TPMPH introduce a 2-pyridylthione protected sulfhydryl group onto the sugar, which can be deprotected with DTT and then subsequently used for conjugation, such as forming disulfide bonds between components.

If disulfide bonding is found unsuitable for producing stable modified sugars, other crosslinkers may be used that incorporate more stable bonds between components. The heterobifunctional crosslinkers GMBS (N-gamma-malimidobutyryloxy)succinimide) and SMCC (succinimidyl 4-(N-maleimido-methyl)cyclohexane) react with primary amines, thus introducing a maleimide group onto the component. The maleimide group can subsequently react with sulfhydryls on the other component, which can be introduced by previously mentioned crosslinkers, thus forming a stable thioether bond between the components. If steric hindrance between components interferes with either component's activity or the ability of the modified sugar to act as a glycosyltransferase substrate, crosslinkers can be used which introduce long spacer arms between components and include derivatives of some of the previously mentioned crosslinkers (i.e., SPDP). Thus, there is an abundance of suitable crosslinkers, which are useful; each of which is selected depending on the effects it has on optimal peptide conjugate and modified sugar production.

A variety of reagents are used to modify the components of the modified sugar with intramolecular chemical crosslinks (for reviews of crosslinking reagents and crosslinking procedures see: Wold, F., *Meth. Enzymol.* 25: 623-651, 1972; Weetall, H. H., and Cooney, D. A., In: ENZYMES AS DRUGS. (Holcenberg, and Roberts, eds.) pp. 395-442, Wiley, New York, 1981; Ji, T. H., *Meth. Enzymol.* 91: 580-609, 1983; Mattson et al., *Mol. Biol. Rep.* 17: 167-183, 1993, all of which are incorporated herein by reference). Preferred crosslinking reagents are derived from various zero-length, homo-bifunctional, and hetero-bifunctional crosslinking reagents. Zero-length crosslinking reagents include direct conjugation of two intrinsic chemical groups with no introduction of extrinsic material. Agents that catalyze formation of a disulfide bond belong to this category. Another example is reagents that induce condensation of a carboxyl and a primary amino group to form an amide bond such as carbodiimides, ethylchloroformate, Woodward's reagent K (2-ethyl-5-phenylisoxazolium-3'-sulfonate), and carbonyldiimidazole. In addition to these chemical reagents, the enzyme transglutaminase (glutamyl-peptide γ-glutamyltransferase; EC 2.3.2.13) may be used as zero-length crosslinking reagent. This enzyme catalyzes acyl transfer reactions at carboxamide groups of protein-bound glutaminyl residues, usually with a primary amino group as substrate. Preferred homo- and hetero-bifunctional reagents contain two identical or two dissimilar sites, respectively, which may be reactive for amino, sulfhydryl, guanidino, indole, or nonspecific groups.

A variety of crosslinking reagents are useful in conjunction with the current invention, including cleavable crosslinking reagents. Useful crosslinking reagents are further described in U.S. application Ser. No. 10/287,994, which is commonly owned by the same assignee and herein incorporated in its entirety by reference for all purposes.

6. Peptide Conjugates

Peptide conjugates of the present invention may have any appropriate number of modifying groups. As discussed above, the modifying groups may be linked via a glycosyl linking group directly to an amino acid on the peptide, to the growing glycan structure of the peptide, or present at the end of the glycan structure of the peptide. Thus, the modifying group may be present in any appropriate configuration within a glycan structure. For example, where the modified sugar is a modified sialic acid, the modified sialic acid will be incorporated into the glycan structure of a glycoprotein at any or all of the positions normally occupied by an unmodified sialic acid.

In an exemplary embodiment, the peptide conjugates of the invention have the general structure:

positive integer. In the general structure above, "Sugar" represents an unmodified sugar, "GLG" represents a glycosyl linking group, typically an intact glycosyl linking group, and "M" represents a modifying group. Each M, GLG, and sugar is optionally different.

In another exemplary embodiment, the peptide conjugates of the invention have the general structure:

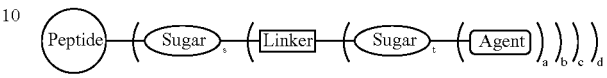

in which the symbols s, t, a, b, c, and d represent 0 or a positive integer. In the general structure above, "Sugar" represents an unmodified sugar and each sugar is optionally different.

As shown in the general structure above, peptide conjugates of the present invention may include multiple modifying groups that are optionally different. For example, the peptide conjugate may include a water-soluble polymer and/or a biomolecule and/or a therapeutic moiety.

In addition to providing methods of forming peptide conjugates through an enzymatically added glycosyl linking group, the methods of the present invention provide peptide conjugates that are highly homogenous in their substitution patterns. Using the methods of the invention, it is possible to form peptide conjugates in which essentially all of the modified sugar moieties across a population of conjugates of the invention are attached to multiple copies of a structurally identical amino acid or glycosyl residue. For example, the methods allow formation a peptide conjugate having a population of modifying groups, such as a population of water-soluble polymer moieties, which are covalently bound to the peptide through a glycosyl linking group. Essentially each member of the population is bound via the glycosyl linking group to a glycosyl residue of the peptide, where each glycosyl residue of the peptide to which the glycosyl linking group is bound has a homogenous substitution pattern. In other embodiments, essentially every member of the population of modifying groups is bound to an amino acid residue of the peptide via a glycosyl linking group, and each amino acid residue having a glycosyl linking group attached thereto has the same structure.

The methods of the invention also provide peptide conjugates having glycosyl linking groups that are mono- or multivalent (e.g., antennary structures). The methods may produce conjugates having glycosyl linking groups that are N-linked or O-linked glycans (e.g. originating from serine or threonine). Also included within the invention are methods of forming conjugates in which more than one selected modifying group is attached to a peptide via a multivalent glycosyl linking group. Thus, one or more proteins can be conjugated together to take advantage of their biophysical and biological properties.

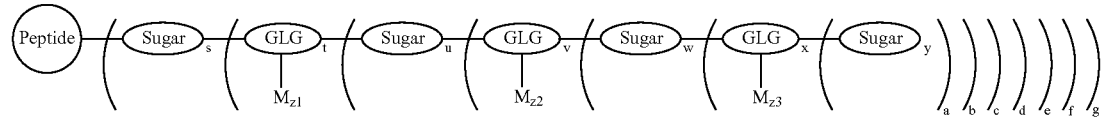

in which the symbols s, t, u, v, w, y, a, b, c, d, e, f, z1, z2, and z3 represent 0 or a positive integer and x and g represent a The peptide portion of the peptide conjugate may be any appropriate recombinant or endogenous cellular peptide. For example, peptides modified by the methods of the invention include members of the immunoglobulin family (e.g., antibodies, MHC molecules, T cell receptors, and the like), intercellular receptors (e.g., integrins, receptors for hormones or growth factors and the like) lectins, and cytokines (e.g., interleukins). Additional examples include tissue-type plasminogen activator (TPA), renin, clotting factors such as Factor VIII and Factor IX, bombesin, thrombin, hematopoietic growth factor, colony stimulating factors, viral antigens, complement peptides, α1-antitrypsin, erythropoietin, P-selectin glycopeptide ligand-1 (PSGL-1), granulocyte-macrophage colony stimulating factor, anti-thrombin III, interleukins, interferons, peptides A and C, fibrinogen, Herceptin™, leptin, glycosidases, among many others. This list of peptides is exemplary and should not be considered to be exclusive. Rather, as is apparent from the disclosure provided herein, the methods of the invention are applicable to any peptide in which a desired glycan structure can be fashioned. Other exemplary peptides are described in U.S. patent application Ser. No. 10/287,994, which is commonly owned by the same assignee and herein incorporated by reference in its entirety for all purposes.

In one embodiment, the peptides of use in the current invention are recombinant peptides expressed in the cell. Peptides may be modified (e.g. mutated) by methods known in the art, such as site-directed mutagenesis. For example, addition of glycosylation sites to a peptide or other structure is conveniently accomplished by altering the amino acid sequence such that it contains one or more glycosylation sites. Glycosylation of peptides is typically either N-linked or O-linked. An exemplary N-linkage is the attachment of the modified sugar to the side chain of an asparagine residue. The tripeptide sequences asparagine-X-serine and asparagine-X-threonine, where X is any amino acid except proline, are the recognition sequences for enzymatic attachment of a carbohydrate moiety to the asparagine side chain. Thus, the presence of either of these tripeptide sequences in a polypeptide creates a potential glycosylation site. O-linked glycosylation refers to the attachment of one sugar (e.g., N-aceylgalactosamine, galactose, mannose, GlcNAc, glucose, fucose or xylose) to a the hydroxy side chain of a hydroxyamino acid, preferably serine or threonine, although 5-hydroxyproline or 5-hydroxylysine may also be used. The addition may also be made by the incorporation of one or more species presenting an —OH group, preferably serine or threonine residues, within the sequence of the peptide (for O-linked glycosylation sites). The addition may be made by mutation of the peptide. The peptide amino acid sequence is preferably altered through changes at the DNA level, particularly by mutating the DNA encoding the peptide at preselected bases such that codons are generated that will translate into the desired amino acids.

The DNA mutation(s) are preferably made using methods known in the art. In an exemplary embodiment, the glycosylation site is added by shuffling polynucleotides. Polynucleotides encoding a candidate peptide can be modulated with DNA shuffling protocols. DNA shuffling is a process of recursive recombination and mutation, performed by random fragmentation of a pool of related genes, followed by reassembly of the fragments by a polymerase chain reaction-like process. See, e.g., Stemmer, *Proc. Natl. Acad. Sci. USA* 91:10747-10751 (1994); Stemmer, *Nature* 370:389-391 (1994); and U.S. Pat. Nos. 5,605,793, 5,837,458, 5,830,721 and 5,811,238. In another exemplary embodiment, the cell is transformed with the DNA encoding the peptide using standard methods known in the art.

In another embodiment, the peptides are not expressed in the cell but rather prepared outside of the cell and subsequently added to the intracellular space of the cell. In an exemplary embodiment, the peptide is chemically synthesized and added to the intracellular space of the cell by standard methods known in the art such as electroporation, microinjection, or addition of permeabilizing agents. In another exemplary embodiment, the peptide is harvested from a bacterial culture or mammalian organism and subsequently added to the intracellular space of the cell.

In another exemplary embodiment, the peptide contains a signal sequence. The signal sequence is typically a secretory signal sequence allowing the peptide to be excreted into the intercellular media, an endoplasmic reticulum signal sequence, or a Golgi signal sequence. One skilled in the art will recognize that the particular sequence will depend upon the cell. Exemplary signal sequences include Kre2 (Lussier et al., *J. Cell. Biol.* 131: 913-927 (1995)) and HDEL (Callewaert et al., *Biotechnology* 9: 378-379 (2001)).

In some embodiments, the peptide may be a therapeutic molecule. The natural form of the peptide may comprise complex N-linked glycans or may be a high mannose glycan. The peptide may be a mammalian peptide, and may be a human peptide. In some embodiments the peptide is selected from the group consisting of an immunoglobulin, erythropoietin, tissue-type activator peptide, or the like.

In an exemplary embodiment, the peptide is selected from those listed in Table 5. In another exemplary embodiment, the peptide is selected from those listed in Table 6.

TABLE 5

| Hormones and Growth Factors |
| --- |
| G-CSF |
| GM-CSF |
| TPO |
| EPO |
| EPO variants |
| FSH |
| HGH |
| insulin |
| alpha-TNF |
| Leptin |
| human chorionic gonadotropin |
| Enzymes and Inhibitors |
| TPA |
| TPA variants |
| Urokinase |
| Factors VII, VIII, IX, X |
| DNase |
| Glucocerebrosidase |
| Hirudin |
| α1 antitrypsin (α1 protease inhibitor) |
| Antithrombin III |
| Acid α-glucosidase (acid maltase) |
| α galactosidase A |
| α-L-iduronidase |
| Urokinase |
| Cytokines and Chimeric Cytokines |
| Interleukin-1 (IL-1), 1B, 2, 3, 4 |
| Interferon-alpha (IFN-alpha) |
| IFN-alpha-2b |
| IFN-beta |
| IFN-gamma |
| IFN-omega |
| Chimeric diphtheria toxin-IL-2 |

TABLE 5-continued

Receptors and Chimeric Receptors

CD4
Tumor Necrosis Factor receptor (TNF-R)
TNF-R:IgG Fc fusion
Alpha-CD20
PSGL-1
Complement
GlyCAM or its chimera
N-CAM or its chimera
Monoclonal Antibodies (Immunoglobulins)

MAb-anti-RSV
MAb-anti-IL-2 receptor
MAb-anti-CEA
MAb-anti-glycoprotein IIb/IIIa
MAb-anti-EGF
MAb-anti-Her2
MAb-CD20
MAb-alpha-CD3
MAb-TNFα
MAb-CD4
MAb-PSGL-1
Mab-anti F protein of Respiratory
Syncytial Virus
Anti-thrombin-III
Cells Red blood cells
White blood cells (e.g., T cells, B cells,
dendritic cells, macrophages, NK cells,
neutrophils, monocytes and the like)
Stem cells
Others
Hepatits B surface antigen (HbsAg)

TABLE 6

Alpha-galactosidase A
Alpha-L-iduronidase
Anti-thrombin-III
Granulocyte colony
stimulating factor (G-CSF)
Interferon α
Interferon β
Interferon omega
Factor VII clotting factor
Factor IX clotting factor
Follicle Stimulating Hormone (FSH)
Erythropoietin (EPO)
Granulocyte-macrophage colony
stimulating factor (GM-CSF)
Interferon γ
$\alpha_1$ protease inhibitor ($\alpha_1$ antitrypsin)
Tissue-type plasminogen activator (TPA)
Glucocerebrosidase (Cerezyme ™)
Interleukin-2 (IL-2)
Factor VIII
hrDNase
Insulin
Hepatitis B surface protein (HbsAg)
Human Growth Hormone (HGH)
Human chorionic gonadotropin
Urokinase
TNF receptor-IgG Fc fusion (Enbrel ™)
MAb-Her-2 (Herceptin ™)
MAb-F protein of Respiratory
Syncytial Virus (Synagis ™)
MAb-CD20 (Rituxan ™)
MAb-TNFα (Remicade ™)
MAb-Glycoprotein IIb/IIIa (Reopro ™)

7. Cells Including Peptide Conjugates

In a second aspect, the present invention provides a cell comprising a peptide conjugate. The peptide conjugate is formed using the methods of the invention described above.

In one aspect, the peptide conjugate comprises a covalent linkage between a modifying group and a glycosylated or non-glycosylated peptide. The modifying group is conjugated to said glycosylated or non-glycosylated peptide via a glycosyl linking group, (e.g., an intact glycosyl linking group) interposed between and covalently linked to both the peptide and said modifying group. In addition, exemplary modifying groups are members independently selected from the group consisting of polymers (e.g., water-soluble and -insoluble) therapeutic moieties, toxins, detectable labels, biomolecules (e.g., peptides), targeting moieties.

8. Cells for the Production of Peptide Conjugates

According to the present disclosure, the type of cell in which the peptide conjugate is produced may be relevant with respect to the desired glycosylation pattern (i.e. glycan structure) and/or location of the modifying group. For example, enzymatic synthetic reactions may be required in vitro to generate a peptide conjugate having desired glycosylation, depending on the structure of the glycan on the peptide produced by a particular cell type. However, the invention should in no way be construed to be limited to the production of peptide conjugates from any one particular cell type. A detailed discussion of glycosylation in several cell systems is presented in U.S. patent application Ser. No. 10/287,994, which is commonly owned by the same assignee and herein incorporated by reference in its entirety for all purposes. In addition, a review of host cell dependent glycosylation of peptides is presented in Kabata and Takasaki, "Structure and Biosynthesis of Cell Surface Carbohydrates," in Cell Surface Carbohydrates and Cell Development, 1991, pp. 1-24, Eds. Minoru Fukuda, CRC Press, Boca Raton, Fla.

The present invention encompasses methods of the production of peptide conjugates using endogenous peptides or recombinant peptides. In general, and to express a peptide from a nucleic acid encoding it, the nucleic acid must be incorporated into an expression cassette, comprising a promoter element, a terminator element, and the coding sequence of the peptide operably linked between the two. The expression cassette is then operably linked into a vector. Toward this end, adapters or linkers may be employed to join the nucleotide fragments or other manipulations may be involved to provide for convenient restriction sites, removal of superfluous nucleotides, removal of restriction sites, or the like. For this purpose, in vitro mutagenesis, primer repair, restriction, annealing, resubstitutions, e.g., transitions and transversions, may be involved. A shuttle vector has the genetic elements necessary for replication in a cell. Some vectors may be replicated only in prokaryotes, or may be replicated in both prokaryotes and eukaryotes. Such a plasmid expression vector will be maintained in one or more replication systems, preferably two replication systems, that allow for stable maintenance within a yeast host cell for expression purposes, and within a prokaryotic host for cloning purposes. Many vectors with diverse characteristics are now available commercially. Vectors are usually plasmids or phages, but may also be cosmids or mini-chromosomes. Conveniently, many commercially available vectors will have the promoter and terminator of the expression cassette already present, and a multi-linker site where the coding sequence for the peptide of interest can be inserted. The shuttle vector containing the expression cassette is then transformed in E. coli where it is replicated during cell division to generate a preparation of vector that is sufficient to transform the host cells of the chosen expression system. The above methodology is well know to those in the art, and protocols by which to accomplish can be found Sambrook et al. (2001, Molecular Cloning: A Laboratory Manual, Cold Spring Harbor Laboratory, New York).

The vector, once purified from the cells in which it is amplified, is then transformed into the cells of the expression system. The protocol for transformation depended on the kind of the cell and the nature of the vector. Transformants are grown in an appropriate nutrient medium, and, where appropriate, maintained under selective pressure to insure retention of endogenous DNA. Where expression is inducible, growth can be permitted of the yeast host to yield a high density of cells, and then expression is induced. The secreted, mature heterologous peptide can be harvested by any conventional means, and purified by chromatography, electrophoresis, dialysis, solvent-solvent extraction, and the like.

The techniques of molecular cloning are well-known in the art. Further, techniques for the procedures of molecular cloning can be found in Sambrook et al. (2001, Molecular Cloning: A Laboratory Manual, Cold Spring Harbor Laboratory Press, Cold Spring Harbor, N.Y.); Glover et al., (1985, DNA Cloning: A Practical Approach, Volumes I and II); Gait et al., (1985, Oligonucleotide Synthesis); Hames and Higgins (1985, Nucleic Acid Hybridization); Hames and Higgins (1984, Transcription And Translation); Freshney et al., (1986, Animal Cell Culture); Perbal, (1986, Immobilized Cells And Enzymes, IRL Press); Perbal, (1984, A Practical Guide To Molecular Cloning); Ausubel et al. (2002, Current Protocols in Molecular Biology, John Wiley & Sons, Inc.).

A wide variety of cells are useful in the present invention, including prokaryotic and eukaryotic cells (e.g. mammalian, insect, bacterial, fungal, and yeast cells).

Yeast and Fungal Cells

Exemplary yeast cells include ascosporogenous yeasts (Endomycetales), basidiosporogenous yeasts, and yeast belonging to the Fungi Imperfecti (Blastomycetes). The ascosporogenous yeasts are divided into two families, Spermophthoraceae and Saccharomycetaceae. The later is comprised of four subfamilies, Schizosaccharomycoideae (e.g., genus *Schizosaccharomyces*), Nadsonioideae, Lipomycoideae, and Saccharomycoideae (e.g., genera *Pichia, Kluyveromyces*, and *Saccharoniyces*). The basidiosporogenous yeasts include the genera *Leucosporidiuin, Rhodosporidiun, Sporidiobolus, Filobasidium*, and *Filobasidiella*. Yeast belonging to the Fungi Imperfecti are divided into two families, Sporoboloinycetaceae (e.g., genera *Sporobolomyces, Bullera*) and Cryptococcaceae (e.g., genus *Candida*). Of particular interest to the present invention are species within the genera *Saccharomyces, Pichia, Aspergillus, Trichoderna, Kluyveromyces*, especially *K. lactis* and *K. drosophiluin, Candida, Hansenula, Schizpsaccaromyces, Yarrowia*, and *Chiysoporium*. Since the classification of yeast may change in the future, for the purposes of this invention, yeast shall be defined as described in Skinner et al., eds. 1980) Biology and Activities of Yeast (Soc. App. Bacteriol. Symp. Series No. 9).

In addition to wild-type yeast and fungal cells, there are also strains of yeast and fungi that have been mutated and/or selected to enhance the level of expression of the exogenous gene, and the purity, the post-translational processing of the resulting peptide, and the recovery and purity of the mature peptide. Expression of an exogenous peptide may also be direct to the cell secretory pathway, as illustrated by the expression of insulin (see (Kjeldsen, 2000, Appl. Microbiol. Biotechnol. 54:277-286, and references cited therein). In general, to cause the exogenous peptide to be secreted from the yeast cell, secretion signals derived from yeast genes may be used, such as those of the genes of the killer toxin (Stark and Boyd, 1986, EMBO J. 5:1995-2002) or of the alpha pheromone (Kujan and Herskowitz, 1982, Cell 30:933; Brake et al., 1988, Yeast 4:S436).

Regarding the filamentous fingi in general, methods for genetic manipulation can be found in Kinghorn and Turner (1992, Applied Molecular Genetics of Filamentous Fungi, Blackie Academic and Professional, New York). Guidance on appropriate vectors can be found in Martinelli and Kinghorn (1994, Aspergillus: 50 years, Elsevier, Amsterdam).

Mammalian Cells

Any appropriate mammalian cell may be used to produce the peptide conjugates of the present invention. There are several mammalian cell lines that are particularly adept at expressing exogenous peptides. Typically mammalian cell lines originate from tumor cells extracted from mammals that have become immortalized, that is to say, they can replicate in culture essentially indefinitely. These cell lines include, but are not limited to, CHO (Chinese hamster ovary, e.g. CHO-K1; ATCC No. CCL 61) and variants thereof, NS0 (mouse myeloma), BNK, BHK 570 (ATCC No. CRL 10314), BHK (ATCC No. CRL 1632), Per.C6™ (immortalized human cells, Crucell N.V., Leiden, The Netherlands), COS-1 (ATCC No. CRL 1650), COS-7 (ATCC No. CRL 1651), HEK 293, mouse L cells, T lymphoid cell lines, BW5147 cells and MDCK (Madin-Darby canine kidney), HeLa (human), A549 (human lung carcinoma), 293 (ATCC No. CRL 1573; Graham et al., 1977, Gen. Virol. 36:59-72), BGMK (Buffalo Green Monkey kidney), Hep-2 (human epidermoid larynx carcinoma), LLC-MK$_2$ (African Green Monkey Kidney), McCoy, NCI-H292 (human pulmonary mucoepidermoid carcinoma tube), RD (rhabdomyosarcoma), Vero (African Green Monkey kidney), HEL (human embryonic lung), Human Fetal Lung-Chang, MRC5 (human embryonic lung), MRHF (human foreskin), and WI-38 (human embryonic lung). In some cases, the cells in which the therapeutic peptide is expressed may be cells derived from the patient to be treated, or they may be derived from another related or unrelated mammal. For example, fibroblast cells may be isolated from the mammal's skin tissue, and cultured and transformed in vitro. This technology is commercially available from Transkaryotic Therapies, Inc. (Cambridge, Mass.). Almost all currently used cell lines are available from the American Type Culture Collection (ATCC, Manassas, Va.) and BioWhittaker (Walkersville, Md.).

Mammalian cells may be transformed with DNA using any one of several techniques that are well known to those in the art. Such techniques include, but are not limited to, calcium phosphate transformation (Chen and Okayama, 1988; Graham and van der Eb, 1973; Corsaro and Pearson, 1981, Somatic Cell Genetics 7:603), Diethylaminoethyl (DEAE)-dextran transfection (Fujita et al., 1986; Lopata et al., 1984; Selden et al., 1986,), electroporation (Neumann et al., 1982,; Potter, 1988,; Potter et al., 1984,; Wong and Neuman, 1982), cationic lipid reagent transfection (Elroy-Stein and Moss, 1990; Feigner et al., 1987; Rose et al., 1991; Whitt et al., 1990; Hawley-Nelson et al., 1993, Focus 15:73; Ciccarone et al., 1993, Focus 15:80), retroviral (Cepko et al., 1984; Miller and Baltimore, 1986; Pear et al., 1993; Austin and Cepko, 1990; Bodine et al., 1991; Fekete and Cepko, 1993; Lemischka et al., 1986; Turner et al., 1990; Williams et al., 1984; Miller and Rosman, 1989, BioTechniques 7:980-90; Wang and Finer, 1996, Nature Med. 2:714-6), polybrene (Chaney et al, 1986; Kawai and Nishizawa, 1984), microinjection (Capecchi, 1980), and protoplast fusion (Rassoulzadegan et al., 1982; Sandri-Goldin et al., 1981; Schaffer, 1980), among others. In general, see Sambrook et al. (2001, Molecular Cloning: A Laboratory Manual, Cold Spring Harbor Laboratory, New York) and Ausubel et al. (2002, Current Protocols in Molecular Biology, John Wiley & Sons, New York) for transformation techniques.

Expression vectors useful for expressing exogenous peptides in mammalian cells are numerous, and are well known to those in the art. Many mammalian expression vectors are now commercially available from companies, including Novagen, Inc (Madison, Wis.), Gene Therapy Systems (San Diego, Calif.), Promega (Madison, Wis.), ClonTech Inc. (Palo Alto, Calif.), and Stratagene (La Jolla, Calif.), among others.

Insect Cells

Insect cell lines are also useful in the methods of the present invention. Insect cell lines of several different species origin are currently being used for peptide expression, and these lines are well known to those in the art. Insect cell lines of interest include, but are not limited to, dipteran and lepidopteran insect cells in general, Sf9 and variants thereof (fall armyworm *Spodoptera frugiperda*), *Estigmene acrea, Trichoplusia ni, Bombyx mori, Malacosoma disstri*. drosophila lines Kc1 and SL2 among others, and mosquito.

Baculovirus-mediated expression in insect cells has become particularly well-established for the production of recombinant peptides (Altmann et al., 1999, Glycoconjugate J. 16:109-123). With regard to peptide folding and post-translational processing, insect cells are second only to mammalian cell lines. Recently the baculovirus system, popular for transformation of insect cells, has been adapted for stable transformation of mammalian cells (see, for review, Koat and Condreay, 2002, Trends Biotechnol. 20:173-180, and references cited therein). The production of recombinant peptides in cultured mammalian cells is disclosed, for example, in U.S. Pat. Nos. 4,713,339, 4,784,950; 4,579,821; and 4,656,134. Several companies offer the services of transformation and culture of mammalian cells, including Cell Trends, Inc. (Middletown, Md.). Techniques for culturing mammalian cells are well known in the art, and further found in Hauser et al. (1997, *Mammalian Cell Biotechnology*, Walter de Gruyter, Inc., Hawthorne, N.Y.), and Sambrook et al. (2001, *Molecular Cloning: A Laboratory Manual*, Cold Spring Harbor and references cited therein.

Protocols for the use of baculovirus to transform insect cells are well known to those in the art. Several books have been published which provide the procedures to use the baculovirus system to express peptides in insect cells. These books include, but are not limited to, Richardson (Baculovirus Expression Protocols, 1998, Methods in Molecular Biology, Vol 39, Humana Pr), O'Reilly et al. (1994, Baculovirus Expression Vectors: A Laboratory Manual, Oxford Univ Press), and King and Possee (1992, The Baculovirus Expression System: A Laboratory Guide, Chapman & Hall). In addition, there are also publications such as Lucklow (1993, Curr. Opin. Biotechnol. 4:564-572) and Miller (1993, Curr. Opin. Genet. Dev. 3:97-101).

Many patents have also been issued that related to systems for baculoviral expression of foreign proteins. These patents include, but are not limited to, U.S. Pat. No. 6,210,966 (Culture medium for insect cells lacking glutamine and containing ammonium salt), U.S. Pat. No. 6,090,584 (Use of BVACs (BaculoVirus Artificial Chromosomes) to produce recombinant peptides), U.S. Pat. No. 5,871,986 (Use of a baculovirus to express a recombinant nucleic acid in a mammalian cell), U.S. Pat. No. 5,759,809 (Methods of expressing peptides in insect cells and methods of killing insects), U.S. Pat. No. 5,753,220 (Cysteine protease gene defective baculovirus, process for its production, and process for the production of economic peptide by using the same), U.S. Pat. No. 5,750,383 (Baculovirus cloning system), U.S. Pat. No. 5,731,182 (Non-mammalian DNA virus to express a recombinant nucleic acid in a mammalian cell), U.S. Pat. No. 5,728,580 (Methods and culture media for inducing single cell suspension in insect cell lines), U.S. Pat. No. 5,583,023 (Modified baculovirus, its preparation process and its application as a gene expression vector), U.S. Pat. No. 5,571,709 (Modified baculovirus and baculovirus expression vectors), U.S. Pat. No. 5,521,299 (Oligonucleotides for detection of baculovirus infection), U.S. Pat. No. 5,516,657 (Baculovirus vectors for expression of secretory and membrane-bound peptides), U.S. Pat. No. 5,475,090 (Gene encoding a peptide which enhances virus infection of host insects), U.S. Pat. No. 5,472,858 (Production of recombinant peptides in insect larvae), U.S. Pat. No. 5,348,886 (Method of producing recombinant eukaryotic viruses in bacteria), U.S. Pat. No. 5,322,774 (Prokaryotic leader sequence in recombinant baculovirus expression system), U.S. Pat. No. 5,278,050 (Method to improve the efficiency of processing and secretion of recombinant genes in insect systems), U.S. Pat. No. 5,244,805 (Baculovirus expression vectors), U.S. Pat. No. 5,229,293 (Recombinant baculovirus), U.S. Pat. No. 5,194,376 (Baculovirus expression system capable of producing recombinant peptides at high levels), U.S. Pat. No. 5,179,007 (Method and vector for the purification of recombinant peptides), U.S. Pat. No. 5,169,784 (Baculovirus dual promoter expression vector), U.S. Pat. No. 5,162,222 (Use of baculovirus early promoters for expression of recombinant nucleic acids in stably transformed insect cells or recombinant baculoviruses), U.S. Pat. No. 5,155,037 (Insect signal sequences useful to improve the efficiency of processing and secretion of recombinant nucleic acids in insect systems), U.S. Pat. No. 5,147,788 (Baculovirus vectors and methods of use), U.S. Pat. No. 5,110,729 (Method of producing peptides using baculovirus vectors in cultured cells), U.S. Pat. No. 5,077,214 (Use of baculovirus early promoters for expression of recombinant genes in stably transformed insect cells), U.S. Pat. No. 5,023,328 (Lepidopteran AKH signal sequence), and U.S. Pat. Nos. 4,879,236 and 4,745,051 (Method for producing a recombinant baculovirus expression vector). All of the aforementioned patents are incorporated in their entirety by reference herein.

Plant Cells

Many kinds of plants are amenable to transformation and expression of exogenous peptides. Plants of particular interest in making peptide conjugates include, for example, *Arabidopsis thalliana*, rapeseed (*Brassica* spp.; Ruiz and Blumwald, 2002, Planta 214:965-969)), soybean (*Glycine max*), sunflower (*Helianthus unnuus*), oil pahn (*Elaeis guineeis*), groundnut (peanut, *Arachis hypogaea*; Deng et al., 2001, Cell. Res. 11: 156-160), coconut (*Cocus nucifera*), castor (*Ricinus communes*), safflower (*Carthainus tinctorius*), mustard (*Brassica* spp. and *Sinapis alba*), coriander, (*Coriandrum sativum*), squash (*Cucurbita maxima*; Spencer and Snow, 2001, Heredity 86(Pt 6):694-702), linseed/flax (*Linum usitatissimum*; Lamblin et al., 2001, Physiol Plant 112:223-232), Brazil nut (*Bertholletia excelsa*), jojoba (*Simmondsia chinensis*), maize (*Zea mays*; Hood et al., 1999, Adv. Exp. Med. Biol. 464:127-147; Hood et al., 1997, Mol. Breed.

3:291-306; Petolino et al., 2000, Transgenic Research 9:1-9), alfalfa (Khoudi et al., 1999, Biotechnol. Bioeng. 64:135-143), tobacco (*Nicotiana tabacum*; Wright et al., Transgenic Res. 10:177-181; Frigerio et al., 2000, Plant Physiol. 123:1483-1493; Cramer et al., 1996, Ann. New York Acad. Sci. 792:62-8-71; Cabanes-Macheteau et al., 1999, Glycobiology 9:365-372; Ruggiero et al., 2000, FEBS Lett. 469:132-136), canola (Bai et al., 2001, Biotechnol. Prog. 17:168-174; Zhang et al., 2000, J. Anim. Sci. 78:2868-2878)), potato (Tacket et al., 1998, J. Infect. Dis. 182:302-305; Richter et al., 2000, Nat. Biotechnol. 18:1167-1171; Chong et al., 2000, Transgenic Res. 9:71-78), alfalfa (Wigdorovitz et al., 1999, Virology 255:347-353), Pea (Pisum sativum; Perrin et al., 2000, Mol. Breed. 6:345-352), rice (*Oryza sativa*; Stoger et al., 2000, Plant Mol. Biol. 42:583-590), cotton (*Gossypium hirsutum*; Kornyeyev et al., 2001, Physiol Plant 113:323-331), barley (*Hordeum vulgare*; Petersen et al., 2002, Plant Mol Biol 49:45-58); wheat (*Triticum* spp.; Pellegrineschi et al., 2002, Genome 45:421-430) and bean (*Vicia* spp.; Saalbach et al., 1994, Mol Gen Genet 242:226-236).

Transgenic plants are considered by many to be the expression system of choice for pharmaceutical peptides. Potentially, plants can provide a cheaper source of recombinant peptides. It has been estimated that the production costs of recombinant peptides in plants could be between 10 to 50 times lower that that of producing the same peptide in *E. coli*. While there are slight differences in the codon usage in plants as compared to animals, these can be compensated for by adjusting the recombinant DNA sequences (see, Kusnadi et al., 1997, Biotechnol. Bioeng. 56:473-484; Khoudi et al., 1999, Biotechnol. Bioeng. 135-143; Hood et al., 1999, Adv. Exp. Med. Biol. 464:127-147). In addition, peptide synthesis, secretion and post-translational modification are very similar in plants and animals, with only minor differences in plant glycosylation (see, Fischer et al., 2000, J. Biol. Regul. Homest. Agents 14: 83-92). Then, products from transgenic plants are also less likely to be contaminated by animal pathogens, microbial toxins and oncogenic sequences.

The expression of recombinant peptides in plant cells is well known in the art. In addition to transgenic plants, peptide conjugates can also be produced in transgenic plant cell cultures (Lee et al., 1997, Mol. Cell. 7:783-787), and non-transgenic plants inoculated with recombinant plant viruses. Several books have been published that describe protocols for the genetic transformation of plant cells: Potrykus (1995, Gene transfer to plants, Springer, New York), Nickoloff (1995, Plant cell electroporation and electrofusion protocols, Humana Press, Totowa, N.Y.) and Draper (1988, Plant genetic transformation, Oxford Press, Boston).

Several methods are currently used to stably transform plant cells with recombinant genetic material. These methods include, but are not limited to, *Agrobacterium* transformation (Bechtold and Pelletier, 1998; Escudero and Hohn, 1997; Hansen and Chilton, 1999; Touraev et al., 1997), biolistics (microprojectiles) (Finer et al., 1999; Hansen and Chilton, 1999; Shilito, 1999), electroporation of protoplasts (Fromm et al., 1985, Ou-Lee et al., 1986; Rhodes et al., 1988; Saunders et al., 1989; Trick et al., 1997), polyethylene glycol treatment (Shilito, 1999; Trick et al., 1997), in planta mircroinjection (Leduc et al., 1996; Zhou et al., 1983), seed imbibition (Trick et al., 1997), laser beam (1996), and silicon carbide whiskers (Thompson et al., 1995; U.S. Patent Appln. No. 20020100077, incorporated by reference herein in its entirety).

If expression of the recombinant nucleic acid is desired in a whole plant rather than in cultured cells, plant cells are first transformed with DNA encoding the peptide, following which, the plant is regenerated. This involves tissue culture procedures that are typically optimized for each plant species. Protocols to regenerate plants are already well known in the art for many species. Furthermore, protocols for other species can be developed by one of skill in the art using routine experimentation. Numerous laboratory manuals are available that describe procedures for plant regeneration, including but not limited to, Smith (2000, Plant tissue culture: techniques and experiments, Academic Press, San Diego), Bhojwani and Razdan (1996, Plant tissue culture: theory and practice, Elsevier Science Pub., Amsterdam), Islam (1996, Plant tissue culture, Oxford & IBH Pub. Co., New Delhi, India), Dodds and. Roberts (1995, Experiments in plant tissue culture, New York: Cambridge University Press, Cambridge England), Bhojwani (Plant tissue culture: applications and limitations, Elsevier, Amsterdam, 1990), Trigiano and Gray (2000, Plant tissue culture concepts and laboratory exercises, CRC Press, Boca Raton, Fla.), and Lindsey (1991, Plant tissue culture manual: fundamentals and applications, Kluwer Academic, Boston).

Bacteria

Numerous bacterial expression systems are known in the art. Preferred bacterial species include, but are not limited to, *E. coli*. and *Bacillus* species.

The expression of peptides in *E. coli* is well known in the art. Protocols for *E. coli*-based expression systems are found in U.S. Appln No. 20020064835, U.S. Pat. Nos. 6,245,539, 5,606,031, 5,420,027, 5,151,511, and RE33,653, among others. Methods to transform bacteria include, but are not limited to, calcium chloride (Cohen et al., 1972, Proc. Natl. Acad. Sci. U.S.A. 69:2110-2114; Hanahan, 1983, J. Mol. Biol. 166:557-580; Mandel and Higa, 1970, J. Mol. Biol. 53:159-162) and electroporation (Shigekawa and Dower, 1988, Biotechniques 6:742-751), and those described in Sambrook et al., 2001 (supra). For a review of laboratory protocols on microbial transformation and expression systems, see Saunders and Saunders (1987, Microbial Genetics Applied to Biotechnology: Principles and Techniques of Gene Transfer and Manipulation, Croom Helm, London), Pühler (1993, Genetic Engineering of Microorganisms, Weinheim, New York), Lee et al., (1999, Metabolic Engineering, Marcel Dekker, New York), Adolph (1996, Microbial Genome Methods, CRC Press, Boca Raton), and Birren and Lai (1996, Nonmammalian Genomic Analysis: A Practical Guide, Academic Press, San Diego), For a general review on the literature for peptide expression in *E. coli*, see Balbas (2001, Mol. Biotechnol. 19:251-267). Several companies now offer bacterial strains selected for the expression of mammalian peptides, such as the Rosetta™ strains of *E. coli* (Novagen, inc., Madison, Wis.; with enhanced expression of eukaryotic codons not normally used in bacteria cells, and enhanced disulfide bond formation). In an exemplary embodiment, peptides are expressed in K12 cells. In another exemplary embodiment, peptides are expressed in an *E. coli* cell selected from JM-101, JM-102, JM-103, JM-104, JM-105, JM-106, JM-107, JM-108, JM-109, and W3110 cells.

9. Enzymes

A. Glycosyltransferases

Glycosyltransferases of use in the present invention catalyze the addition of sugars and modified sugars (also referred to herein as donor sugars or donor modified sugars), in a step-wise fashion, to a protein, glycopeptide, lipid or glycolipid or to the non-reducing end of a growing oligosaccharide. N-linked glycopeptides are synthesized via a transferase and a lipid-linked oligosaccharide donor Dol-PP-NAG$_2$Glc$_3$Man$_9$ in an en block transfer followed by trimming of the core. In this case the nature of the "core" saccharide is somewhat different from subsequent attachments. A very large number of glycosyltransferases are known in the art.

The glycosyltransferase to be used in the present invention may be any as long as it can utilize the modified sugar as a sugar donor. Examples of such enzymes include Leloir pathway glycosyltransferase, such as galactosyltransferase, N-acetylglucosaminyltransferase, N-acetylgalactosaminyltransferase, fucosyltransferase, sialyltransferase, mannosyltransferase, xylosyltransferase, glucurononyltransferase and the like.

For enzymatic syntheses that involve glycosyltransferase reactions, glycosyltransferase may be cloned. Many cloned glycosyltransferases are known, as are their polynucleotide sequences. See, e.g., "The WWW Guide To Cloned Glycosyltransferases," (http://www.vei.co.uk/TGN/gt_guide.htm). Glycosyltransferase amino acid sequences and nucleotide sequences encoding glycosyltransferases from which the amino acid sequences can be deduced are also found in various publicly available databases, including GenBank, Swiss-Prot, EMBL, and others.

Glycosyltransferases that can be employed in the methods of the invention include, but are not limited to, galactosyltransferases, fucosyltransferases, glucosyltransferases, N-acetylgalactosaminyltransferases, N-acetylglucosaminyltransferases, glucuronyltransferases, sialyltransferases, mannosyltransferases, glucuronic acid transferases, galacturonic acid transferases, and oligosaccharyltransferases. Suitable glycosyltransferases include those derived from eukaryotes, as well as from prokaryotes.

DNA encoding the enzyme glycosyltransferases may be obtained by chemical synthesis, by screening reverse transcripts of mRNA from appropriate cells or cell line cultures, by screening genomic libraries from appropriate cells, or by combinations of these procedures. Screening of mRNA or genomic DNA may be carried out with oligonucleotide probes generated from the glycosyltransferases gene sequence. Probes may be labeled with a detectable group such as a fluorescent group, a radioactive atom or a chemiluminescent group in accordance with known procedures and used in conventional hybridization assays. In the alternative, glycosyltransferases gene sequences may be obtained by use of the polymerase chain reaction (PCR) procedure, with the PCR oligonucleotide primers being produced from the glycosyltransferases gene sequence. See, U.S. Pat. No. 4,683,195 to Mullis et al. and U.S. Pat. No. 4,683,202 to Mullis.

The glycosyltransferases enzyme may be synthesized in host cells transformed with vectors containing DNA encoding the glycosyltransferases enzyme. A vector is a replicable DNA construct. Vectors are used either to amplify DNA encoding the glycosyltransferases enzyme and/or to express DNA which encodes the glycosyltransferases enzyme. An expression vector is a replicable DNA construct in which a DNA sequence encoding the glycosyltransferases enzyme is operably linked to suitable control sequences capable of effecting the expression of the glycosyltransferases enzyme in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants.

i) Fucosyltransferases

In some embodiments, a glycosyltransferase used in the method of the invention is a fucosyltransferase. Fucosyltransferases are known to those of skill in the art. Exemplary fucosyltransferases include enzymes, which transfer L-fucose from GDP-fucose to a hydroxy position of an acceptor sugar. Fucosyltransferases that transfer non-nucleotide sugars to an acceptor are also of use in the present invention.

In some embodiments, the acceptor sugar is, for example, the GlcNAc in a Galβ(1→3,4)GlcNAcβ-group in an oligosaccharide glycoside. Suitable fucosyltransferases for this reaction include the Galβ(1→3,4)GlcNAcβ1-α(1→3,4)fucosyltransferase (FTIII E.C. No. 2.4.1.65), which was first characterized from human milk (see, Palcic, et al., *Carbohydrate Res.* 190: 1-11 (1989); Prieels, et al., *J. Biol. Chem.* 256: 10456-10463 (1981); and Nunez, et al., *Can. J. Chem.* 59: 2086-2095 (1981)) and the Galβ(1→4)GlcNAcβ-αfucosyltransferases (FTIV, FTV, FTVI) which are found in human serum. FTVII (E.C. No. 2.4.1.65), a sialyl α(2→3)Galβ ((1→3)GlcNAcβ fucosyltransferase, has also been characterized. A recombinant form of the Galβ(1→3,4) GlcNAcβ-α(1→3,4)fucosyltransferase has also been characterized (see, Dumas, et al., *Bioorg. Med. Letters* 1: 425-428 (1991) and Kukowska-Latallo, et al., *Genes and Development* 4: 1288-1303 (1990)). Other exemplary fucosyltransferases include, for example, α1,2 fucosyltransferase (E.C. No. 2.4.1.69). Enzymatic fucosylation can be carried out by the methods described in Mollicone, et al., *Eur. J. Biochem.* 191: 169-176 (1990) or U.S. Pat. No. 5,374,655. Cells that are used to produce a fucosyltransferase will also include an enzymatic system for synthesizing GDP-fucose.

ii) Galactosyltransferases

In another group of embodiments, the glycosyltransferase is a galactosyltransferase. Exemplary galactosyltransferases include α(1,3) galactosyltransferases (E.C. No. 2.4.1.151, see, e.g., Dabkowski et al., *Transplant Proc.* 25:2921 (1993) and Yamamoto et al. *Nature* 345: 229-233 (1990), bovine (GenBank j04989, Joziasse et al., *J. Biol. Chem.* 264: 14290-14297 (1989)), murine (GenBank m26925; Larsen et al., *Proc. Nat'l. Acad. Sci. USA* 86: 8227-8231 (1989)), porcine (GenBank L36152; Strahan et al., *Immunogenetics* 41: 101-105 (1995)). Another suitable α1,3 galactosyltransferase is that which is involved in synthesis of the blood group B antigen (EC 2.4.1.37, Yamamoto et al., *J. Biol. Chem.* 265: 1146-1151 (1990) (human)).

Also suitable for use in the methods of the invention are β(1,4) galactosyltransferases, which include, for example, EC 2.4.1.90 (LacNAc synthetase) and EC 2.4.1.22 (lactose synthetase) (bovine (D'Agostaro et al., *Eur. J. Biochein.* 183: 211-217 (1989)), human (Masri et al., *Biochem. Biophys. Res. Commun.* 157: 657-663 (1988)), murine (Nakazawa et al., J. Biochem. 104: 165-168 (1988)), as well as E.C. 2.4.1.38 and the ceramide galactosyltransferase (EC 2.4.1.45, Stahl et al., *J. Neurosci. Res.* 38: 234-242 (1994)). Other suitable galactosyltransferases include, for example, α1,2 galactosyltransferases (from e.g., *Schizosaccharomyces pombe*, Chapell et al., *Mol. Biol. Cell* 5: 519-528 (1994)).

The production of proteins such as the enzyme GalNAc T$_{I-XIV}$ from cloned genes by genetic engineering is well known. See, eg., U.S. Pat. No. 4,761,371. One method involves collection of sufficient samples, then the amino acid sequence of the enzyme is determined by N-terminal sequencing. This information is then used to isolate a cDNA clone encoding a full-length (membrane bound) transferase which upon expression in the insect cell line Sf9 resulted in the synthesis of a fully active enzyme. The acceptor specificity of the enzyme is then determined using a semiquantitative analysis of the amino acids surrounding known glycosylation sites in 16 different proteins followed by in vitro glycosylation studies of synthetic peptides. This work has demonstrated that certain amino acid residues are overrepresented in glycosylated peptide segments and that residues in specific positions surrounding glycosylated serine and threonine residues may have a more marked influence on acceptor efficiency than other amino acid moieties.

iii) Sialyltransferases

Sialyltransferases are another type of glycosyltransferase that is useful in the recombinant cells and reaction mixtures of the invention. Cells that produce recombinant sialyltransferases will also produce CMP-sialic acid, which is a sialic acid donor for sialyltransferases. Examples of sialyltransferases that are suitable for use in the present invention include ST3Gal III (e.g., a rat or human ST3Gal III), ST3Gal IV, ST3Gal I, ST6Gal I, ST3Gal V, ST6Gal II, ST6GalNAc I, ST6GalNAc II, and ST6GalNAc III (the sialyltransferase nomenclature used herein is as described in Tsuji et al., *Glycobiology* 6: v-xiv (1996)). An exemplary α(2,3)sialyltransferase referred to as α(2,3)sialyltransferase (EC 2.4.99.6) transfers sialic acid to the non-reducing terminal Gal of a Galβ1→3Glc disaccharide or glycoside. See, Van den Eijnden et al., *J. Biol. Chem.* 256: 3159 (1981), Weinstein et al., *J. Biol. Chem.* 257: 13845 (1982) and Wen et al., *J. Biol. Chem.* 267: 21011 (1992). Another exemplary α2,3-sialyltransferase (EC 2.4.99.4) transfers sialic acid to the non-reducing terminal Gal of the disaccharide or glycoside. see, Rearick et al., *J. Biol. Chem.* 254: 4444 (1979) and Gillespie et al., *J. Biol. Chem.* 267: 21004 (1992). Further exemplary enzymes include Gal-β-1,4-GlcNAc α-2,6 sialyltransferase (See, Kurosawa et al. *Eur. J. Biochem.* 219: 375-381 (1994)).

Preferably, for glycosylation of carbohydrates of glycopeptides the sialyltransferase will be able to transfer sialic acid or modified sialic acid to the sequence Galβ1,4GlcNAc-, the most common penultimate sequence underlying the terminal sialic acid on fully sialylated carbohydrate structures (see, Table 5).

TABLE 7

| Sialyltransferase | Source | Sequence(s) formed | Ref. |
|---|---|---|---|
| ST6Gal I | Mammalian | NeuAcI2,6Galβ1,4GlCNAc- | 1 |
| ST3Gal III | Mammalian | NeuAcI2,3Galβ1,4GlCNAc-<br>NeuAcI2,3Galβ1,3GlCNAc- | 1 |
| ST3Gal IV | Mammalian | NeuAcI2,3Galβ1,4GlCNAc-<br>NeuAcI2,3Galβ1,3GlCNAc- | 1 |
| ST6Gal II | Mammalian | NeuAcI2,6Galβ1,4GlCNA | |
| ST6Gal II | photobacterium | NeuAcI2,6Galβ1,4GlCNAc- | 2 |
| ST3Gal V | N. meningitides<br>N. gonorrhoeae | NeuAcI2,3Galβ1,4GlCNAc- | 3 |

1 Goochee et al., Bio/Technology 9: 1347-1355 (1991)
2 Yamamoto et al., J. Biochem. 120: 104-110 (1996)
3 Gilbert et al., J. Biol. Chem. 271: 28271-28276 (1996)

An example of a sialyltransferase that is useful in the claimed methods is ST3Gal III, which is also referred to as α(2,3)sialyltransferase (EC 2.4.99.6). This enzyme catalyzes the transfer of sialic acid or modified sialic acid to the Gal of a Galβ1,3GlcNAc or Galβ1,4GlcNAc glycoside (see, e.g., Wen et al., *J. Biol. Chem.* 267: 21011 (1992); Van den Eijnden et al., *J. Biol. Chem.* 256: 3159 (1991)) and is responsible for sialylation of asparagine-linked oligosaccharides in glycopeptides. The modified sialic acid is linked to a Gal with the formation of an α-linkage between the two saccharides. Bonding (linkage) between the saccharides is between the 2-position of NeuAc and the 3-position of Gal. This particular enzyme can be isolated from rat liver (Weinstein et al., *J. Biol. Chem.* 257: 13845 (1982)); the human cDNA (Sasaki et al. (1993) *J. Biol. Chem.* 268: 22782-22787; Kitagawa & Paulson (1994) *J. Biol. Chem.* 269: 1394-1401) and genomic (Kitagawa et al. (1996) *J. Biol. Chem.* 271: 931-938) DNA sequences are known, facilitating production of this enzyme by recombinant expression. In an exemplary embodiment, the sialylation methods use a rat ST3Gal III.

Other exemplary sialyltransferases of use in the present invention include those isolated from *Campylobacter jejuni*, including the α(2,3). See, e.g, WO99/49051.

Sialyltransferases other than those listed in Table 4, are also useful in an economic and efficient large-scale process for sialylation of commercially important glycopeptides. As a simple test to find out the utility of these other enzymes, various amounts of each enzyme (1-100 mU/mg protein) are reacted with asialo-$\alpha_1$ AGP (at 1-10 mg/ml) to compare the ability of the sialyltransferase of interest to sialylate glycopeptides relative to either bovine ST6Gal I, ST3Gal III or both sialyltransferases. Alternatively, other glycopeptides, or N-linked oligosaccharides enzymatically released from the peptide backbone can be used in place of asialo-$\alpha_1$ AGP for this evaluation. In addition, sialyltransferases may be tested in vitro for their ability to transfer a modified sialic acid to a peptide of glycopeptide. One skill in the art will immediately recognize that similarly assays may be use for any of appropriate glycosyltransferases. Sialyltransferases with the ability to sialylate N-linked oligosaccharides of glycopeptides more efficiently than ST6Gal I are useful in a practical large-scale process for peptide sialylation (as illustrated for ST3Gal III in this disclosure).

iv) Other Glycosyltransferases

One of skill in the art will understand that other glycosyltransferases can be substituted into similar transferase cycles as have been described in detail for the sialyltransferase. In particular, the glycosyltransferase can also be, for instance, glucosyltransferases, e.g., Alg8 (Stagljov et al., *Proc. Natl. Acad. Sci. USA* 91: 5977 (1994)) or Alg5 (Heesen et al., *Eur. J. Biochem.* 224: 71 (1994)).

N-acetylgalactosaminyltransferases are also of use in practicing the present invention. Suitable N-acetylgalactosaminyltransferases include, but are not limited to, α(1,3) N-acetylgalactosaminyltransferase, β(1,4) N-acetylgalactosaminyltransferases (Nagata et al., *J. Biol. Chem.* 267: 12082-12089 (1992) and Smith et al., *J. Biol Chem.* 269: 15162 (1994)) and polypeptide N-acetylgalactosaminyltransferase (Homa et al., *J. Biol. Chem.* 268: 12609 (1993)). Suitable N-acetylglucosaminyltransferases include GnTI (2.4.1.101, Hull et al., *BBRC* 176: 608 (1991)), GnTII, GnTIII (Ihara et al., *J. Biochem.* 113: 692 (1993)), GnTIV, and GnTV (Shoreiban et al., *J. Biol. Chem.* 268: 15381 (1993)), O-linked N-acetylglucosaminyltransferase (Bierhuizen et al., *Proc. Natl. Acad. Sci. USA* 89: 9326 (1992)), N-acetylglucosamine-1-phosphate transferase (Rajput et al., *Biochem J.* 285: 985 (1992), and hyaluronan synthase.

Mannosyltransferases are of use to transfer modified mannose moieties. Suitable mannosyltransferases include α(1,2) mannosyltransferase, α(1,3) mannosyltransferase, α(1,6) mannosyltransferase, β(1,4) mannosyltransferase, Dol-P-Man synthase, OCh1, and Pmt1 (see, Kornfeld et al., *Annu. Rev. Biochem.* 54: 631-664 (1985)).

Xylosyltransferases are also useful in the present invention. See, for example, Rodgers, et al., Biochem. J., 288:817-822 (1992); and Elbain, et al., U.S. Pat. No. 6,168,937.

Other suitable glycosyltransferase cycles are described in Ichikawa et al., *JACS* 114: 9283 (1992), Wong et al., *J. Org. Chem.* 57: 4343 (1992), and Ichikawa et al. in CARBOHYDRATES AND CARBOHYDRATE POLYMERS. Yaltami, ed. (ATL Press, 1993).

Prokaryotic glycosyltransferases are also useful in practicing the invention. Such glycosyltransferases include enzymes involved in synthesis of lipooligosaccharides (LOS), which are produced by many gram negative bacteria. The LOS typically have terminal glycan sequences that mimic glycoconjugates found on the surface of human epithelial cells or in host secretions (Preston et al., *Critical Reviews in Microbiology* 23(3): 139-180 (1996)). Such enzymes include, but are not limited to, the proteins of the rfa operons of species such as *E. coli* and *Salmonella typhimurium*, which include a β1,6 galactosyltransferase and a β1,3 galactosyltransferase (see, e.g., EMBL Accession Nos. M80599 and M86935 (*E. coli*); EMBL Accession No. S56361 (*S. typhimurium*)), a glucosyltransferase (Swiss-Prot Accession No. P25740 (*E. coli*), an β1,2-glucosyltransferase (rfaJ)(Swiss-Prot Accession No. P27129 (*E. coli*) and Swiss-Prot Accession No. P19817 (*S. typhimurium*)), and an β1,2-N-acetylglucosaminyltransferase (rfaK)(EMBL Accession No. U00039 (*E. coli*). Other glycosyltransferases for which amino acid sequences are known include those that are encoded by operons such as rfaB, which have been characterized in organisms such as *Klebsiella pneumoniae, E. coli, Salmonella typhimurium, Salmonella enterica, Yersinia enterocolitica, Mycobacterium leprosum*, and the rh1 operon of *Pseudomonas aeruginosa*.

Also suitable for use in the present invention are glycosyltransferases that are involved in producing structures containing lacto-N-neotetraose, D-galactosyl-β-1,4-N-acetyl-D-glucosaminyl-β-1,3-D-galactosyl-β-1,4-D-glucose, and the $P^k$ blood group trisaccharide sequence, D-galactosyl-α-1,4-D-galactosyl-β-1,4-D-glucose, which have been identified in the LOS of the mucosal pathogens *Neisseria gonnorhoeae* and *N. meningitidis* (Scholten et al., *J. Med. Microbiol.* 41: 236-243 (1994)). The genes from *N. meningitidis* and *N. gonorrhoeae* that encode the glycosyltransferases involved in the biosynthesis of these structures have been identified from *N. meningitidis* immunotypes L3 and L1 (Jennings et al., *Mol. Microbiol.* 18: 729-740 (1995)) and the *N. gonorrhoeae* mutant F62 (Gotshlich, *J. Exp. Med.* 180: 2181-2190 (1994)). In *N. meningitidis*, a locus consisting of three genes, lgtA, lgtB and lg E, encodes the glycosyltransferase enzymes required for addition of the last three of the sugars in the lacto-N-neotetraose chain (Wakarchuk et al., *J. Biol. Chem.* 271: 19166-73 (1996)). Recently the enzymatic activity of the lgtB and lgtA gene product was demonstrated, providing the first direct evidence for their proposed glycosyltransferase function (Wakarchuk et al., *J. Biol. Chem.* 271(45): 28271-276 (1996)). In *N. gonorrhoeae*, there are two additional genes, lgtD which adds β-D-GalNAc to the 3 position of the terminal galactose of the lacto-N-neotetraose structure and lgtC which adds a terminal α-D-Gal to the lactose element of a truncated LOS, thus creating the $P^k$ blood group antigen structure (Gotshlich (1994), supra.). In *N. meningitidis*, a separate immunotype L1 also expresses the $P^k$ blood group antigen and has been shown to carry an lgtC gene (Jennings et al., (1995), supra.). *Neisseria* glycosyltransferases and associated genes are also described in U.S. Pat. No. 5,545,553 (Gotschlich). Genes for α1,2-fucosyltransferase and α1,3-fucosyltransferase from *Helicobacter pylori* has also been characterized (Martin et al., *J. Biol. Chem.* 272: 21349-21356 (1997)). Also of use in the present invention are the glycosyltransferases of *Campylobacter jejuni* (see, for example, http://afmb.cnrs-mrs.fr/~pedro/CAZY/gtf_42.html).

B. Sulfotransferases

In some embodiments, the invention also provides methods for producing peptides that include sulfated molecules, including, for example sulfated polysaccharides such as heparin, heparan sulfate, carragenen, and related compounds. Suitable sulfotransferases include, for example, chondroitin-6-sulphotransferase (chicken cDNA described by Fukuta et al., *J. Biol. Chem.* 270: 18575-18580 (1995); GenBank Accession No. D49915), glycosaminoglycan N-acetylglucosamine N-deacetylase/N-sulphotransferase 1 (Dixon et al., *Genomics* 26: 239-241 (1995); UL18918), and glycosaminoglycan N-acetylglucosamine N-deacetylase/N-sulphotransferase 2 (murine cDNA described in Orellana et al., *J. Biol. Chem.* 269: 2270-2276 (1994) and Eriksson et al., *J. Biol. Chem.* 269: 10438-10443 (1994); human cDNA described in GenBank Accession No. U2304).

C. Cell-Bound Glycosyltransferases

In another embodiment, the enzymes utilized in the method of the invention are membrane-bound glycosyltransferases. Although many soluble glycosyltransferases are known (see, for example, U.S. Pat. No. 5,032,519), glycosyltransferases are generally in membrane-bound form when associated with cells. Many of the membrane-bound enzymes studied thus far are considered to be intrinsic proteins; that is, they are not released from the membranes by sonication and require detergents for solubilization. Surface glycosyltransferases have been identified on the surfaces of vertebrate and invertebrate cells, and it has also been recognized that these surface transferases maintain catalytic activity under physiological conditions. However, the more recognized function of cell surface glycosyltransferases is for intercellular recognition (Roth, MOLECULAR APPROACHES to SUPRACELLULAR PHENOMENA, 1990).

Methods have been developed to alter the glycosyltransferases expressed by cells. For example, Larsen et al., *Proc. Natl. Acad. Sci. USA* 86: 8227-8231 (1989), report a genetic approach to isolate cloned cDNA sequences that determine expression of cell surface oligosaccharide structures and their cognate glycosyltransferases. A cDNA library generated from mRNA isolated from a murine cell line known to express UDP-galactose:.β.-D-galactosyl-1,4-N-acetyl-D-glucosaminide α-1,3-galactosyltransferase was transfected into COS-1 cells. The transfected cells were then cultured and assayed for α1-3 galactosyltransferase activity.

Francisco et al., *Proc. Natl. Acad. Sci. USA* 89: 2713-2717 (1992), disclose a method of anchoring β-lactamase to the external surface of *Escherichia coli*. A tripartite fusion consisting of (i) a signal sequence of an outer membrane protein, (ii) a membrane-spanning section of an outer membrane protein, and (iii) a complete mature β-lactamase sequence is produced resulting in an active surface bound β-lactamase molecule. However, the Francisco method is limited only to procaryotic cell systems and as recognized by the authors, requires the complete tripartite fusion for proper functioning.

D. Fusion Proteins

In other exemplary embodiments, the methods of the invention utilize fusion proteins that have more than one enzymatic activity that is involved in synthesis of a desired glycopeptide conjugate. The fusion polypeptides can be composed of, for example, a catalytically active domain of a glycosyltransferase that is joined to a catalytically active domain of an accessory enzyme. The accessory enzyme catalytic domain can, for example, catalyze a step in the formation of a nucleotide sugar that is a donor for the glycosyltransferase, or catalyze a reaction involved in a glycosyltransferase cycle. For example, a polynucleotide that encodes a glycosyltransferase can be joined, in-frame, to a polynucleotide that encodes an enzyme involved in nucleotide sugar synthesis. The resulting fusion protein can then catalyze not only the synthesis of the nucleotide sugar, but also the transfer of the sugar moiety to the acceptor molecule. The fusion protein can be two or more cycle enzymes linked into one expressible nucleotide sequence. In other embodiments the fusion protein includes the catalytically active domains of two or more glycosyltransferases. See, for example, U.S. Pat. No. 5,641,668. The modified glycopeptides of the present invention can be readily designed and manufactured utilizing various suitable fusion proteins (see, for example, PCT Patent Application PCT/CA98/01180, which was published as WO 99/31224 on Jun. 24, 1999.)

The terms and expressions which have been employed herein are used as terms of description and not of limitation, and there is no intention in the use of such terms and expressions of excluding equivalents of the features shown and described, or portions thereof, it being recognized that various modifications are possible within the scope of the invention claimed. Moreover, any one or more features of any embodiment of the invention may be combined with any one or more other features of any other embodiment of the invention, without departing from the scope of the invention. For example, the features of peptide conjugates, modifying groups, and modified sugars are applicable to the methods of the invention as well as cell compositions including peptide conjugates described herein. All publications, patents, and patent applications cited herein are hereby incorporated by reference in their entirety for all purposes.

EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Example 1

Example 1 describes the formation of a peptide conjugate using a sialic acid modified with polyethylene glycol (FIG. 1).

Sialic acid-5-PEG is incubated with the cell under conditions in which the cell internalizes the sialic acid-5-PEG. The SA-5-PEG is intracellularly contacted with CMP-SA-synthetase and CTP to form the modified nucleotide sugar CMP-SA-5-PEG. The CMP-SA-5-PEG is then intracellularly contacted with a glycosylated secretory peptide and the appropriate sialyl transferase to form the secretory peptide conjugate peptide-SA-5-PEG. The peptide-SA-5-PEG is secreted into the extracellular space and isolated by standard methods.

Example 2

Figure 2:
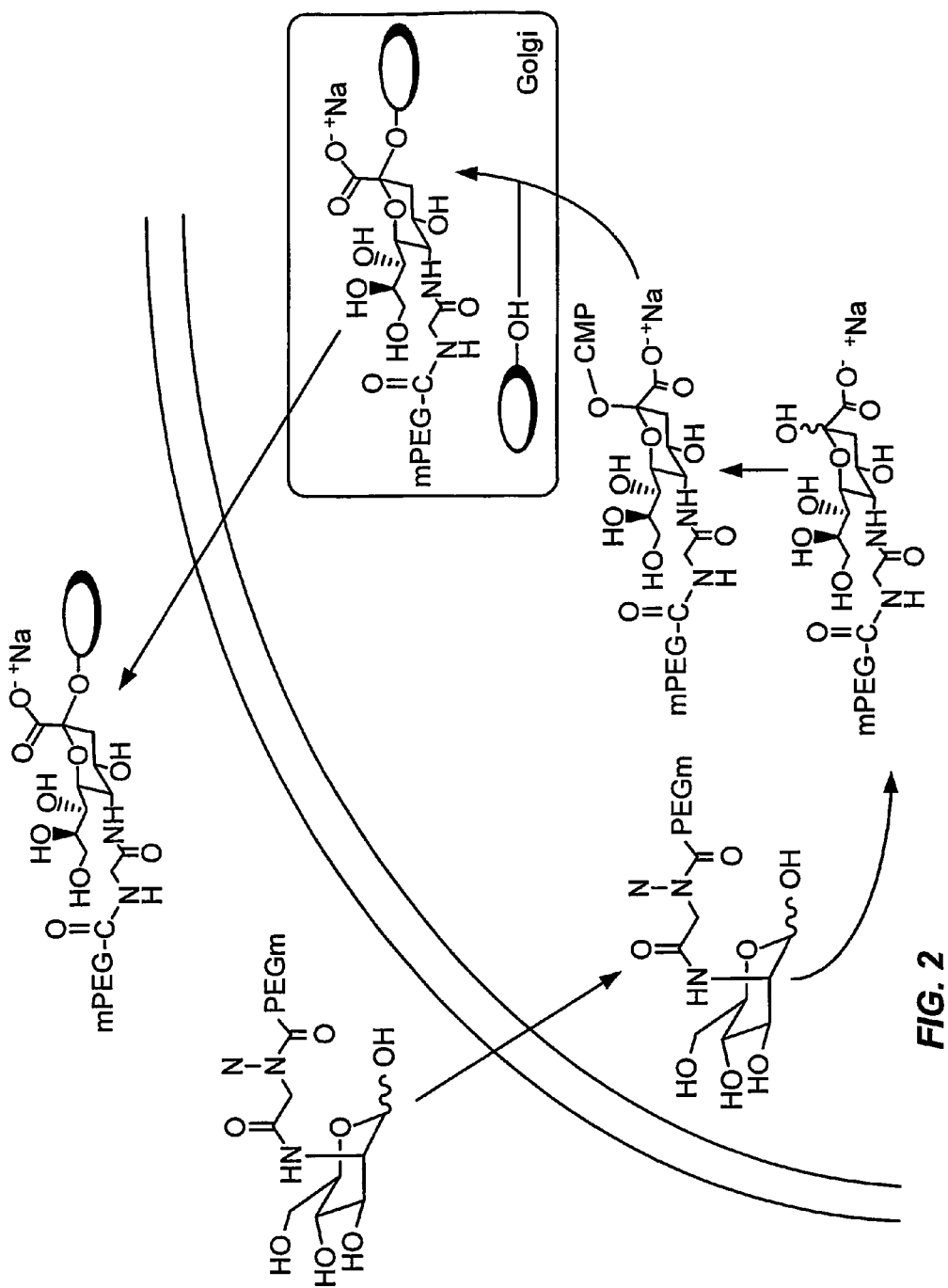
FIG. 2 is an illustration of the formation of a peptide conjugate using a mannosamine modified with polyethylene glycol.

Example 2 describes the formation of a peptide conjugate using a mannosamine modified with polyethylene glycol (FIG. 2).

Mannosamine-2-PEG is incubated with the cell under conditions in which the cell internalizes the mannosamine-2-PEG. The incubation was performed prior to induction of the glycosylated secretory peptide to allow the intracellular concentration of mannosamine-2-PEG to increase. The mannosamine-2-PEG is converted to the corresponding sialic acid-5-PEG with cellular enzymes. The sialic acid-5-PEG is intracellularly contacted with CMP-SA-synthetase and CTP to form the modified nucleotide sugar CMP-SA-5-PEG. The CMP-SA-5-PEG is then intracellularly contacted with a glycosylated secretory peptide and the appropriate sialyl transferase to form the secretory peptide conjugate peptide-SA-5-PEG. The peptide-SA-5-PEG is secreted into the extracellular space and isolated by standard methods.

Example 3

Figure 3:
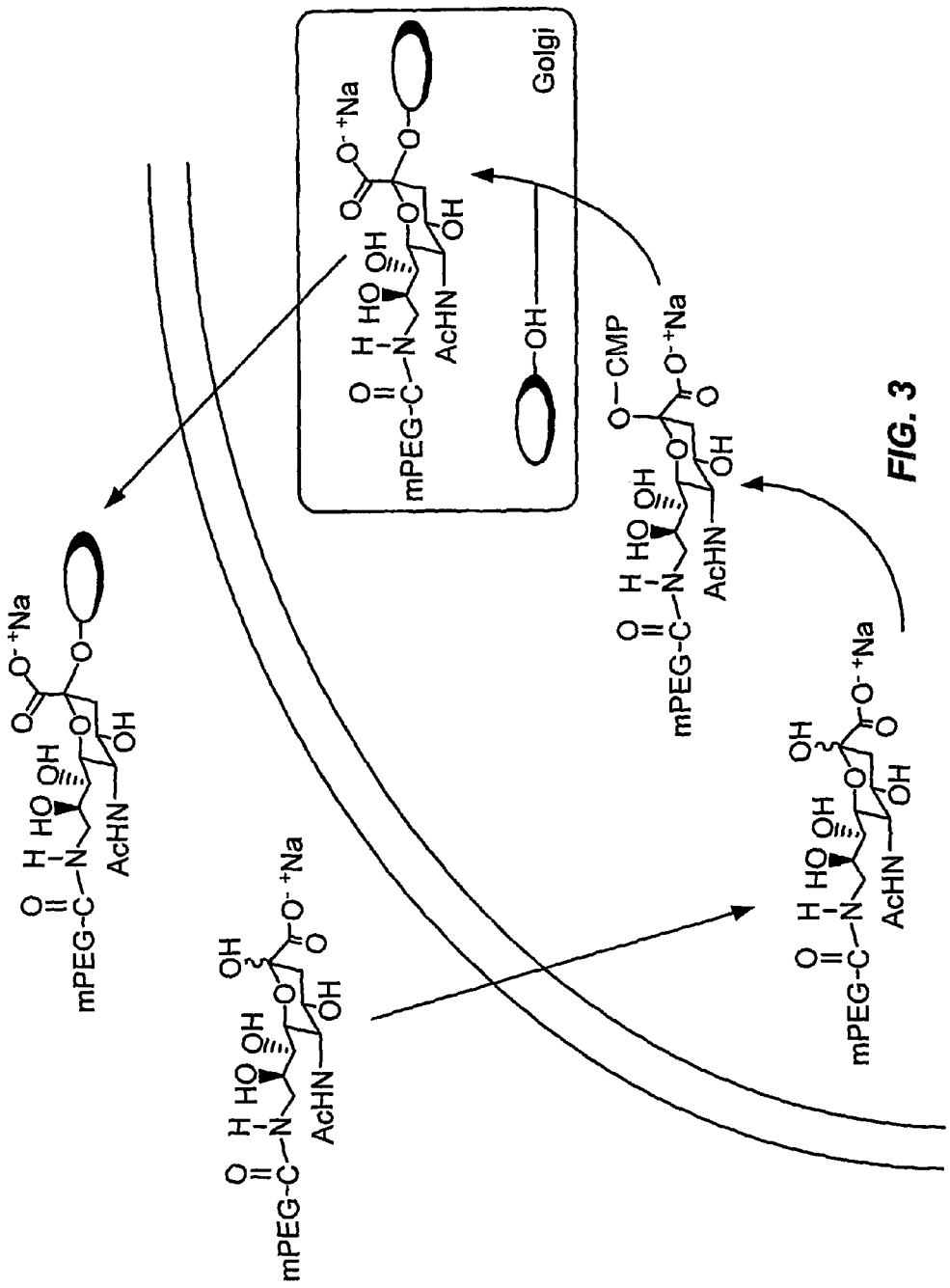
FIG. 3 is an illustration of the formation of a peptide conjugate using a sialic acid modified with polyethylene glycol

Example 3 describes the formation of a peptide conjugate using a sialic acid modified with polyethylene glycol (FIG. 3).

Sialic acid-9-PEG is incubated with the cell under conditions in which the cell internalizes the sialic acid-9-PEG. The SA-9-PEG is intracellularly contacted with CMP-SA-synthetase and CTP to form the modified nucleotide sugar CMP-SA-9-PEG. The CMP-SA-9-PEG is then intracellularly contacted with a glycosylated secretory peptide and the appropriate sialyl transferase to form the secretory peptide conjugate peptide-SA-5-PEG. The peptide-SA-5-PEG is secreted into the extracellular space and isolated by standard methods.

What is claimed is:

1. A method of forming a peptide conjugate comprising a covalent linkage between a modifying group and a glycosylated or non-glycosylated peptide, wherein said modifying group is conjugated to the peptide via a glycosyl linking group interposed between and covalently linked to both said peptide and said modifying group, said method comprising:
   a. contacting a cell with a modified sugar comprising a sialic acid moiety covalently functionalized with at least one modifying group, wherein said at least one modifying group is a water-soluble polymer;
   b. incubating said cell under conditions in which said cell internalizes said modified sugar;
   c. after step b, intracellularly contacting said modified sugar with a glycosylated or non-glycosylated peptide and a glycosyltransferase for which said modified sugar is a substrate, thereby forming said peptide conjugate.

2. The method of claim 1, further comprising, after step b and before step c, intracellularly contacting said modified sugar with a nucleotide and a nucleotidyl transferase, thereby forming a modified nucleotide sugar, wherein
   said modified sugar in step c is said modified nucleotide sugar.

3. The method of claim 1, further comprising isolating said peptide conjugate.

4. The method of claim 1, wherein said modified sugar is a modified nucleotide sugar.

5. The method of claim 1, wherein said modified sugar is a modified activated sugar.

6. The method of claim 1, wherein said glycosyl linking group is an intact glycosyl linking group.

7. The method of claim 1, wherein said modified sugar is a precursor modified sugar that is intracellularly converted to an intermediate modified sugar by cellular enzymes after step b and before step c.

8. The method of claim 7, wherein said intermediate modified sugar is a phosphorylated modified sugar, wherein said phosphorylated modified sugar is formed by intracellularly contacting said modified sugar with a kinase for which said modified sugar is a substrate, thereby forming a phosphorylated modified nucleotide sugar.

9. The method of claim 1, wherein said water-soluble polymer comprises poly(ethylene glycol).

10. The method of claim 9, wherein said poly(ethylene glycol) has a molecular weight distribution that is essentially homodisperse.

11. The method of claim 1, wherein said modified sugar has the formula

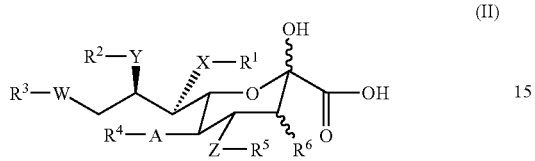

(II)

wherein,
W, X, Y, Z, and A are members independently selected from a bond, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, —O—, —N($R^7$)—, —S—, and —$CH_2$—, wherein, $R^7$ is a member independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; and $R^1$, $R^2$, $R^3$, $R^4$, $R^5$ and $R^6$ are members independently selected from —OH, —$NH_2$, —SH, hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, and a water-soluble polymer, wherein at least one or $R^1$, $R^2$, $R^3$, $R^4$, $R^5$ and $R^6$ is said water-soluble polymer.

12. The method of claim 2, wherein said modified nucleotide sugar has the formula

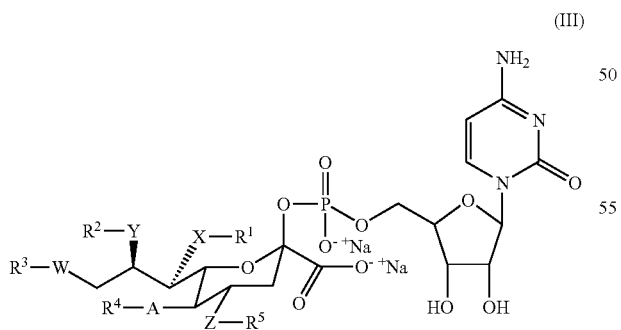

(III)

wherein,
W, X, Y, Z, and A are members independently selected from a bond, substituted or unsubstituted alkylene, substituted or unsubstituted heteroalkylene, substituted or unsubstituted cycloalkylene, substituted or unsubstituted heterocycloalkylene, substituted or unsubstituted arylene, substituted or unsubstituted heteroarylene, —O—, —N($R^7$)—, —S—, and —$CH_2$—, wherein, $R^7$ is a member independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; and $R^1$, $R^2$, $R^3$, $R^4$, and $R^5$ are independently selected from —OH, —$NH_2$, —SH, hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, and a water-soluble polymer, wherein at least one or $R^1$, $R^2$, $R^3$, $R^4$, and $R^5$ is said water-soluble polymer.

13. The method of claim 1, wherein said peptide is selected from the group consisting of granulocyte colony stimulating factor, interferon-alpha, interferon-beta, Factor VIIa, Factor IX, follicle stimulating hormone, erythropoietin, granulocyte macrophage colony stimulating factor, interferon-gamma, alpha-1-protease inhibitor, glucocerebrosidase, tissue plasminogen activator protein, interleukin-2, Factor VIII, chimeric tumor necrosis factor receptor, urokinase, chimeric anti-glycoprotein IIb/IIIa antibody, chimeric anti-HER2 antibody, chimeric anti-respiratory syncytial virus antibody, chimeric anti-CD20 antibody, DNase, chimeric anti-tumor necrosis factor antibody, human insulin, hepatitis B sAg, interferon-omega, alpha-galactosidase A, alpha-iduronidase, anti-thrombin III, human chorionic gonadotropin, and human growth hormone.

14. The method according to claim 2, said modified nucleotide sugar having a formula which is a member selected from:

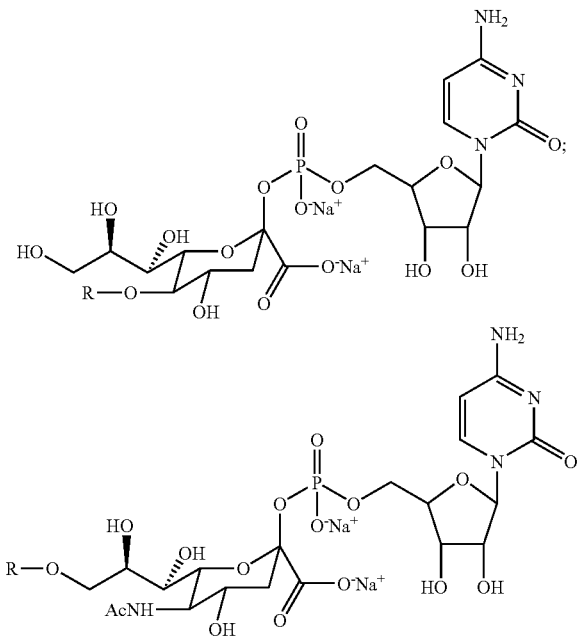

-continued

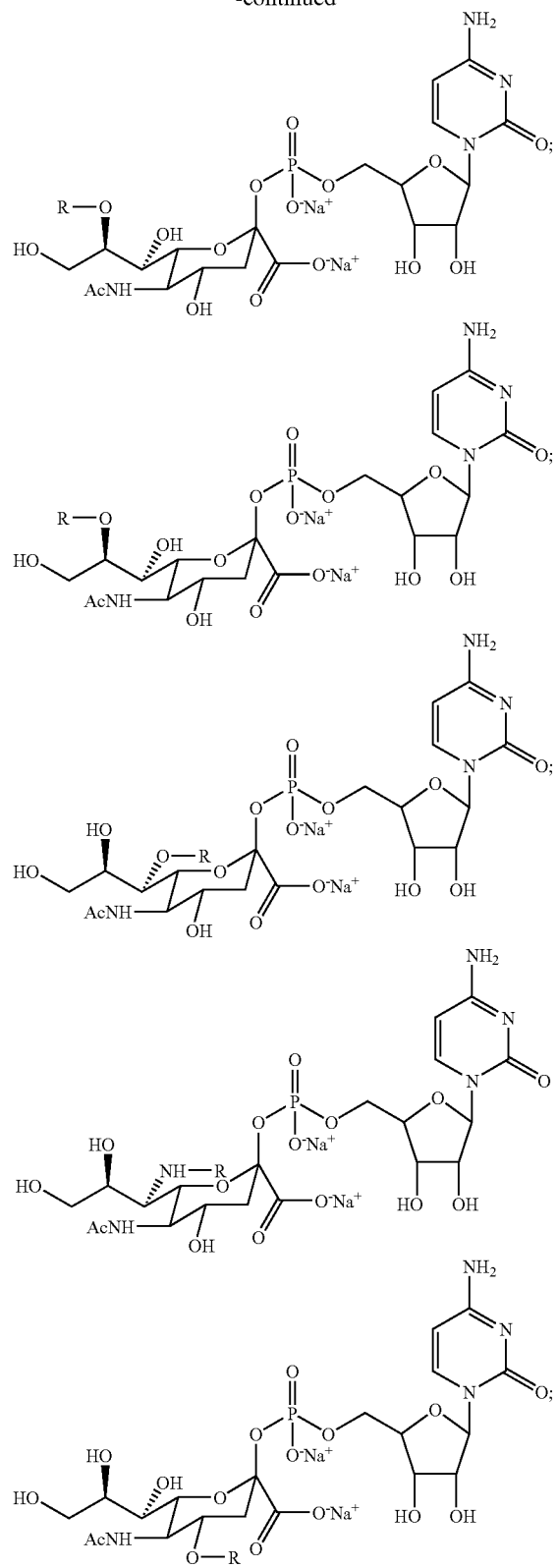

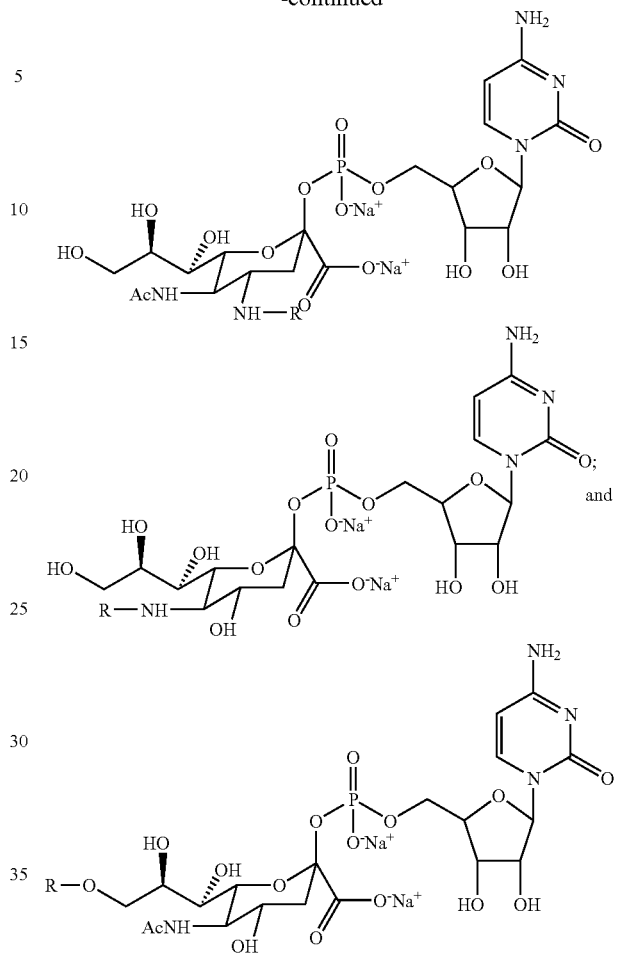

wherein

R is said water-soluble polymer.

15. The method according to claim 1 wherein said water-soluble polymer is a poly(alkylene oxide) selected from linear poly(alkylene oxide) and branched poly(alkylene oxide).

16. The method according to claim 14 wherein said water-soluble polymer is a poly(alkylene oxide) selected from linear poly(alkylene oxide) and branched poly(alkylene oxide).

17. The method according to claim 1 wherein said modified sugar has the formula:

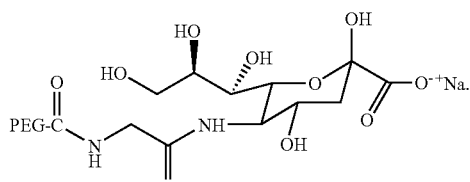

* * * * *